United States Patent [19]
Suenaga et al.

[11] Patent Number: 5,805,720
[45] Date of Patent: Sep. 8, 1998

[54] FACIAL IMAGE PROCESSING SYSTEM

[75] Inventors: Nobumasa Suenaga; Kenji Ogawa, both of Tokyo, Japan

[73] Assignee: Mitsubishi Denki Kabushiki Kaisha, Tokyo, Japan

[21] Appl. No.: 612,815

[22] Filed: Mar. 11, 1996

[30] Foreign Application Priority Data

Jul. 28, 1995 [JP] Japan ................................ 7-193647

[51] Int. Cl.⁶ ........................................ G06K 9/00
[52] U.S. Cl. ..................... 382/117; 351/209; 340/575
[58] Field of Search ........................ 382/117–118, 103, 382/104; 351/209–211; 340/575, 576; 128/745; 180/272; 364/423.098, 424.051

[56] References Cited

U.S. PATENT DOCUMENTS

| 5,218,387 | 6/1993 | Ueno et al. | 351/210 |
| 5,293,427 | 3/1994 | Ueno et al. | 382/117 |
| 5,422,690 | 6/1995 | Rothberg et al. | 351/209 |
| 5,455,601 | 10/1995 | Ozaki | 345/156 |
| 5,570,698 | 11/1996 | Liang et al. | 340/575 |

FOREIGN PATENT DOCUMENTS

| 0552770 | 7/1993 | European Pat. Off. ............... 382/118 |
| 44 41 332 A1 | 11/1993 | Germany . |
| 195 09 689 A1 | 3/1994 | Germany . |
| 196 13 614 A1 | 5/1995 | Germany . |
| 196 03 287 A1 | 7/1995 | Germany . |
| 404174309 | 6/1992 | Japan ....................................... 382/117 |
| 405060515 | 3/1993 | Japan ....................................... 382/117 |
| 6-32154 | 2/1994 | Japan . |

OTHER PUBLICATIONS

Ueno et al, Development of drowsiness detection system, Vehicle Navigation & Information Systems, pp. 15–20, Jul. 1994.

*Primary Examiner*—Leo H. Boudreau
*Assistant Examiner*—Bhavesh Mehta
*Attorney, Agent, or Firm*—Sughrue, Mion, Zinn, Macpeak & Seas, PLLC

[57] ABSTRACT

A facial image processing system of the present invention is provided with an evaluation function calculation device which calculates shape functions (for example, an upper boundary and an approximate line representing a predetermined range of the upper boundary) representing the shape, namely, the feature of the entire eye image from an eye presence area and further calculates an evaluation function (namely, the gradient of the approximate line) from the shape function (namely, the approximate line). The facial image processing system is further provided with an opened-or-closed condition judgment device which determines a threshold value from the values K of the time-varying evaluation function and makes a judgment on whether the eye is opened or closed. Thereby, even in the case that a change in the number of continuous black pixels arranged in Y-direction when closing the eye is small owing to an eyebrow, it can be accurately judged on whether the eye is opened or closed.

32 Claims, 65 Drawing Sheets

WHEN OPENING EYE

WHEN CLOSING EYE

FACIAL IMAGE PROCESSING SYSTEM

BACKGROUND OF THE INVENTION

1. Field of the Invention

The present invention relates to a facial image processing system for detecting various conditions, for example, an unclearly awakening condition and a dozing or drowsy condition of an automobile driver or the like from the opened and closed conditions of his eyes.

2. Description of the Related Art

Hereinafter, a conventional system will be described by referring to FIGS. 63 to 65B. FIG. 63 is a diagram for illustrating the conceptional structure of the conventional system for detecting the condition of a driver, which is disclosed in, for instance, the Japanese Patent Laid-Open No. 6-32154.

As illustrated in FIG. 63, the conventional system is provided with: image input means 1 for inputting data representing an image of the face of a driver and for performing an analog-to-digital (A/D) conversion on the input data; binarization means 2 for binarizing the facial image inputted from (and converted by) the image input means 1; eyeball presence area setting means 3 for determining where an eyeball presence area is in the binarized image; eyeball detecting means 4 for detecting an eyeball in the eyeball presence area on the basis of continuous black pixels (or picture elements) placed in the longitudinal direction (namely, the Y-direction) thereof; opened/closed eye detecting means 5 for detecting the opened or closed eye of the driver on the basis of the number of the continuous black pixels of the detected eyeball; and condition-of-driver judging means 6 for judging the condition of the driver according to the pattern of the opened or closed eye detected by the opened/closed eye detecting means 5.

FIG. 64 illustrates a binary image indicating an eyeball presence area 7 to be processed by the opened/closed eye detecting means 5.

An operation of the conventional system is performed as follows. As illustrated in FIG. 63, an image of the face of a driver, which is taken by using the image input means 1, is binarized by the binarization means 2 and is thus converted into a binary image. In the binary image, the eyeball presence area 7 is established by the eyeball presence setting means 3. The eyeball of the driver is detected in the area 7 by the eyeball detecting means 4. Further, the opened or closed state of the eye is detected by the opened/closed eye detecting means 5. The patterns of the opened and closed eyes are inputted to the condition-of-driver judging means 6 whereupon the dozing condition or the like of the driver is judged.

Further, the operation of the opened/closed eye detecting means 5 will be described hereinbelow in detail. Namely, when detecting an opened or closed eye in the binary image in which, for example, a left eye is preset as illustrated in FIG. 64, the opened/closed eye detecting means 5 searches (namely, scans) an area, in which abscissas (namely, coordinates in the lateral direction) of pixels range from X1 to X2 and ordinates (namely, coordinates in the Y- or longitudinal direction) thereof range from YB (namely, the ordinate of the search starting point) to (YB−50), for black pixels. The longitudinal scanning of 1 line or column of pixels is performed on all columns arranged in the lateral direction of the eyeball presence area 7 repeatedly and sequentially. Upon completion of the scanning of the columns over the full width of the entire eyeball presence area 7, the maximum number of continuous black pixels is obtained as the size in the longitudinal direction (namely, in the Y-direction) of the imaged eyeball of the left eye. Thus, a threshold value for detecting the opened/closed condition of an eye is predetermined on the basis of data concerning the maximum number of continuous black pixels in the cases of the opened and closed conditions thereof. Thereafter, the detection of the opened/closed conditions of an eye can be achieved by comparing the maximum number of continuous black pixels, which is obtained by the aforementioned scanning operation, with the predetermined threshold value.

As above described, the conventional system employs the technique of finding the maximum number of continuous black pixels arranged in the longitudinal direction (namely, the Y-direction) of an eye for judging whether the eye of a driver is opened or closed. However, sometimes, the binary image of the area to be searched becomes as illustrated in FIGS. 65A or 65B, owing to the presence of an eyebrow or a shade. In such a case, there is no large difference between the maximum number L1 of continuous black pixels arranged in the Y-direction in the case of the opened condition of the eye and that L2 of continuous black pixels arranged in the same direction in the case of the closed condition thereof. Thus, the conventional system has encountered the problem that an error of the judgment on whether the eye is opened or closed.

The present invention is accomplished to solve the aforementioned problem of the conventional system.

SUMMARY OF THE INVENTION

It is, accordingly, an object of the present invention to provide a facial image processing system which can accurately judge whether an eye is opened or closed, even in the cases that a change in the number of continuous black pixels arranged in the Y-direction, which occurs at the time of closing the eye, is small and that a change in the maximum number of continuous black pixels arranged in the Y-direction results from a change in the upward or downward direction of a face or from a change in the leftward or rightward inclination of the face, by directing attention to a change in the shape of the eye, which is caused by closing the eye.

To achieve the foregoing object, in accordance with the present invention, there is provided a facial image processing system that comprises: a camera for taking a facial image; image input means for inputting a video signal sent from the camera; binarization means for binarizing the facial image inputted from the image input means; eye extraction means for extracting an eye presence area, which includes an eye, from the binarized facial image; evaluation function calculation means for calculating a shape function representing a shape feature of the eye from the eye presence area and for calculating an evaluation function according to the shape function; and opened/closed condition judgment means for judging according to the evaluation function whether the eye is opened or closed.

Further, in the case of an embodiment of the facial image processing system of the present invention, the evaluation function calculation means obtains a first-order shape function from the binary image of the eye presence area and calculates a second-order shape function according to the first-order shape function and further calculates an evaluation (or performance) function according to the second-order shape function.

Moreover, in the case of another embodiment of the facial image processing system of the present invention, the evaluation function calculation means obtains first and second shape functions from the binary image of the eye presence area and calculates an evaluation function according to the first and second shape functions.

BRIEF DESCRIPTION OF THE DRAWINGS

Other features, objects and advantages of the present invention will become apparent from the following description of preferred embodiments with reference to the drawings in which like reference characters designate like or corresponding parts throughout several views, and in which.

DETAILED DESCRIPTION OF THE PREFERRED EMBODIMENTS

Hereinafter, the preferred embodiments of the present invention will be described in detail by referring to the accompanying drawings.

Embodiment 1

Figure 1:
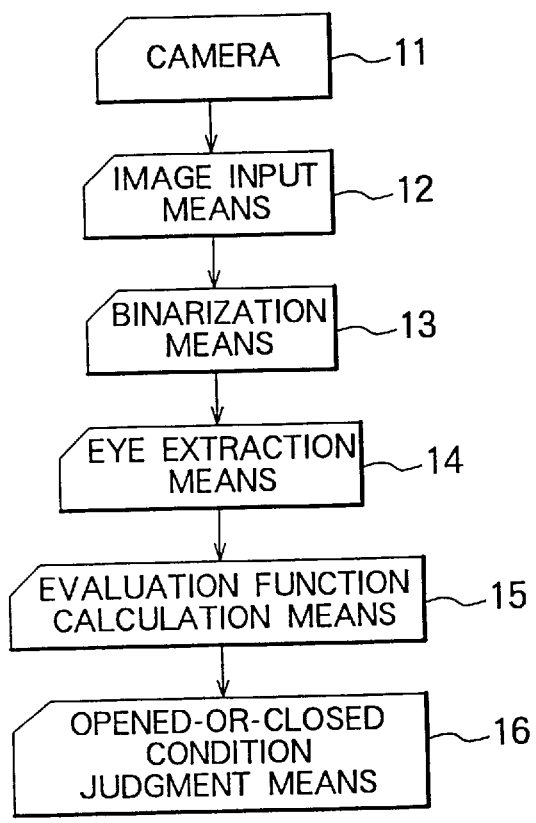
FIG. 1 is a diagram for illustrating the configuration of Embodiment 1 of the present invention.

First, Embodiment 1 of the present invention will be described hereinbelow by referring to FIGS. 1 to 3. FIG. 1 is a diagram for roughly illustrating the configuration of a facial image processing system embodying the present invention, namely, Embodiment 1 of the present invention.

As shown in FIG. 1, this facial image processing system, namely, Embodiment 1 of the present invention is provided with a camera 11, an image input means 12, a binarization means 13, an eye extraction means 14, an evaluation function calculation means 15 and an opened-or-closed condition judgment means 16.

The camera 11 is, for example, a CCD TV camera provided on an instrument panel and is used to take an image of the face of a driver. Further, an analog picture signal (or video signal) outputted from this camera 11 is processed by the aforementioned means 12 to 16. Moreover, when it is judged that the driver is in the dozing condition, the attention of the driver is attracted by, for instance, sounding a buzzer, giving a voice warning, or vibrating the driver's seat. Furthermore, if necessary, a car is stopped by, for example, operating a brake.

A facial image taken by the camera 11 is inputted to the image input means 12 whereupon an A/D conversion is performed on data representing the facial image to thereby convert the facial image into a digital half-tone image (namely, a digital gradation or gray-scale image). Then, the binarization of the digital half-tone image is performed by the binarization means 13 by using a predetermined threshold value. Namely, the digital half-tone image is converted into a binary image consists of, for instance, black and white pixels. Subsequently, an eye presence area is extracted by the eye extraction means 14. This eye extraction means 14 finds the barycenter or centroid by, for example, calculating the mean value or average of the coordinates of the black pixels. Further, the eye extraction means 14 extracts a rectangular area of the predetermined lateral range (namely, the predetermined range in the X-direction), in which a cluster of black pixels closest to the barycenter or centroid is present, as the eye presence area. Thereafter, the evaluation function calculation means 15 calculates a shape function representing the shape or feature of the entire binary eye image contained in the eye presence area. Subsequently, the evaluation function calculation means 15 calculates an evaluation function, which should be obtained by directing attention to the arcuate shape of the eye, from this shape function. Then, the evaluation function calculation means 15 records the values K of this evaluation function in a memory. Further, the opened-or-closed condition judgment means 16 determines a threshold value from the values K of the time-varying evaluation function and judges whether the eye is opened or closed.

Figure 2:
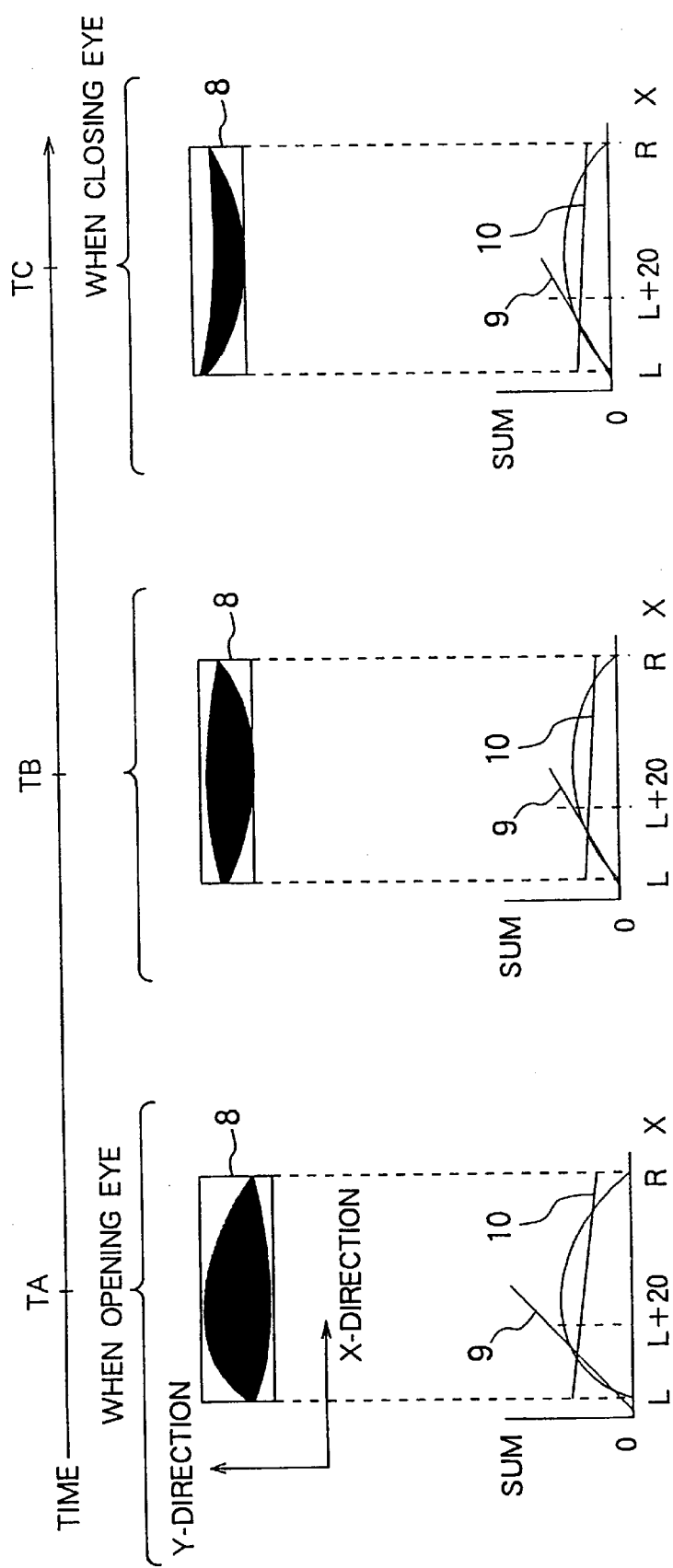
FIG. 2 is a diagram for illustrating a method for detecting the opened or closed condition of an eye, which is employed by Embodiment 1 of the present invention.

FIG. 2 is a diagram for illustrating a method, which is used in Embodiment 1 of the present invention, of judging whether or not the eye is opened or closed. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and "Y-histograms" which are first-order shape functions and are defined herein as graphs for showing the distribution of the values obtained by accumulating the binary tone levels of pixels arranged in the Y-direction correspondingly to each of the X-coordinates in the eye presence area 8, and approximate lines which are second-order shape functions and are calculated on the basis of the first-order shape functions. Additionally, each of the Y-histograms is practically obtained by scanning the eye presence area 8 in the Y-direction and counting (namely, summing up the number of) the black pixels corresponding to each of the X-coordinates (incidentally, "SUM" represents the count (namely, the total number) of the black pixels corresponding to each of the X-coordinates).

Figure 3:
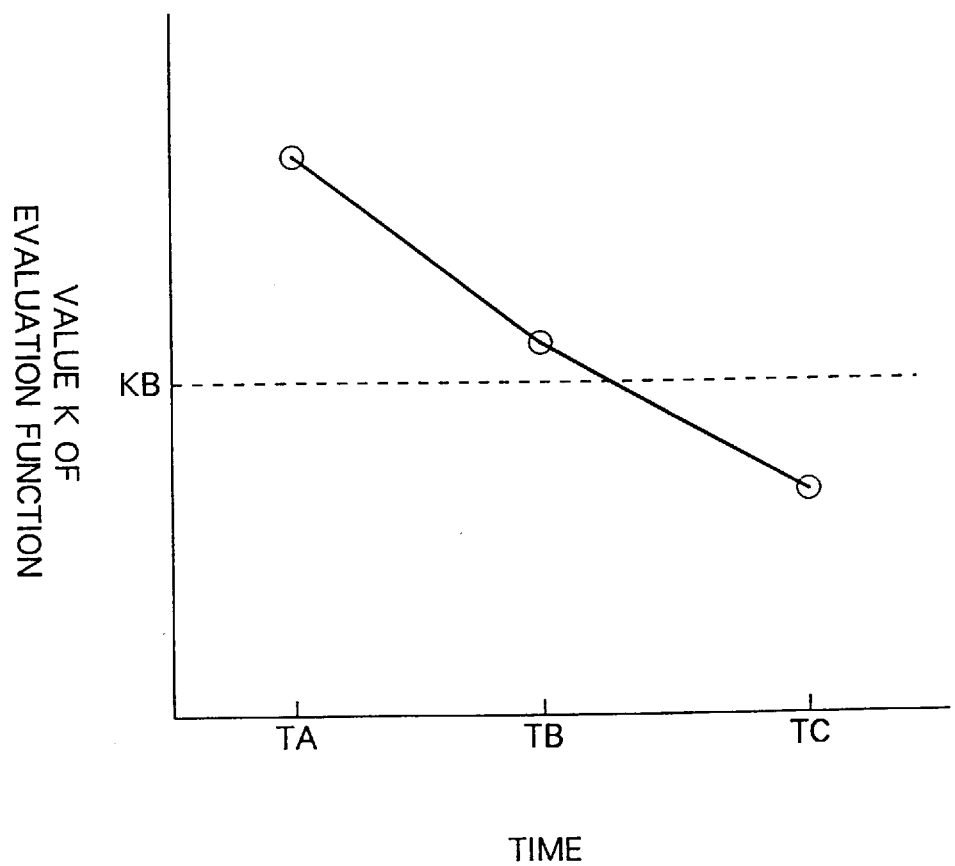
FIG. 3 is a graph for illustrating how an evaluation function employed by Embodiment 1 of the present invention varies with time.

FIG. 3 illustrates a change in the value K of the evaluation function which is the gradient of the approximate line calculated from the Y-histogram of FIG. 2.

Further, a line 9 is an approximate line obtained by utilizing a method of least squares (namely, a least square method) as a figure having a shape sufficiently close to the shape of a predetermined part of the curve represented by the Y-coordinates (namely, the count SUM) respectively corresponding to the X-coordinates from L (corresponding to the left end of the eye presence area 8) to (L+20). In this case, the method of least squares is performed according to the following equation (1). Further, K denotes the gradient of the approximate line 9 and thus represents the value of the evaluation function. Incidentally, in the equation (1), each summation is performed with respect to X of L to (L+20).

$$K = \{20\Sigma(XSUM) - \Sigma x \times \Sigma SUM\} / \{20\Sigma(X^2) - (\Sigma X)^2\} \quad (1)$$

As illustrated in FIG. 2, as the condition of the eye is changed from the opened condition to the closed condition, the shape of the Y-histogram changes. Consequently, at the moment TC when the eye is opened, the value K of the evaluation function is low, as shown in FIG. 3. Thus, as a result of collecting sample data and setting a threshold value KB according to the tendency in the sampled values K, it can be judged whether the eye is opened or closed. Namely, for example, when the value K of the evaluation function is lower than the threshold value KB, it is judged that the eye is closed.

Further, an approximate line 10 to be substituted for the shape of the entire eye, namely, for the shape of the entire range of the eye presence area 8 is similarly obtained. Then, the gradient of the approximate line 10 is calculated. Moreover, the difference between the gradients of the approximate lines 9 and 10 is used as the evaluation function. Thereby, this embodiment has advantages or effects in that the possibility of an occurrence of an erroneous detection due to the inclination of the face of the driver is reduced and that thus, the accuracy of making a judgment on the opened or closed condition of the eye is improved. Incidentally, the value of the evaluation function in this case has a tendency similar to those of the function of FIG. 3.

Additionally, in the aforementioned case, the shape of the predetermined range of the left end portion of the eye is used for obtaining the evaluation function. However, although the sign of the function is reversed, a similar result can be obtained in the case that the shape of the predetermined range of the right end portion of the eye, for example, the range of the X-coordinates from R to (R−20) is used therefor. Incidentally, the value of the evaluation function in this case also has a tendency similar to those of the function of FIG. 3.

In addition, the precision of making a judgment on the opened or closed condition of the eye can be enhanced by using the value of a function represented by one of approximate lines, whose gradient is larger than that of the other approximate line, as the value of the evaluation function.

Embodiment 2

Figure 4:
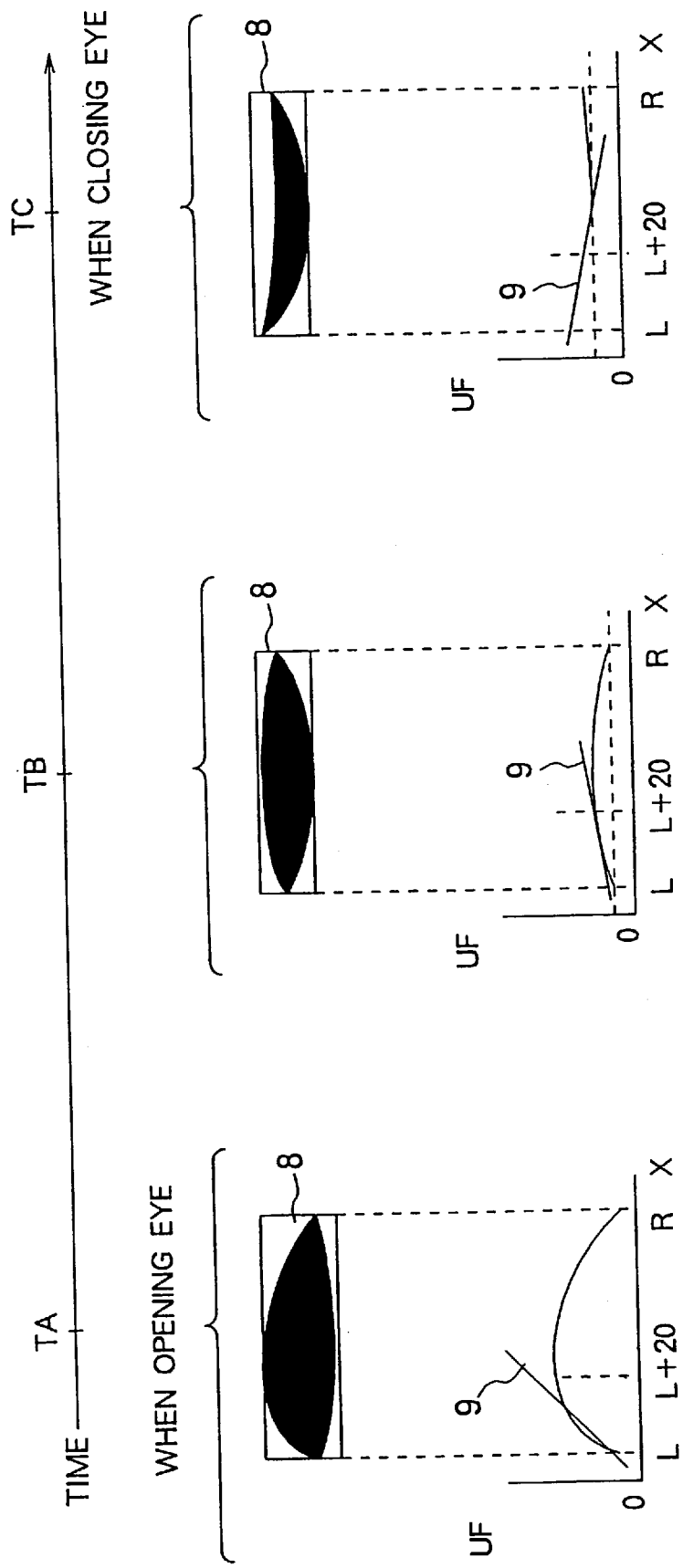
FIG. 4 is a diagram for illustrating a method for detecting the opened or closed condition of an eye, which is employed by Embodiment 2 of the present invention.

Next, Embodiment 2 of the present invention will be described hereinbelow by referring to FIGS. 4 and 5. FIG. 4 is a diagram for illustrating a method for detecting the opened and closed conditions of an eye, which is employed by Embodiment 2 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, upper boundary shape functions) respectively using the coordinates of the upper boundaries of the binary images, and approximate lines which are second-order shape functions calculated from the first-order shape functions. Additionally, each of the upper boundary shape functions is practically obtained by upwardly scanning the eye presence area 8 in the Y-direction and counting the black pixels corresponding to each of the X-coordinates until the final black pixel is detected (incidentally, "UF" represents the count (namely, the total number) of the black pixels corresponding to each of the X-coordinates).

Figure 5:
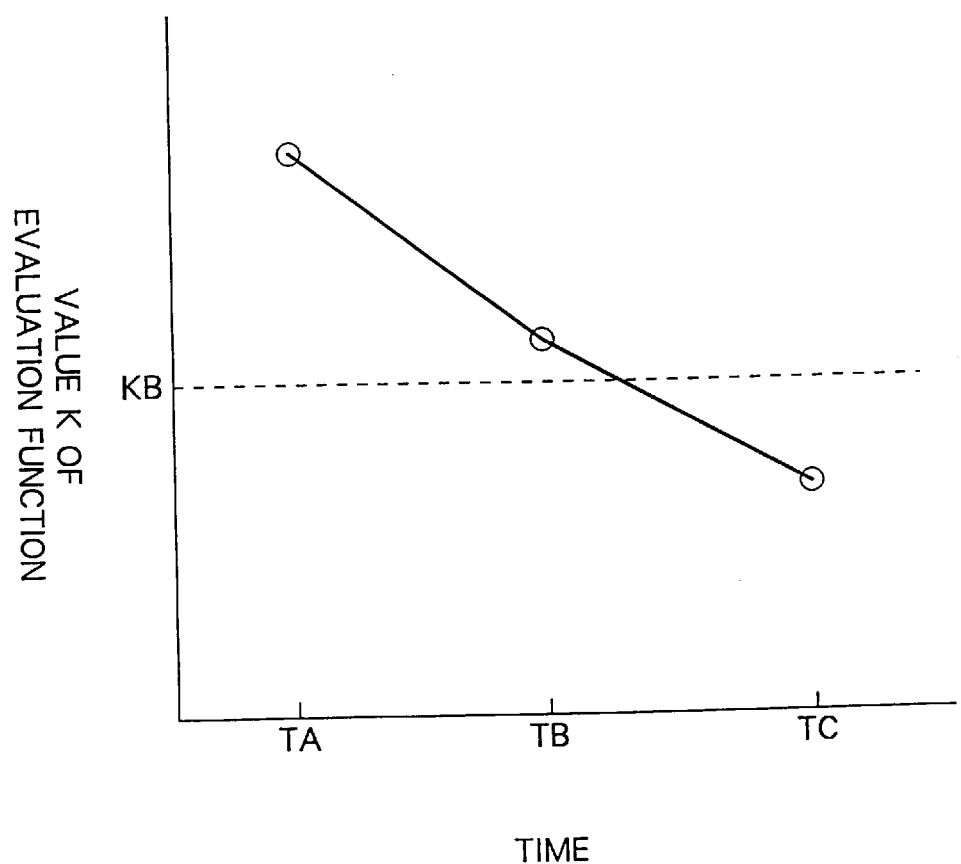
FIG. 5 is a graph for illustrating how an evaluation function employed by Embodiment 2 of the present invention varies with time.

FIG. 5 illustrates a change in the value K of the evaluation function, which is the gradient of the approximate line calculated from the upper boundary shape function of FIG. 4.

In the case of a method employed in Embodiment 2 of the present invention, when the eye is opened or closed, the upper boundary shape function changes, similarly as in the case of the method employed in Embodiment 1 thereof.

Embodiment 3

Figure 6:
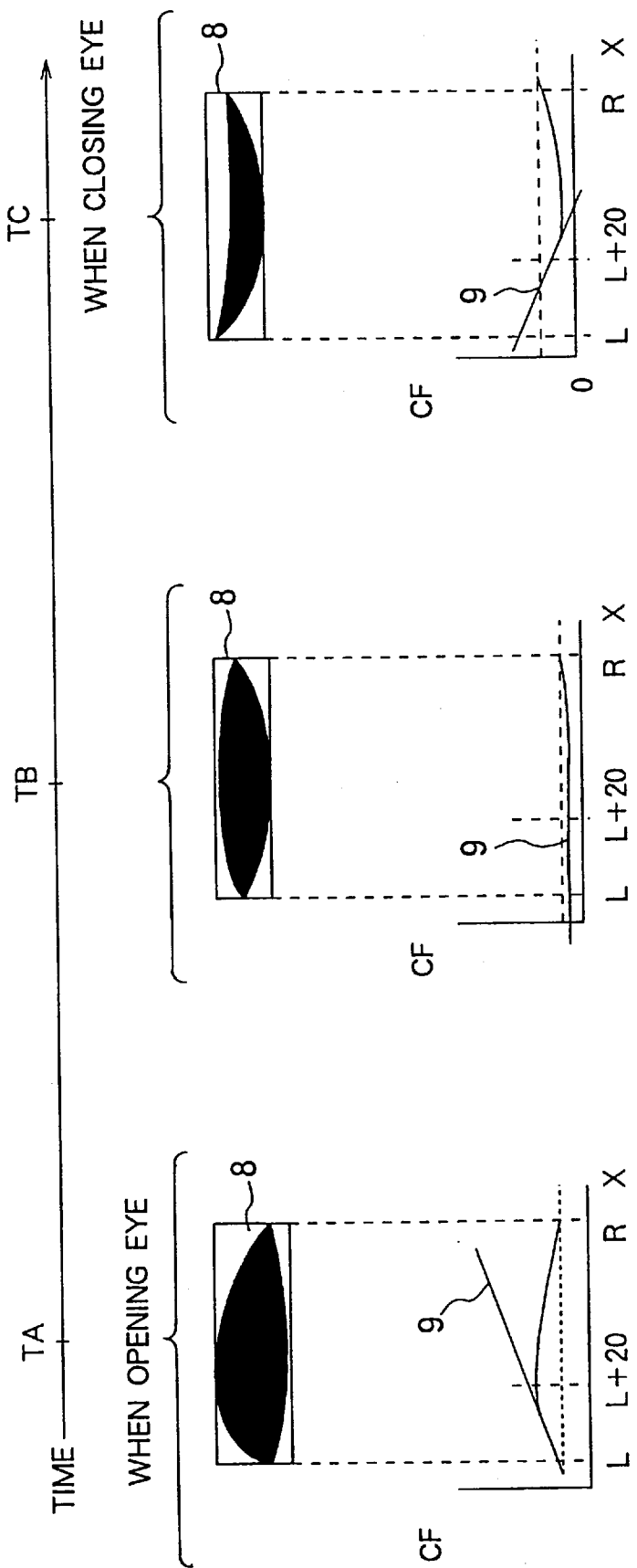
FIG. 6 is a diagram for illustrating a method for detecting the opened or closed condition of an eye, which is employed by Embodiment 3 of the present invention.

Next, Embodiment 3 of the present invention will be described hereinbelow by referring to FIGS. 6 and 7. FIG. 6 is a diagram for illustrating a method for detecting the opened or closed condition of an eye, which is employed by Embodiment 3 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, Y-center-locus shape functions) respectively using the shape of what is called a Y-center-locus (namely, the line or curve connecting the centers of intersections of the binary image of the eye with lines parallel to the Y-axis), and approximate lines which are second-order shape functions calculated from the first-order shape functions. Additionally, each of the Y-center-locus shape functions is practically obtained by upwardly scanning the eye presence area 8 in the Y-direction and measuring the Y-coordinates of the first and last black pixels correspondingly to each of the X-coordinates and obtaining the mean or average of the Y-coordinates of the first and last black pixels corresponding to each of the X-coordinates (incidentally, "CF" represents the mean or average of the Y-coordinates of the first and last black pixels corresponding to each of the X-coordinates).

Figure 7:
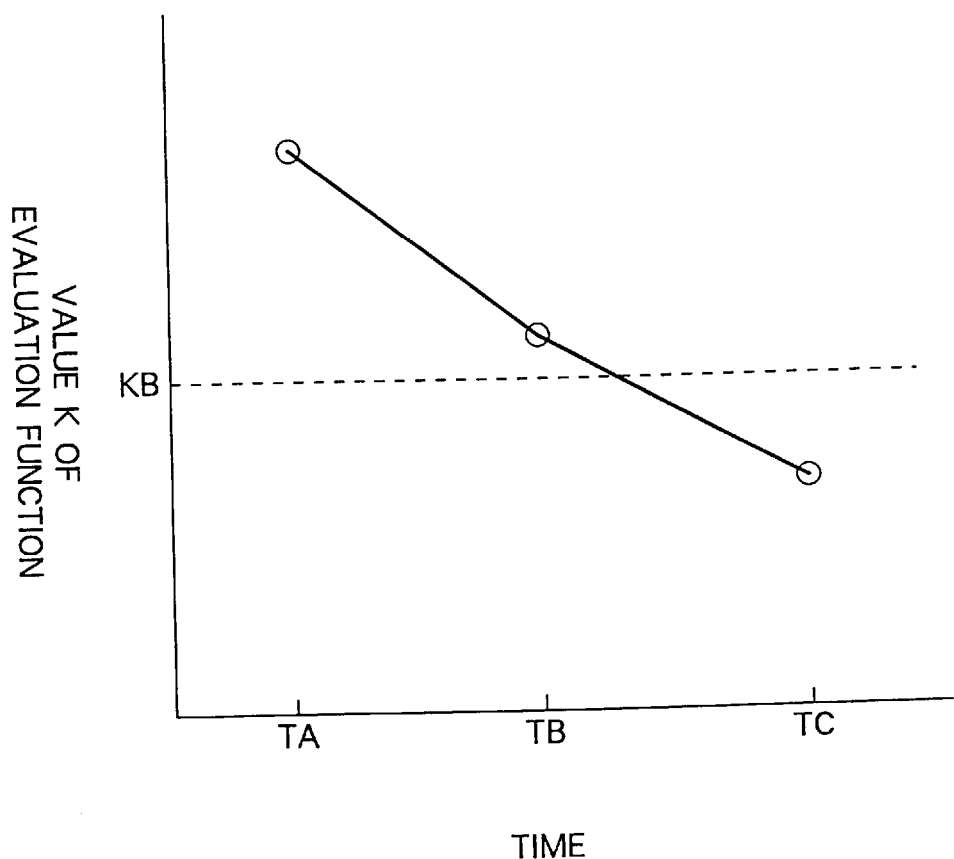
FIG. 7 is a graph for illustrating how an evaluation function employed by Embodiment 3 of the present invention varies with time.

FIG. 7 illustrates a change in the value K of the evaluation function, which is the gradient of the approximate line calculated from the Y-center-locus shape function of FIG. 6.

In the case of a method employed in Embodiment 3 of the present invention, when the eye is opened or closed, the Y-center-locus shape function changes, similarly as in the case of the method employed in Embodiment 1 thereof. Thus, it can be detected whether the eye is opened or closed. Incidentally, the method employed in Embodiment 3 is similar to that employed in Embodiment 1 except that the Y-center-locus is employed as the first-order shape function.

Embodiment 4

Figure 8:
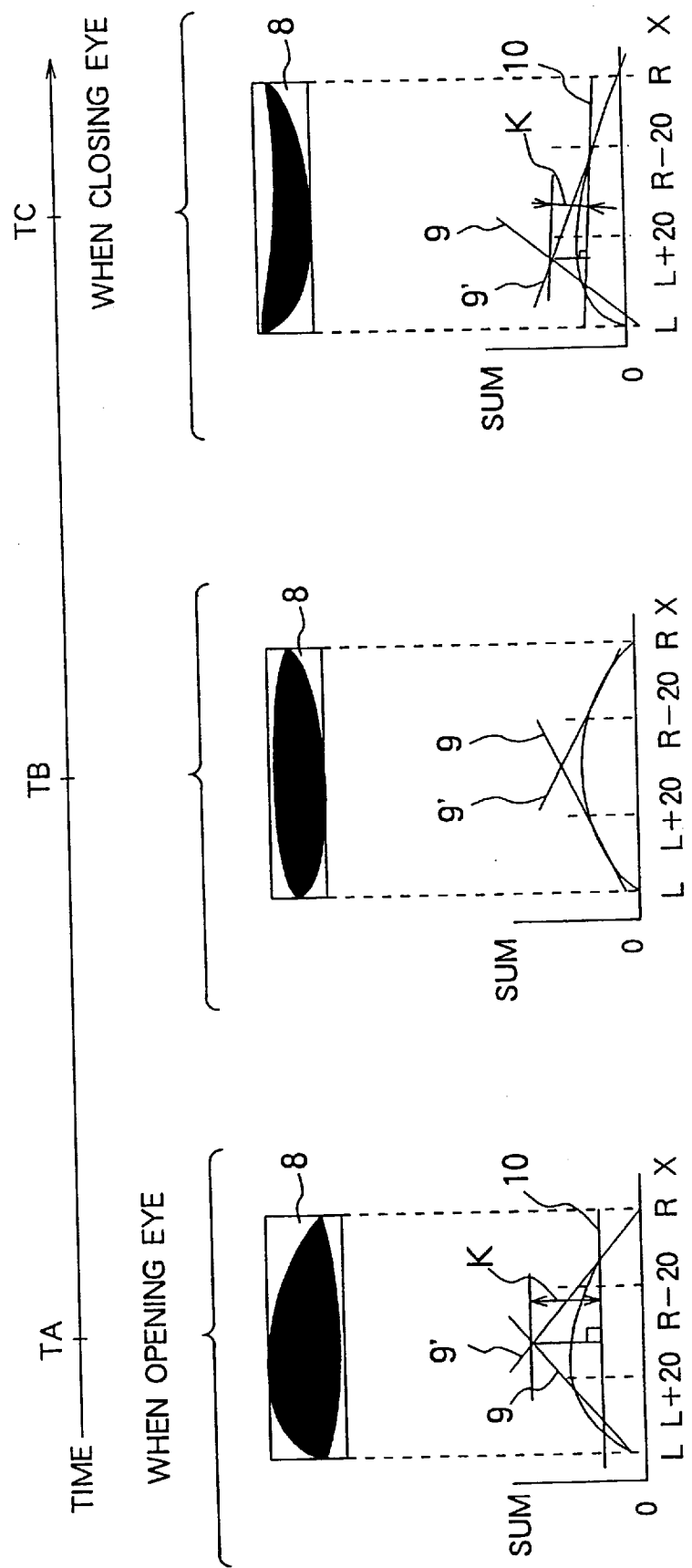
FIG. 8 is a diagram for illustrating a method for detecting the opened or closed condition of an eye, which is employed by Embodiment 4 of the present invention.

Next, Embodiment 4 of the present invention will be described hereinbelow by referring to FIGS. 8 and 9. FIG. 8 is a diagram for illustrating a method for detecting the opened and closed conditions of an eye, which is employed by Embodiment 4 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and Y-histograms which are first-order shape functions corresponding to the binary images of the eye presence area 8, and approximate lines which are second-order shape functions and are calculated from the first-order shape functions.

Figure 9:
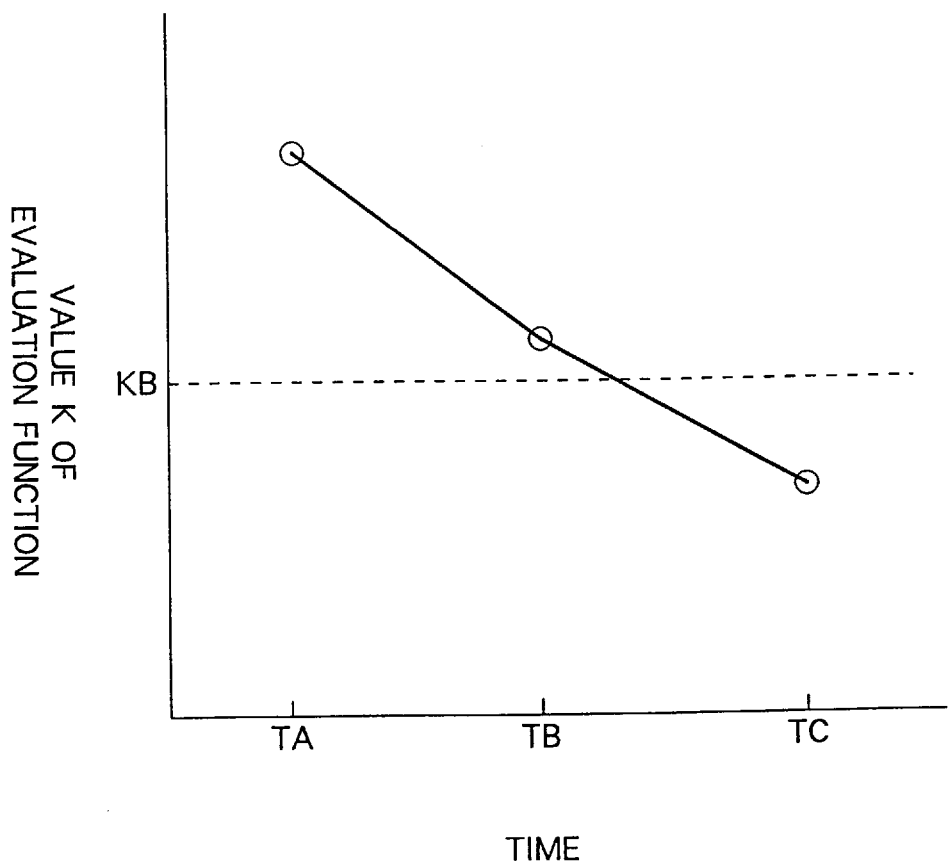
FIG. 9 is a graph for illustrating how an evaluation function employed by Embodiment 4 of the present invention varies with time.

FIG. 9 illustrates a change in the value K of the evaluation function, which is the difference between the gradients of the two approximate lines calculated from the Y-histograms of FIG. 8.

Further, lines 9 and 9' are approximate lines obtained by utilizing a method of least squares as figures having shapes sufficiently close to the shapes of predetermined left-end and right-end parts of the Y-histogram, which correspond to a range of the X-coordinates from L (corresponding to the left end of the eye presence area 8) to (L+20) and another range of the X-coordinates from R (corresponding to the right end of the eye presence area 8) to (20–R). In this case, the difference between the gradients of the approximate lines 9 and 9', which is expressed by using the following equation (2), is the value K of the evaluation function. Incidentally, in the equation (2), each summation of the first half part or item of the left side thereof is performed with respect to X of L to (L +20) and each summation of the second half part or item of the right side thereof is performed with respect to X of R to (20–R)

$$K=\{20\Sigma(XSUM)-\Sigma\times\Sigma SUM\}/\{20\Sigma(X^2)-(\Sigma X)^2\}-\{20\Sigma(XSUM)-\Sigma\times\Sigma SUM\}/\{20\Sigma(X^2)-(\Sigma X)^2\} \quad (2)$$

As illustrated in FIG. 8, when the eye is opened or closed, the shape of the Y-histogram changes. As a result, at the time TC when the eye is closed, the value K of the evaluation function is low. Thus, a threshold value KB is set, and it can be detected whether the eye is opened or closed.

In the case of the method employed by this Embodiment 4, the shapes of the predetermined ranges of both of the left and right end portions are used for obtaining the evaluation function, so that the change in the value K of the evaluation function owing to the inclination of the face of a driver becomes small. Consequently, this embodiment has an advantage or effect in that it can be accurately detected whether the eye is opened or closed.

Moreover, similarly, an approximate line 10 corresponding to the entire eye is obtained. Thus, the height of a triangle formed by the three approximate lines 9, 9' and 10, which correspond to the predetermined ranges of the left-end portion, the right end portion and the entirety of the eye, respectively, may be used as the value of the evaluation function. Consequently, this embodiment has advantages and effects in that the possibility of an occurrence of an erroneous detection due to a shade at the corner of the eye can be reduced and that the accuracy of judging the opened-or-closed conditions of the eye can be further enhanced.

Embodiment 5

Figure 10:
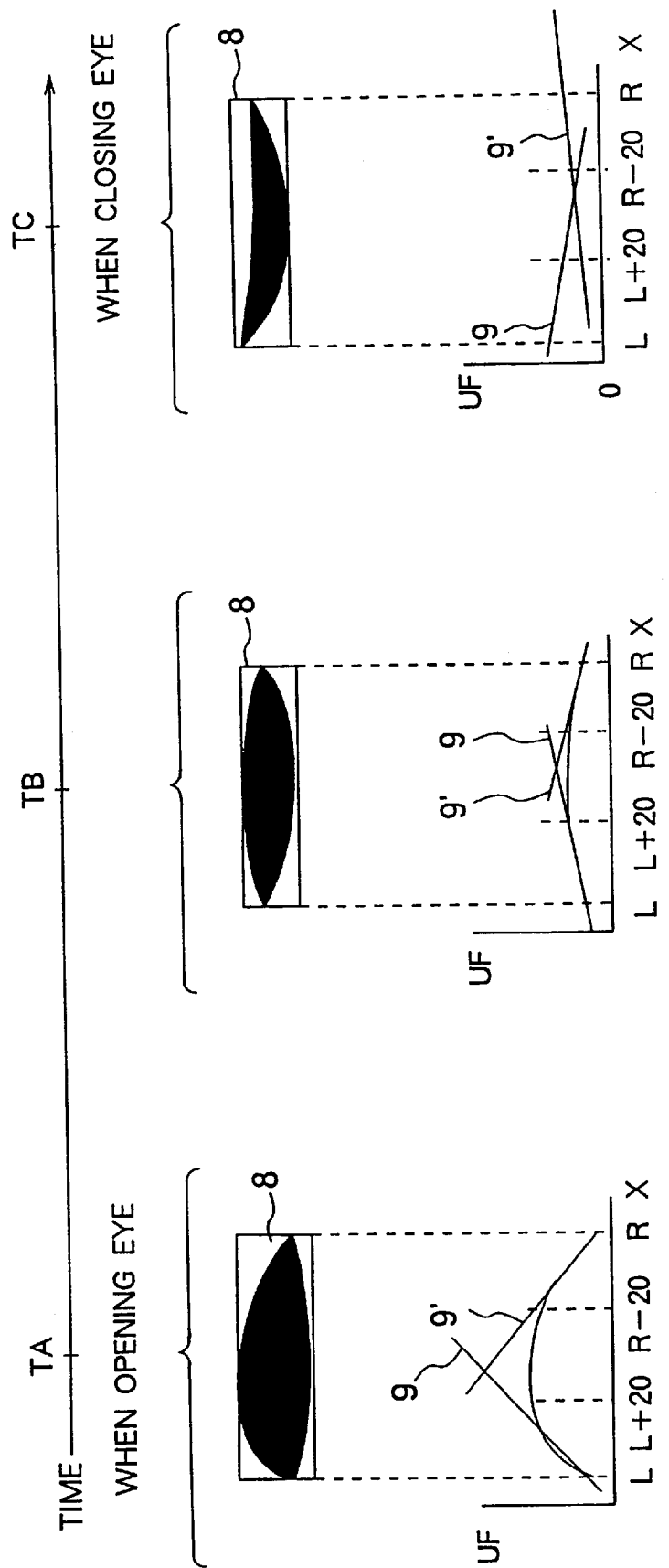
FIG. 10 is a diagram for illustrating a method for detecting the opened or closed condition of an eye, which is employed by Embodiment 5 of the present invention.

Next, Embodiment 5 of the present invention will be described hereinbelow by referring to FIGS. 10 and 11. FIG. 10 is a diagram for illustrating a method for detecting the opened or closed condition of an eye, which is employed by Embodiment 5 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, upper boundary shape functions) respectively using the coordinates of the upper boundaries of the binary images, and approximate lines which are second-order shape functions calculated on the basis of the first-order shape functions.

Figure 11:
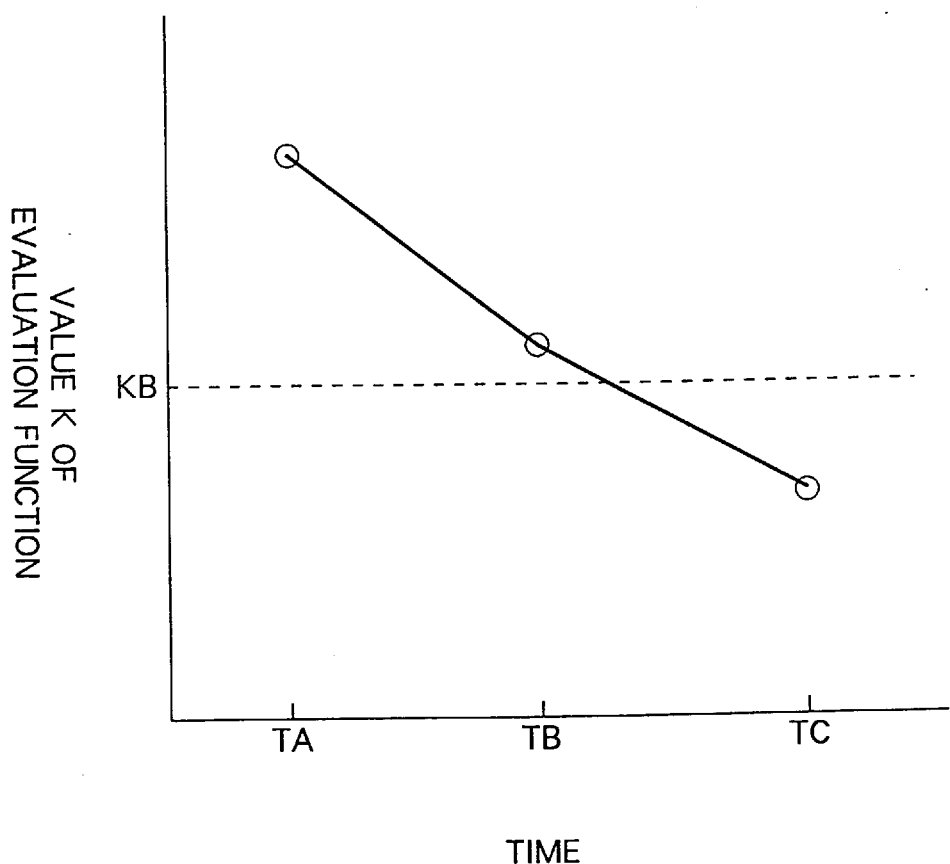
FIG. 11 is a graph for illustrating how an evaluation function employed by Embodiment 5 of the present invention varies with time.

FIG. 11 illustrates a change in the value K of the evaluation function that is the difference between the gradients of the two approximate lines which are obtained by the calculation based on the upper boundary shape function of FIG. 10.

In the case of performing the method employed in Embodiment 5 of the present invention, when the eye is opened or closed, the upper boundary shape function changes, similarly as in the case of the method employed in Embodiment 4 thereof. Thus, it can be detected whether the eye is opened or closed. Incidentally, the method employed in Embodiment 5 is similar to that employed in Embodiment 4 except that the upper boundary is employed as the first-order shape function.

Embodiment 6

Figure 12:
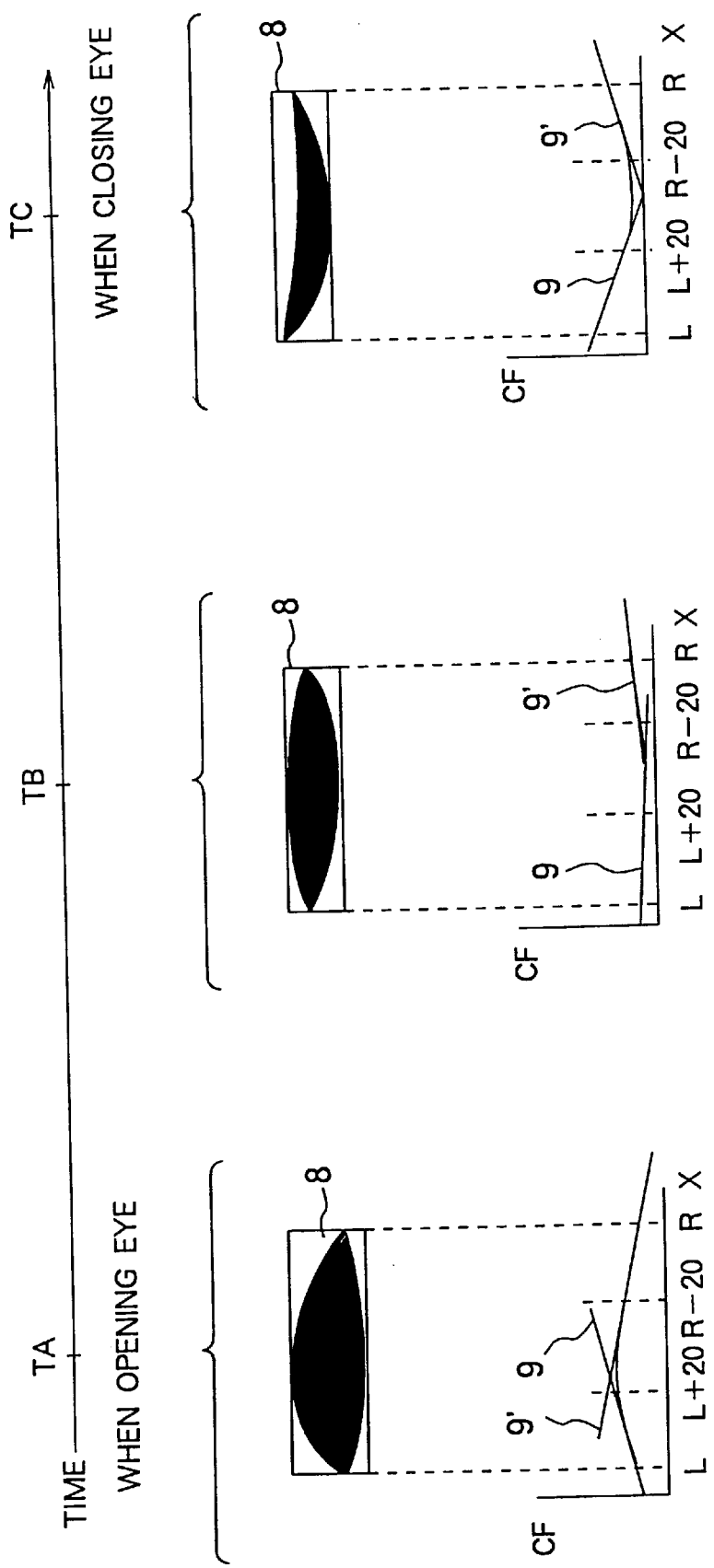
FIG. 12 is a diagram for illustrating a method for detecting the opened or closed condition of an eye, which is employed by Embodiment 6 of the present invention.

Next, Embodiment 6 of the present invention will be described hereinbelow by referring to FIGS. 12 and 13. FIG. 12 is a diagram for illustrating a method for detecting the opened or closed condition of an eye, which is employed by Embodiment 6 of the present invention. This figure illustrates the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, Y-center-locus shape functions) respectively using the shape of what is called the Y-center-locus, and approximate lines which are second-order shape functions calculated on the basis of the first-order shape functions.

Figure 13:
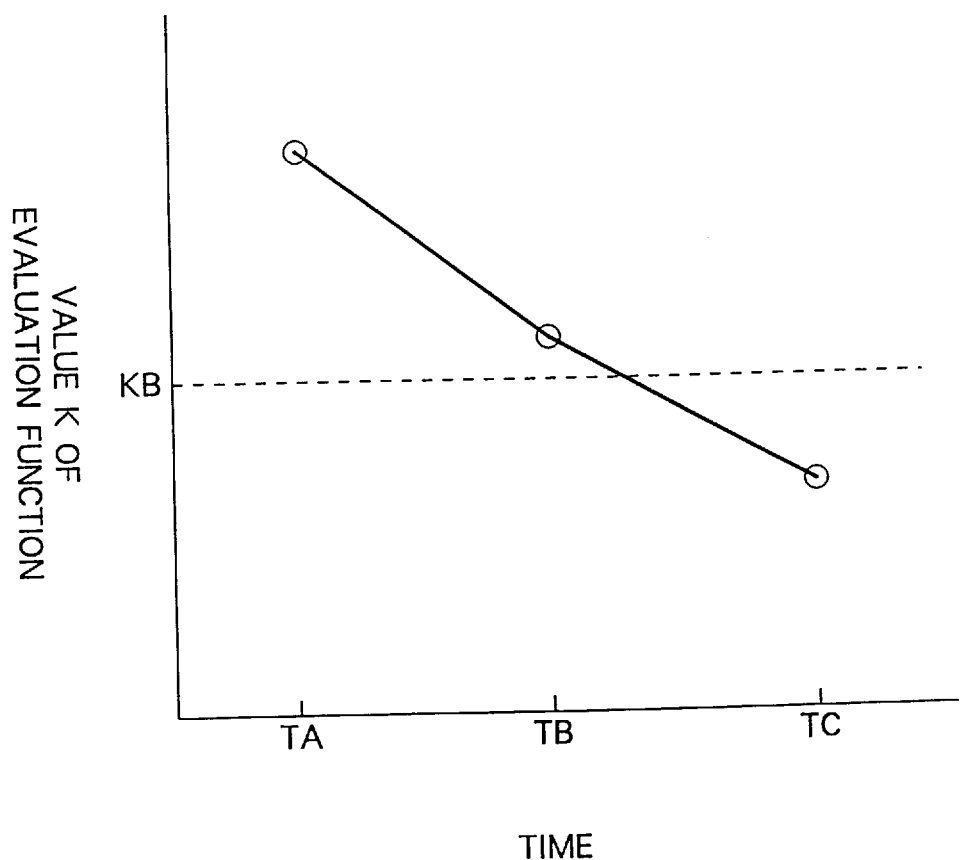
FIG. 13 is a graph for illustrating how an evaluation function employed by Embodiment 6 of the present invention varies with time.

FIG. 13 illustrates a change in the value K of the evaluation function that is the difference between the gradients of the two approximate lines which are obtained by the calculation based on the Y-center-locus shape functions of FIG. 12.

In the case of performing the method employed in Embodiment 6 of the present invention, when the eye is opened or closed, the Y-center-locus shape function changes, similarly as in the case of the method employed in Embodiment 4 thereof. Thus, it can be detected whether the eye is opened or closed. Incidentally, the method employed in Embodiment 6 is similar to that employed in Embodiment 4 except that the Y-center-locus is employed as the first-order shape function.

Embodiment 7

Figure 14:
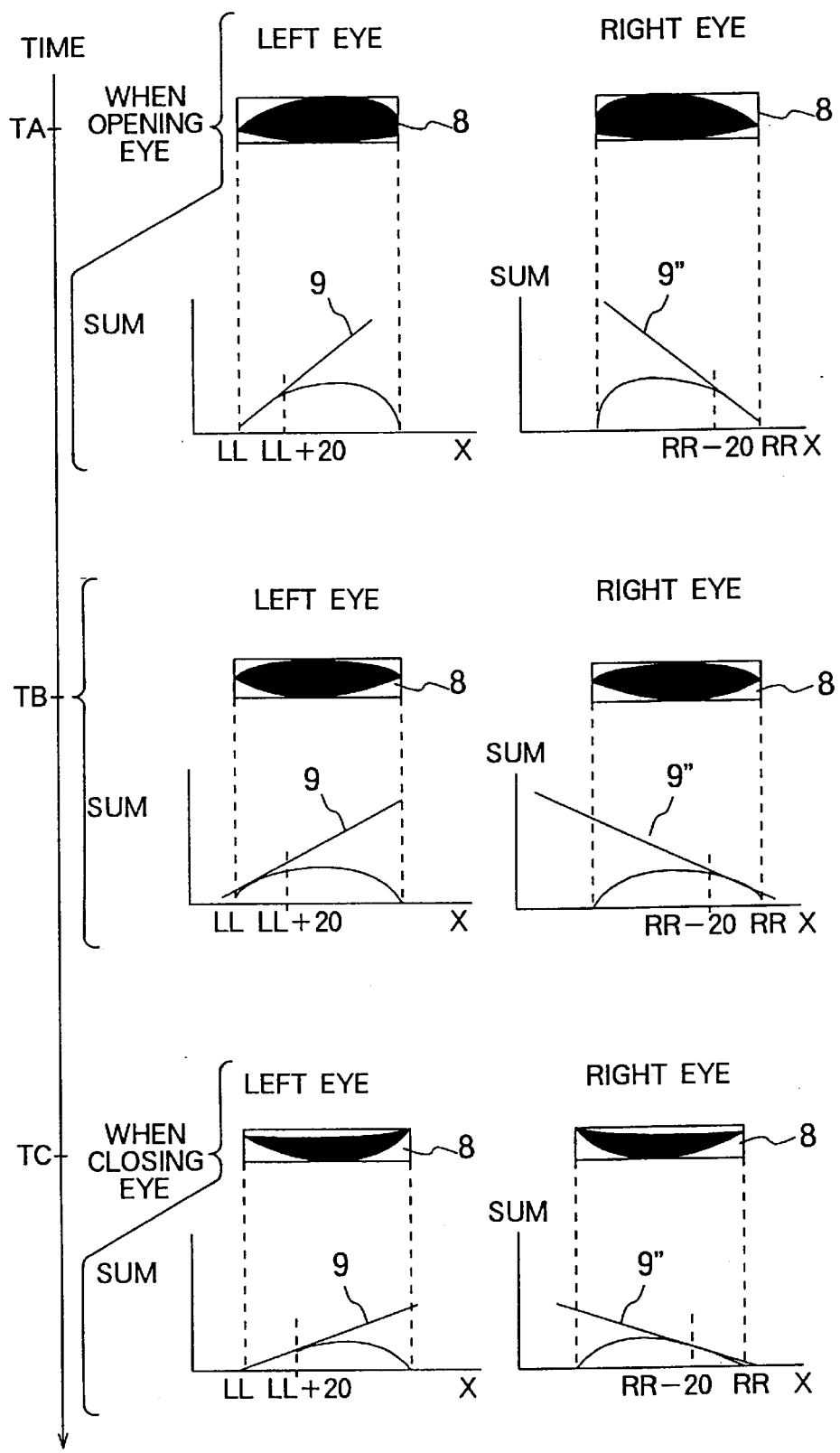
FIG. 14 is a diagram for illustrating a method for detecting the opened or closed condition of an eye, which is employed by Embodiment 7 of the present invention.

Next, Embodiment 7 of the present invention will be described hereinbelow by referring to FIGS. 14 and 15. FIG. 14 is a diagram for illustrating a method for detecting the opened or closed condition of an eye, which is employed by Embodiment 7 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and Y-histograms which are first-order shape functions corresponding to the binary images of the eye presence area 8, and approximate lines which are second-order shape functions calculated on the basis of the first-order shape functions.

Figure 15:
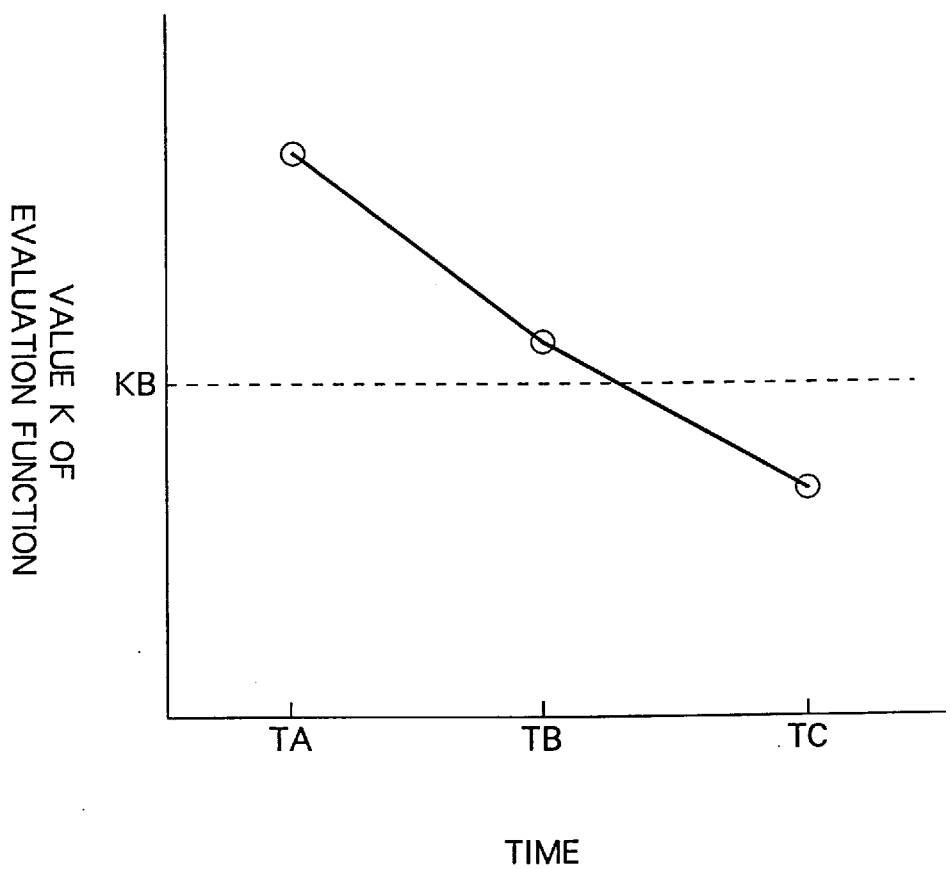
FIG. 15 is a graph for illustrating how an evaluation function employed by Embodiment 7 of the present invention varies with time.

FIG. 15 illustrates a change in the value K of the evaluation function, that is the difference between the gradients of the two approximate lines calculated on the basis of the Y-histograms of FIG. 14.

Further, lines 9 and 9" are approximate lines obtained by utilizing a method of least squares as figures having shapes enough close to the shapes of predetermined parts (namely, a range of the X-coordinates from LL to (LL+20) and another range of the X-coordinates from RR (corresponding to the right end of the eye presence area 8) to (20−RR)) of the Y-histograms, which correspond to outer end portions of both of the left and right eyes. In this case, the difference between the gradients of the approximate lines 9 and 9" is the value K of the evaluation function.

As illustrated in FIG. 14, when the eye is opened or closed, the shape of the Y-histogram changes. As a consequence, at the time TC when the eye is closed, the value K of the evaluation function is low, as shown in FIG. 15. Thus, a threshold value KB is set, and it can be detected whether the eye is opened or closed.

Further, in this case, the shapes of the predetermined ranges of the outer end portions respectively corresponding to the left and right eyes are used for obtaining the evaluation function. However, although the sign of the function is reversed, a similar effect can be obtained in the case that the shapes of the predetermined ranges of the inner end portions of the left and right eyes are used.

In the case of the method employed by this Embodiment 7, the symmetric shapes of the predetermined ranges of both of the left and right end portions are used for obtaining the evaluation function, so that the change in the value K of the evaluation function owing to the inclination of the face of a driver becomes small. Consequently, this embodiment has advantages and effects in that erroneous detections due to a shade at the corner of the eye can be reduced and that it can be accurately detected whether the eye is opened or closed.

Moreover, in the case that evaluation functions are respectively calculated correspondingly to the predetermined ranges of the outer end portions of the left and right eyes and to the predetermined ranges of the inner end portions of the left and right eyes and that one of the evaluation functions, which varies with time more largely than the other evaluation function, is used, this embodiment has an advantage in that the accuracy of judging the opened-or-closed conditions of the eye can be further enhanced.

Embodiment 8

Figure 16:
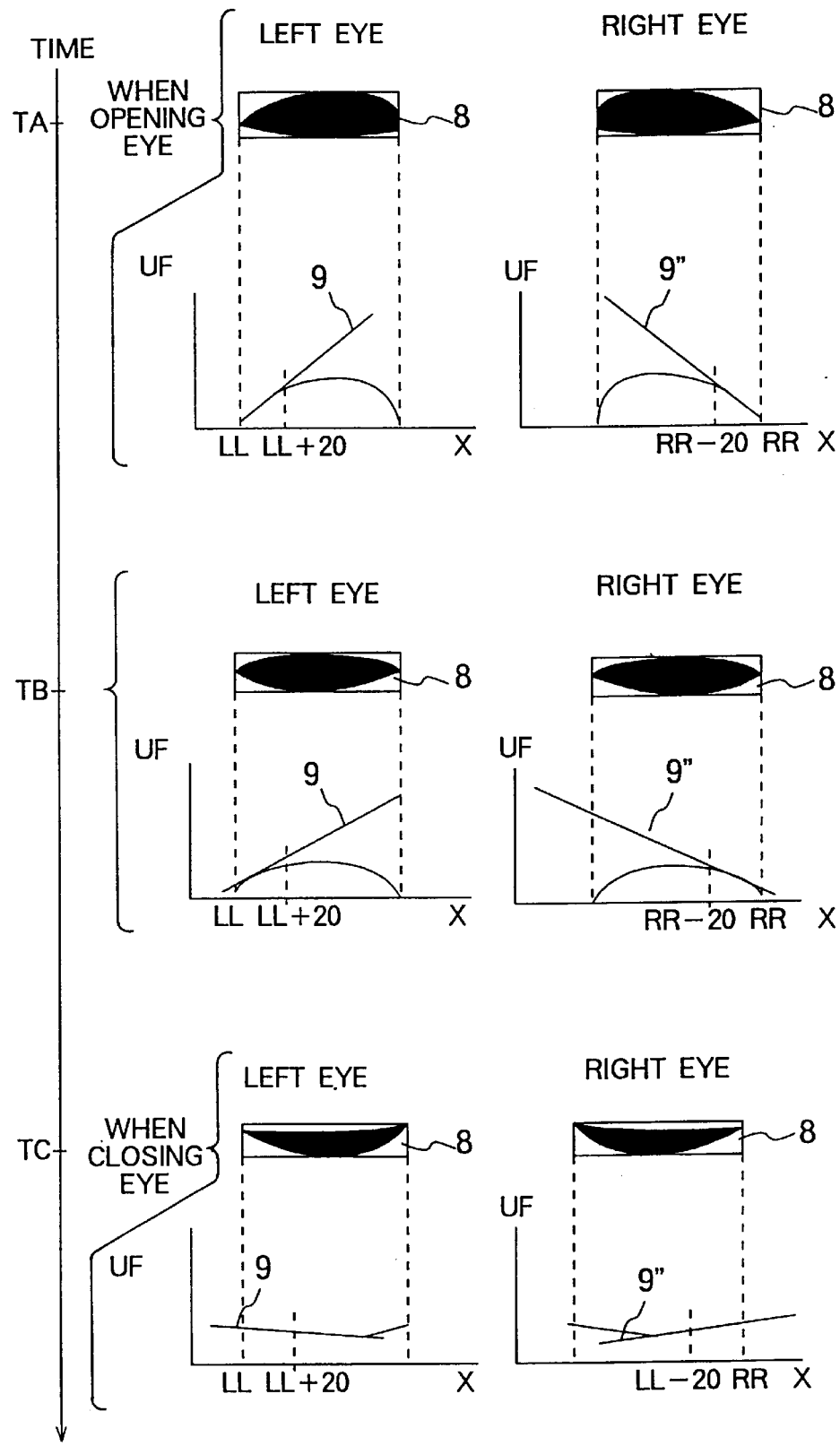
FIG. 16 is a diagram for illustrating a method for detecting the opened or closed condition of an eye, which is employed by Embodiment 8 of the present invention.

Next, Embodiment 8 of the present invention will be described hereinbelow by referring to FIGS. 16 and 17. FIG. 16 is a diagram for illustrating a method for detecting the opened or closed condition of an eye, which is employed by Embodiment 8 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, upper boundary shape functions) respectively using the coordinates of the upper boundaries of the binary images, and approximate lines which are second-order shape functions calculated on the basis of the first-order shape functions.

Figure 17:
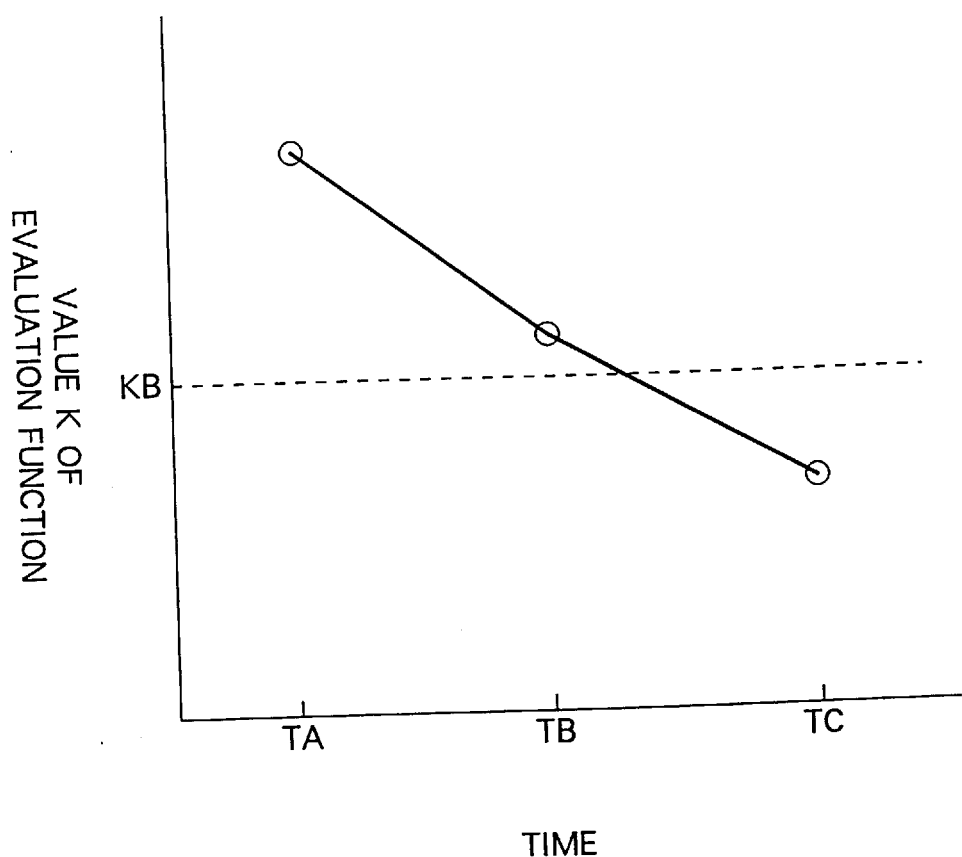
FIG. 17 is a graph for illustrating how an evaluation function employed by Embodiment 8 of the present invention varies with time.

FIG. 17 illustrates a change in the value K of the evaluation function that is the difference between the gradients of the two approximate lines which are obtained by the calculation based on the upper boundary shape function of FIG. 16.

In the case of performing the method employed in Embodiment 8 of the present invention, when the eye is opened or closed, the upper boundary shape function changes, similarly as in the case of the method employed in Embodiment 7 thereof. Thus, it can be detected whether the eye is opened or closed.

Embodiment 9

Figure 18:
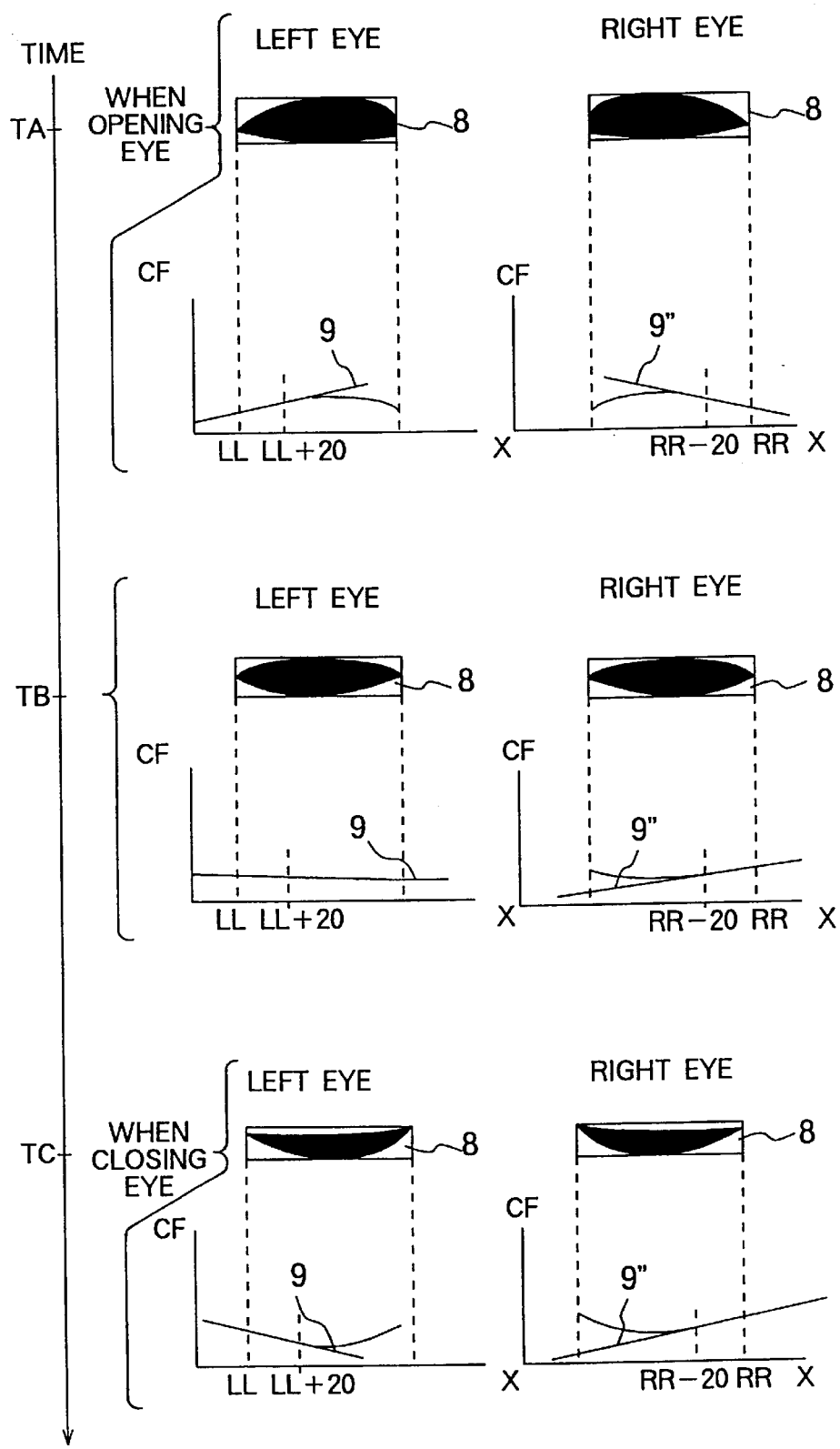
FIG. 18 is a diagram for illustrating a method for detecting the opened or closed condition of an eye, which is employed by Embodiment 9 of the present invention.

Next, Embodiment 9 of the present invention will be described hereinbelow by referring to FIGS. 18 and 19. FIG. 18 is a diagram for illustrating a method for detecting the opened or closed condition of an eye, which is employed by Embodiment 9 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and first-order shape functions (namely, Y-center-locus shape functions) respectively using the shape of what is called the Y-center-locus, and approximate lines which are second-order shape functions calculated from the first-order shape functions.

Figure 19:
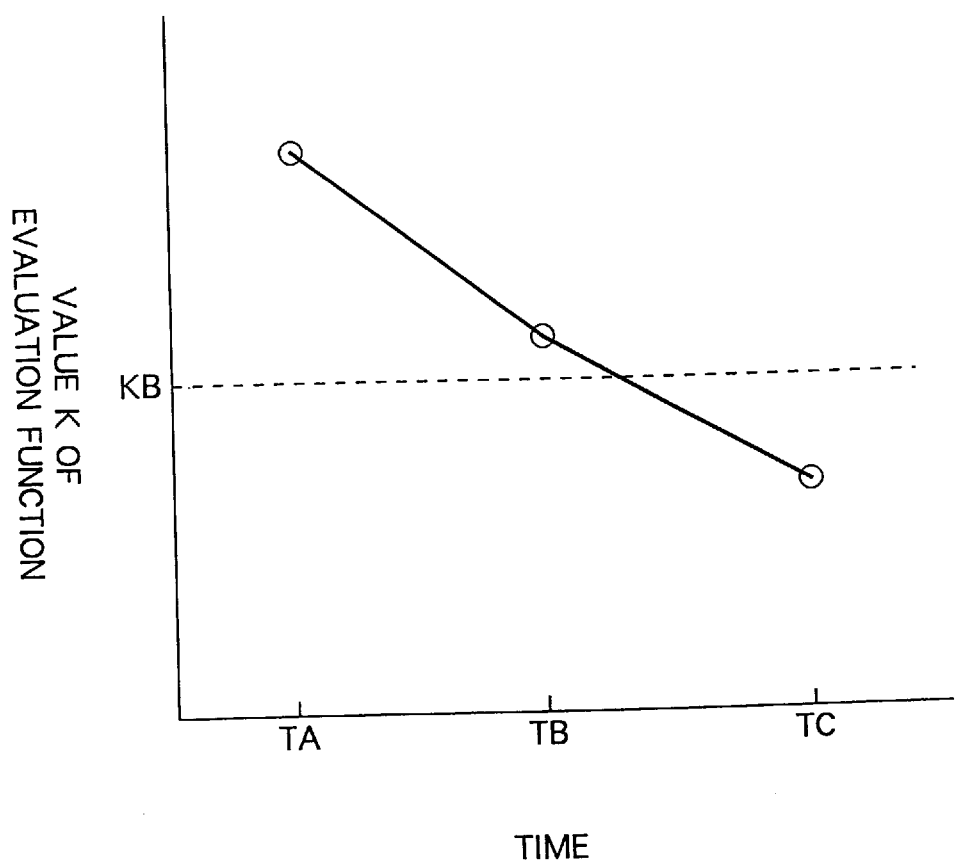
FIG. 19 is a graph for illustrating how an evaluation function employed by Embodiment 9 of the present invention varies with time.

FIG. 19 illustrates a change in the value K of the evaluation function that is the difference between the gradients of the two approximate lines which are obtained by the calculation based on the Y-center-locus shape functions of FIG. 18.

In the case of performing the method employed in Embodiment 9 of the present invention, when the eye is opened or closed, the Y-center-locus shape function changes, similarly as in the case of the method employed in Embodiment 7 thereof. Thus, it can be detected whether the eye is opened or closed.

Embodiment 10

Figure 20:
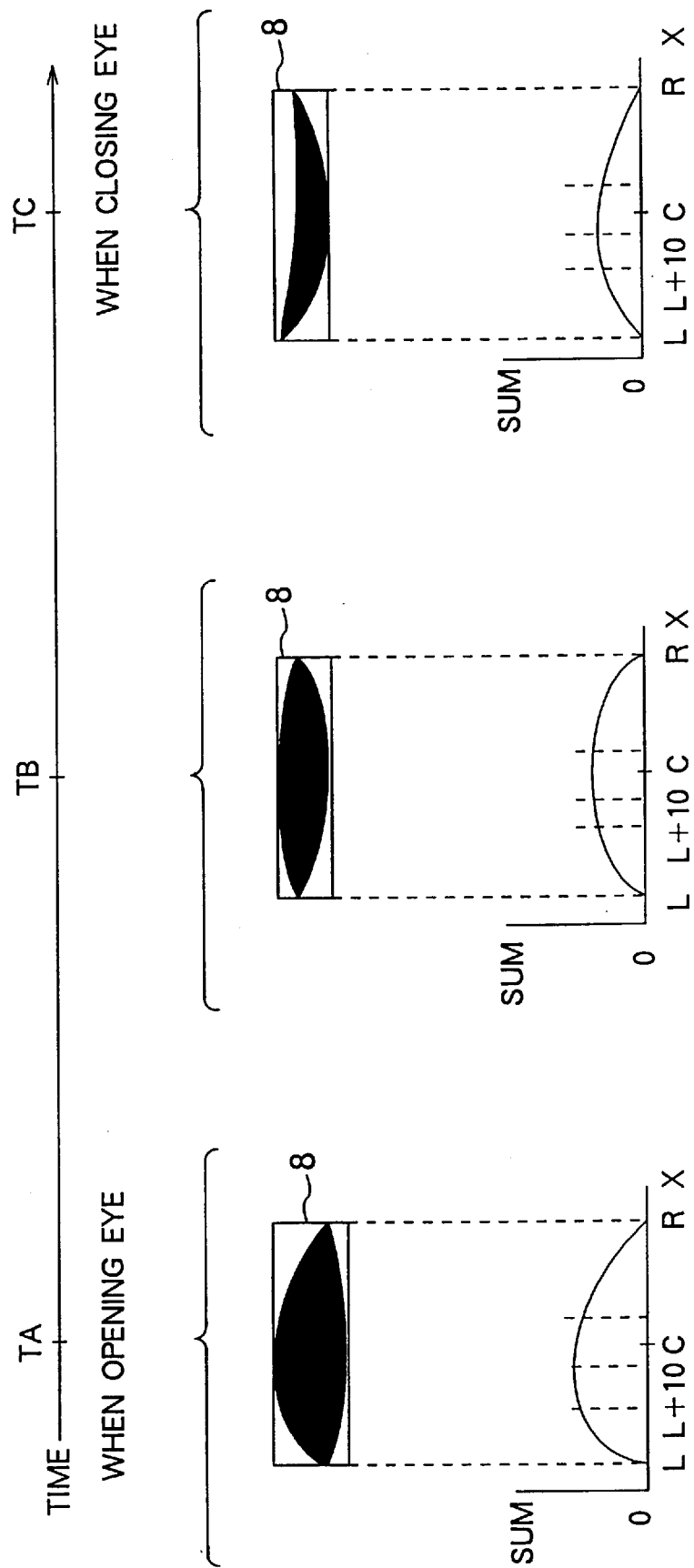
FIG. 20 is a diagram for illustrating a method for detecting the opened or closed condition of an eye, which is employed by Embodiment 10 of the present invention.

Next, Embodiment 10 of the present invention will be described hereinbelow by referring to FIGS. 20 and 21. FIG. 20 is a diagram for illustrating a method for detecting the opened or closed condition of an eye, which is employed by Embodiment 10 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and Y-histograms which are first-order shape functions corresponding to the binary images of the eye presence area 8.

Figure 21:
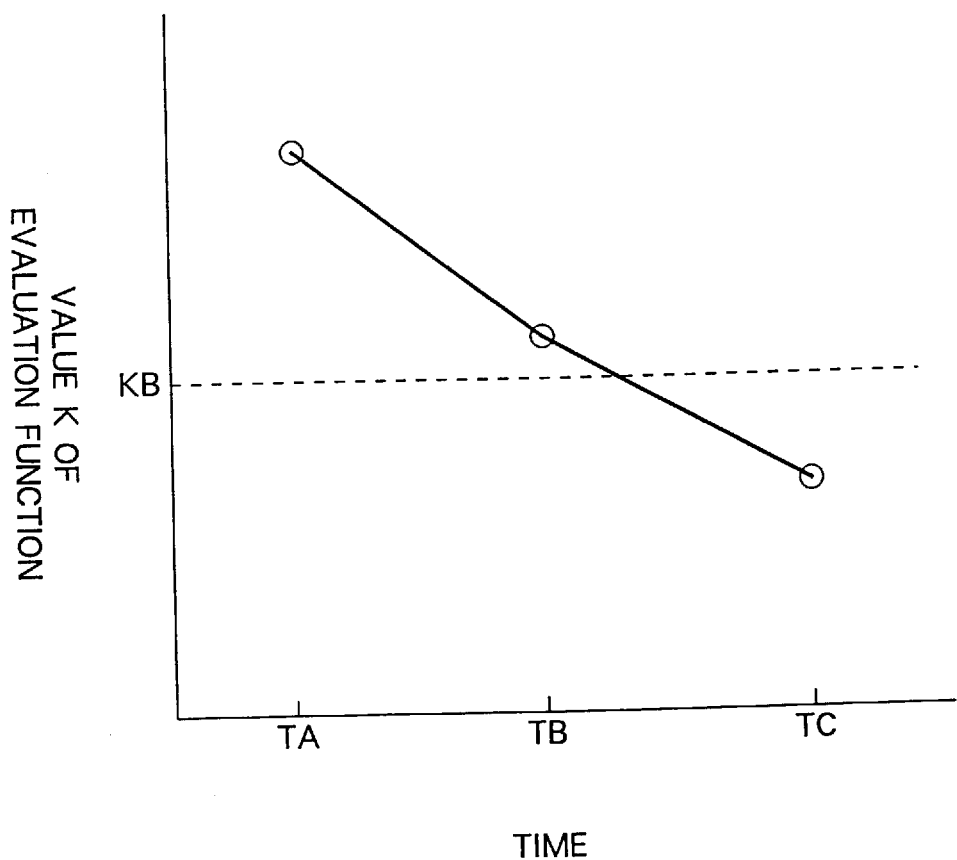
FIG. 21 is a graph for illustrating how an evaluation function employed by Embodiment 10 of the present invention varies with time.

FIG. 21 illustrates a change in the value K of the evaluation function, which is the difference between the two mean values or averages calculated on the basis of the Y-histograms of FIG. 20.

In the case of this Embodiment 10, the difference between the mean value or average of the counts (SUM) shown in a part of the Y-histograms, which corresponds to the central portion of the eye (namely, corresponds to the range of the X-coordinates of (C−5) to (C+5)), and that of the counts shown in another part of the Y-histograms, which corresponds to the left end portion of the eye (namely, corresponds to the range of X-coordinates of L to (L+10)) is the value K of the evaluation function given by the following equation (3). Incidentally, in the equation (3), each summation of the first half part or item of the left side thereof is performed with respect to X of (C−5) to (C+5) and each summation of the second half part or item of the right side thereof is performed with respect to X of L to (L+10).

$$K=(\Sigma SUM)/10-(\Sigma SUM)/10 \qquad (3)$$

As illustrated in FIG. 20, when the eye is opened or closed, the shape of the Y-histogram changes. As a result, when the eye is closed, the value K of the evaluation function is low. Thus, a threshold value KB is set, and it can be detected whether the eye is opened or closed.

Further, in the case of this embodiment, the mean value or average of the counts SUM shown in the part of the Y-histogram, which corresponds to the left end portion of the eye, is used for obtaining the evaluation function. However, similar effects are obtained in the case that the mean of the counts SUM shown in the part of the Y-histogram, which corresponds to the right end portion of the eye, is used for obtaining the evaluation function.

Embodiment 11

Figure 22:
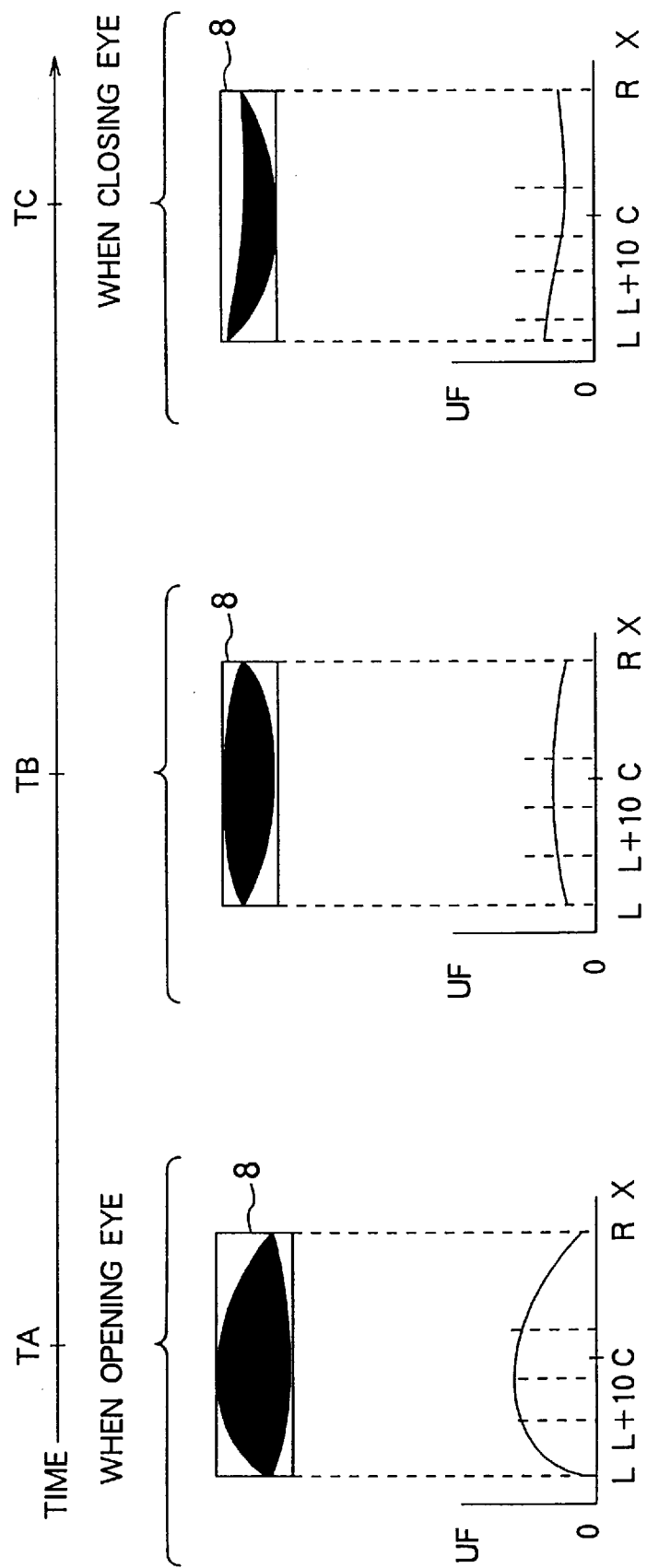
FIG. 22 is a diagram for illustrating a method for detecting the opened or closed condition of an eye, which is employed by Embodiment 11 of the present invention.

Next, Embodiment 11 of the present invention will be described hereinbelow by referring to FIGS. 22 and 23. FIG. 22 is a diagram for illustrating a method for detecting the opened or closed condition of an eye, which is employed by Embodiment 11 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, upper boundary shape functions) respectively using the coordinates of the upper boundaries of the binary images.

Figure 23:
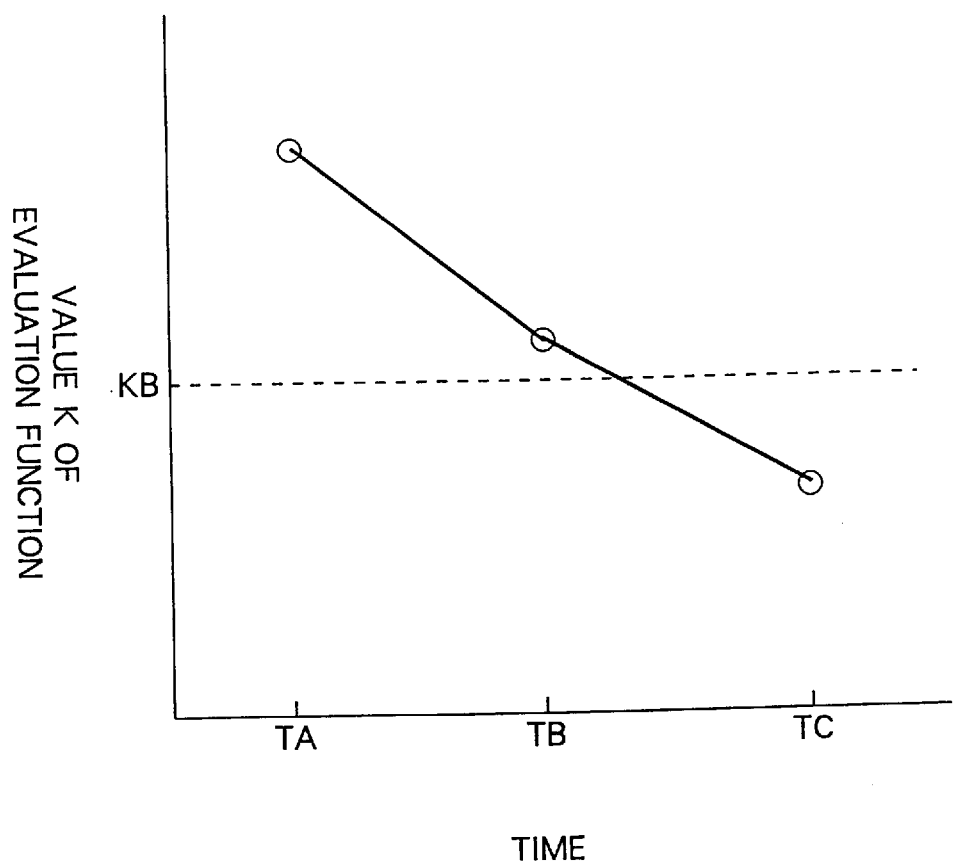
FIG. 23 is a graph for illustrating how an evaluation function employed by Embodiment 11 of the present invention varies with time.

FIG. 23 illustrates a change in the value K of the evaluation function that is the difference between the two means or averages which are obtained by the calculation based on the upper boundary shape function of FIG. 22.

In the case of performing the method employed in this Embodiment 11 of the present invention, when the eye is opened or closed, the upper boundary shape function changes, similarly as in the case of the method employed in Embodiment 10 thereof. Thus, it can be detected whether the eye is opened or closed.

Embodiment 12

Figure 24:
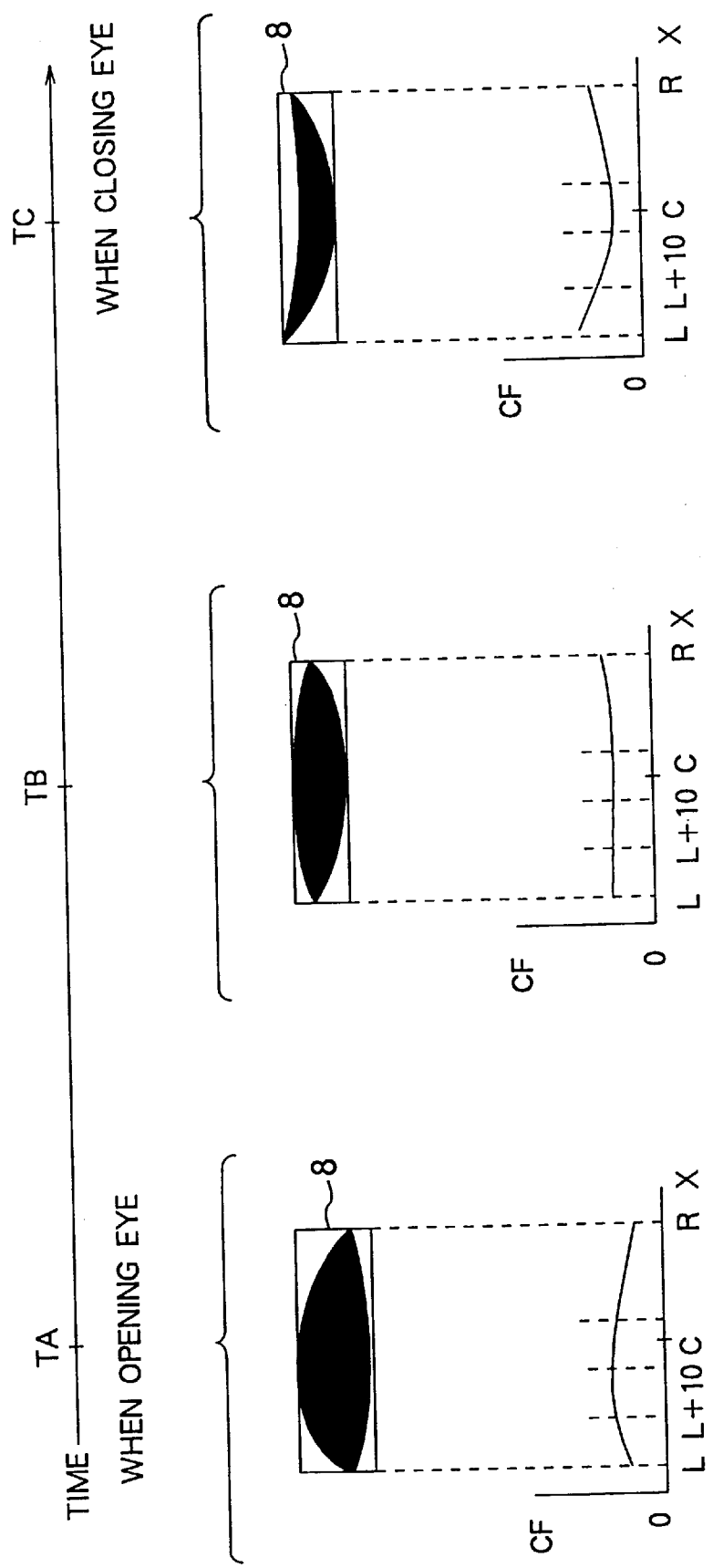
FIG. 24 is a diagram for illustrating a method for detecting the opened or closed condition of an eye, which is employed by Embodiment 12 of the present invention.

Next, Embodiment 12 of the present invention will be described hereinbelow by referring to FIGS. 24 and 25. FIG. 24 is a diagram for illustrating a method for detecting the opened or closed condition of an eye, which is employed by Embodiment 12 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, Y-center-locus shape functions) respectively using the shape of what is called the Y-center-locus.

Figure 25:
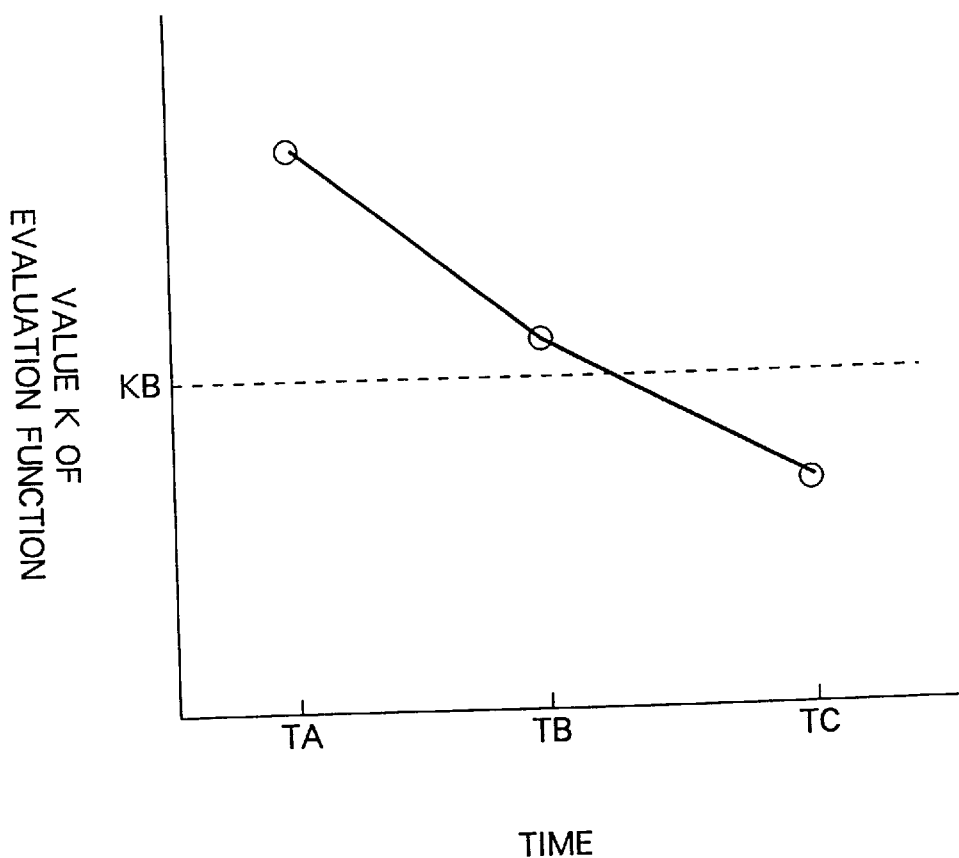
FIG. 25 is a graph for illustrating how an evaluation function employed by Embodiment 12 of the present invention varies with time.

FIG. 25 illustrates a change in the value K of the evaluation function that is the difference between the two means or average obtained by the calculation based on the Y-center-locus shape functions of FIG. 24.

In the case of performing the method employed in Embodiment 12 of the present invention, when the eye is opened or closed, the Y-center-locus shape function changes, similarly as in the case of the method employed in Embodiment 10 thereof. Thus, it can be detected whether the eye is opened or closed.

Embodiment 13

Figure 26:
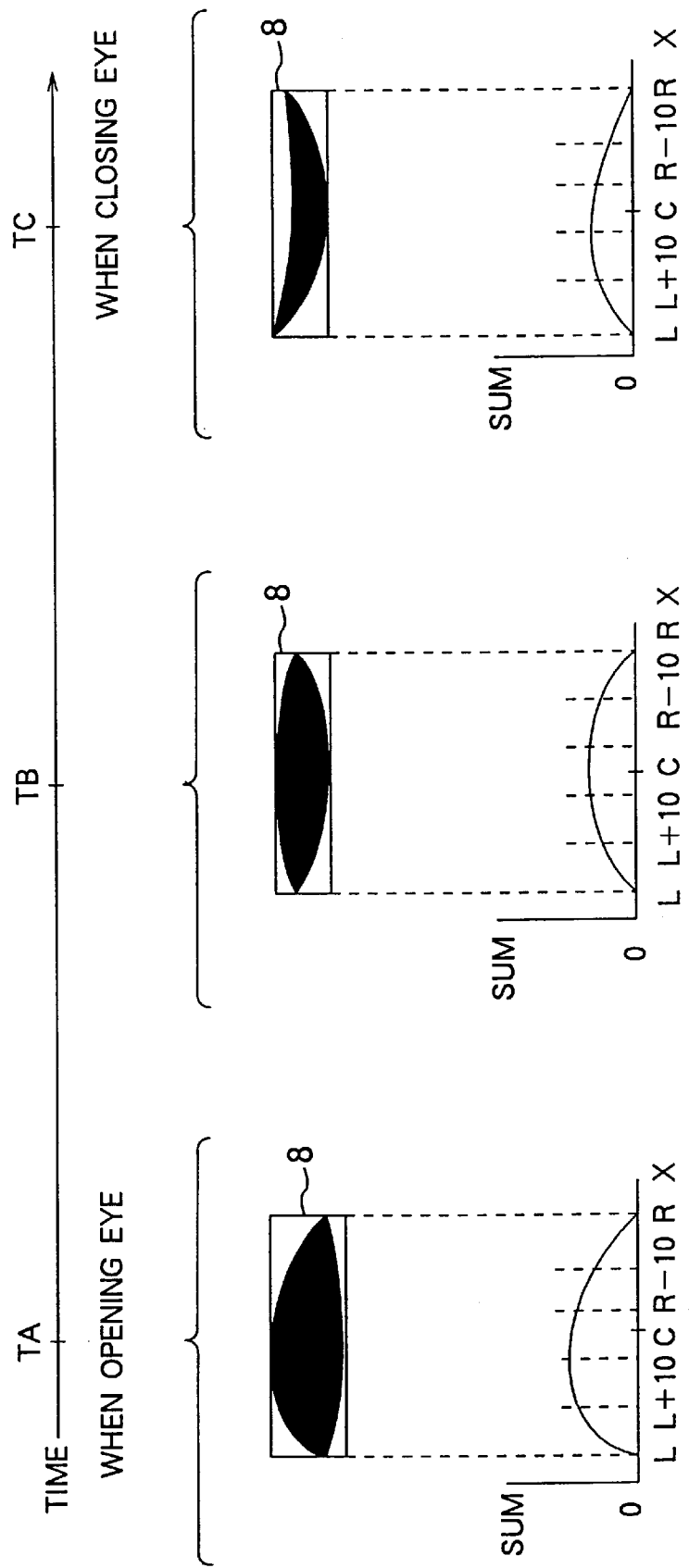
FIG. 26 is a diagram for illustrating a method for detecting the opened or closed condition of an eye, which is employed by Embodiment 13 of the present invention.

Next, Embodiment 13 of the present invention will be described hereinbelow by referring to FIGS. 26 and 27. FIG. 26 is a diagram for illustrating a method for detecting the opened or closed condition of an eye, which is employed by Embodiment 13 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and Y-histograms respectively corresponding to the binary images.

Figure 27:
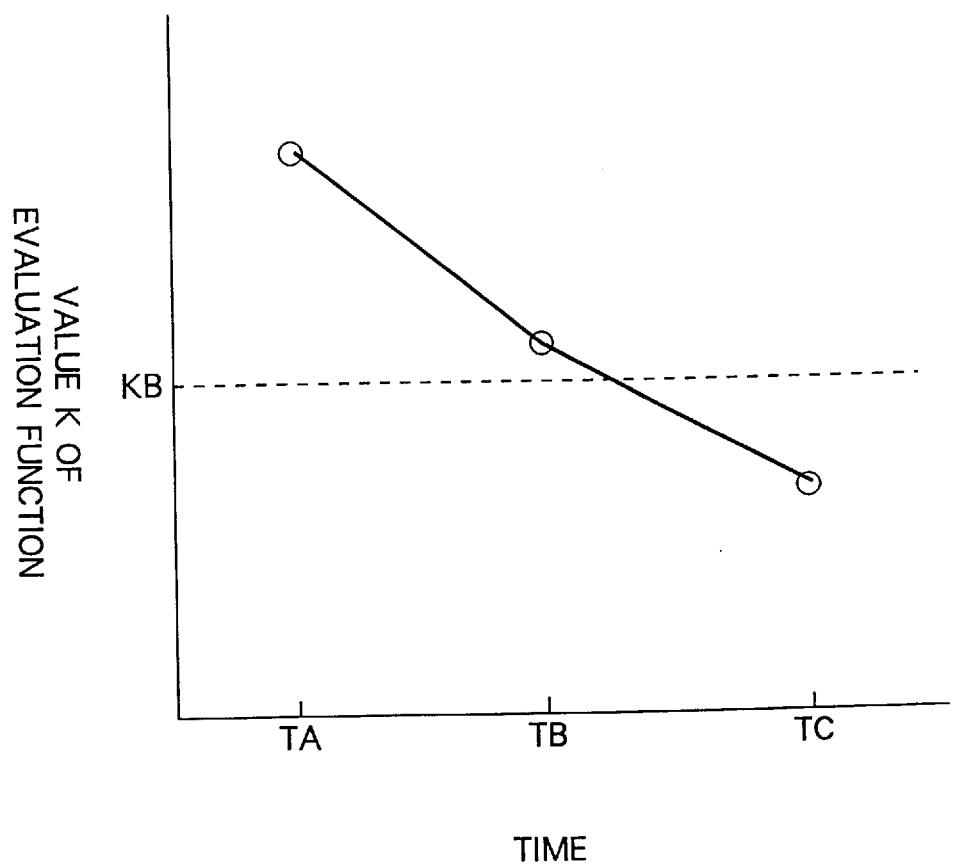
FIG. 27 is a graph for illustrating how an evaluation function employed by Embodiment 13 of the present invention varies with time.

FIG. 27 illustrates a change in the value K of the evaluation function, which is the difference between the two mean values or averages calculated on the basis of the Y-histograms of FIG. 26.

In the case of this Embodiment 13, the difference between the mean value or average of the counts (SUM) shown in a part of the Y-histograms, which corresponds to the central portion of the eye (namely, corresponds to the range of the X-coordinates of (C−5) to (C+5)), and that of the counts shown in other parts of the Y-histograms, which correspond to the left and right end portions of the eye (namely, correspond to the range of X-coordinates of L to (L+10) and the range of X-coordinates of (R−10) to R is the value K of the evaluation function given by the following equation (4). Incidentally, in the equation (4), the summation of the first item of the left side thereof is performed with respect to X of (C−5) to (C+5) and the second summation (namely, the left-side summation of the second item) of the right side thereof is performed with respect to X of L to (L+10), and the third summation (namely, the right-side summation of the second item) of the right side thereof is performed with respect to X of (R−10) to R.

$$K=(\Sigma SUM)/10-(\Sigma SUM+\Sigma SUM)/20 \qquad (4)$$

As illustrated in FIG. 26, when the eye is opened or closed, the shape of the Y-histogram changes. As a result, when the eye is closed, the value K of the evaluation function is low, as shown in FIG. 27. Thus, a threshold value KB is set, and it can be detected whether the eye is opened or closed.

Embodiment 14

Figure 28:
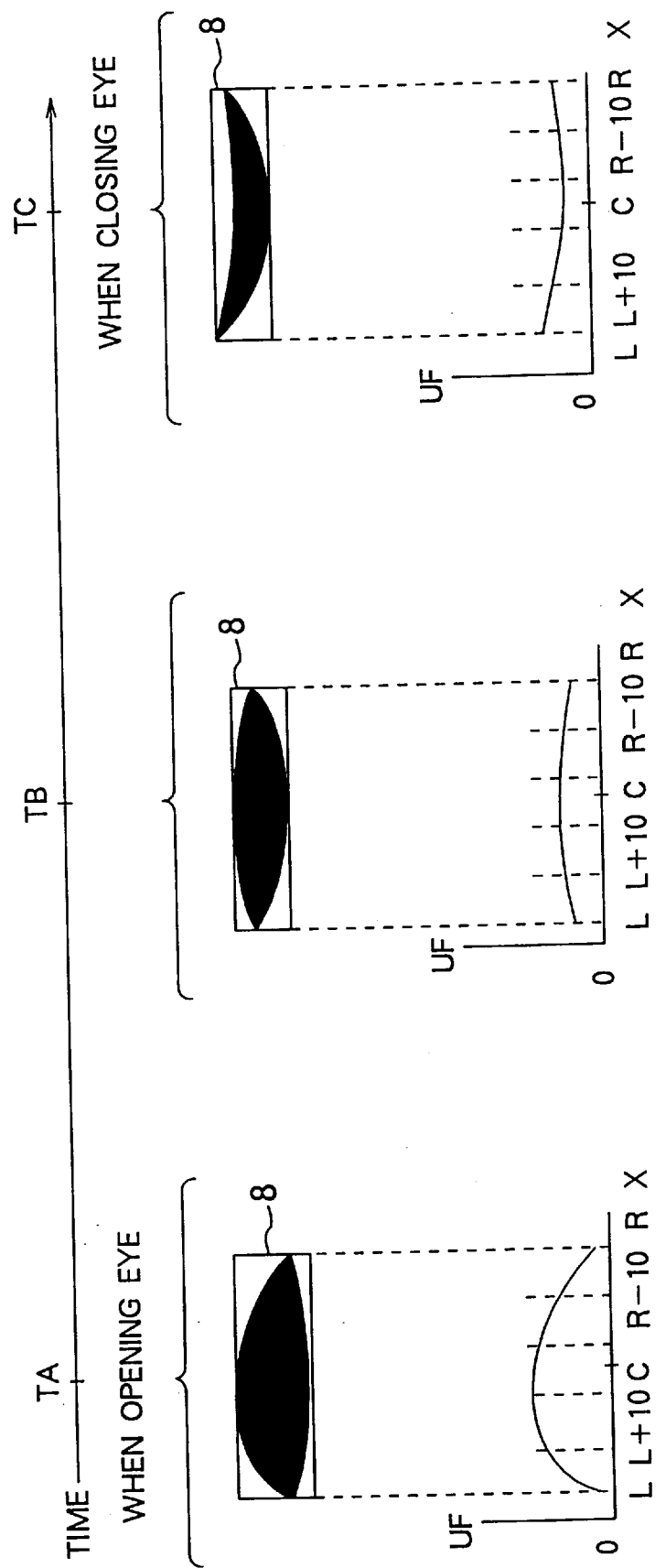
FIG. 28 is a diagram for illustrating a method for detecting the opened or closed condition of an eye, which is employed by Embodiment 14 of the present invention.
Figure 29:
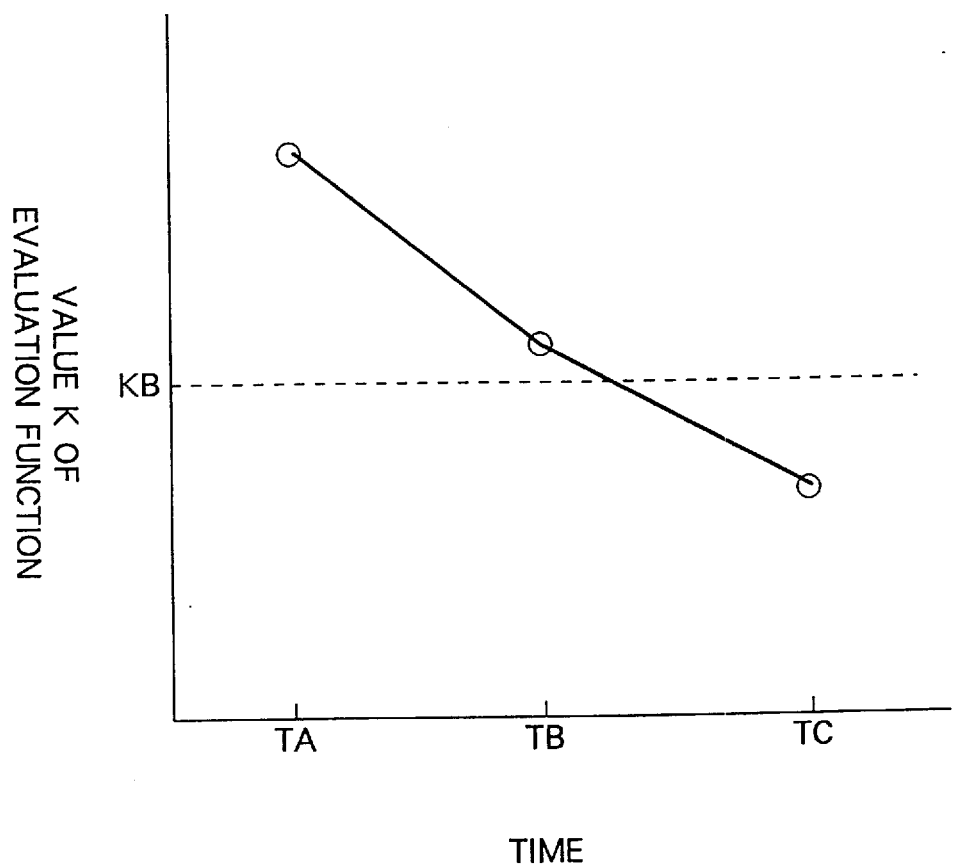
FIG. 29 is a graph for illustrating how an evaluation function employed by Embodiment 14 of the present invention varies with time.

Next, Embodiment 14 of the present invention will be described hereinbelow by referring to FIGS. 28 and 29. FIG. 28 is a diagram for illustrating a method for detecting the opened or closed condition of an eye, which is employed by Embodiment 14 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, upper boundary shape functions) respectively using the coordinates of the upper boundaries of the binary images FIG. 29 illustrates a change in the value K of the evaluation function that is the difference between the two mean values or averages which are obtained by the calculation based on the upper boundary shape function of FIG. 28.

In the case of performing the method employed in this Embodiment 14 of the present invention, when the eye is opened or closed, the upper boundary shape function changes, similarly as in the case of the method employed in Embodiment 13 thereof. Thus, it can be detected whether the eye is opened or closed.

Embodiment 15

Figure 30:
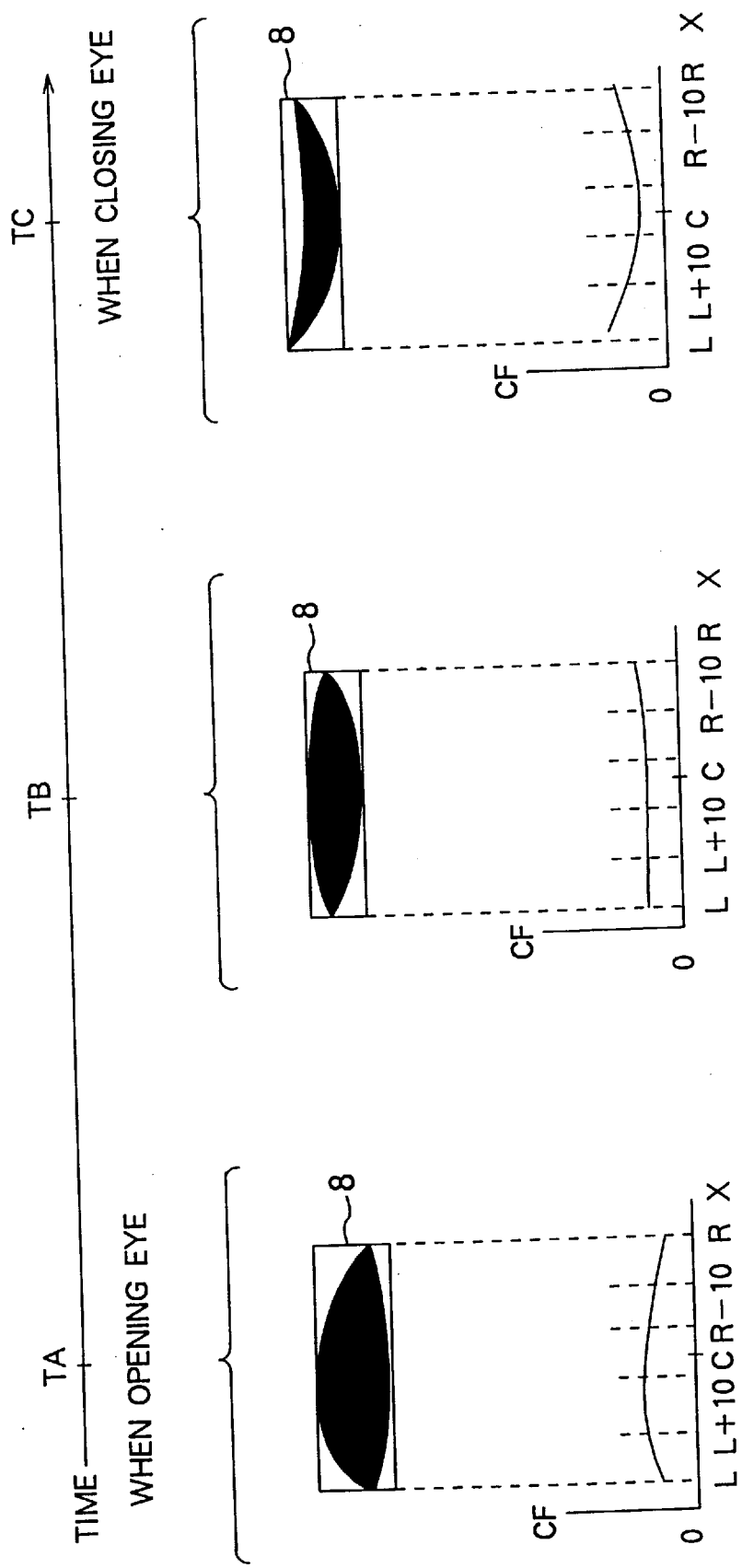
FIG. 30 is a diagram for illustrating a method for detecting the opened or closed condition of an eye, which is employed by Embodiment 15 of the present invention.

Next, Embodiment 15 of the present invention will be described hereinbelow by referring to FIGS. 30 and 31. FIG. 30 is a diagram for illustrating a method for detecting the opened or closed condition of an eye, which is employed by Embodiment 15 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, Y-center-locus shape functions) respectively using the shape of what is called the Y-center-locus.

Figure 31:
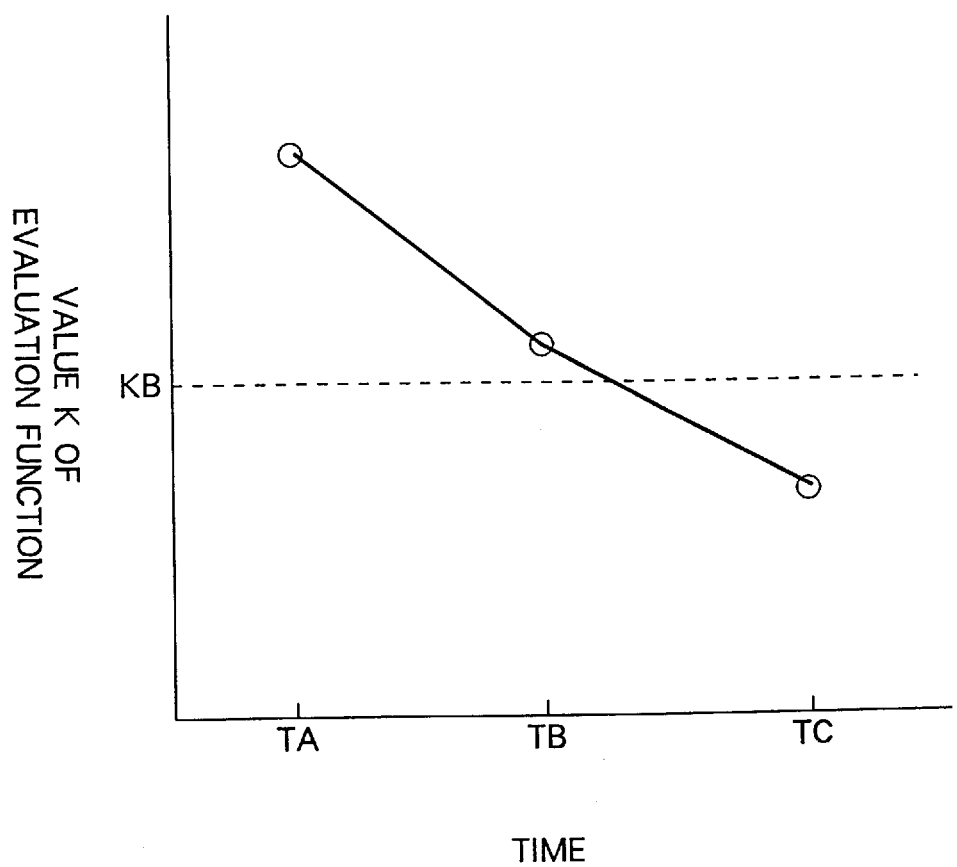
FIG. 31 is a graph for illustrating how an evaluation function employed by Embodiment 15 of the present invention varies with time.

FIG. 31 illustrates a change in the value K of the evaluation function that is the difference between the two mean values or averages obtained by the calculation based on the Y-center-locus shape functions of FIG. 30.

In the case of performing the method employed in Embodiment 15 of the present invention, when the eye is opened or closed, the Y-center-locus shape function changes, similarly as in the case of the method employed in Embodiment 13 thereof. Thus, it can be detected whether the eye is opened or closed.

Embodiment 16

Figure 32:
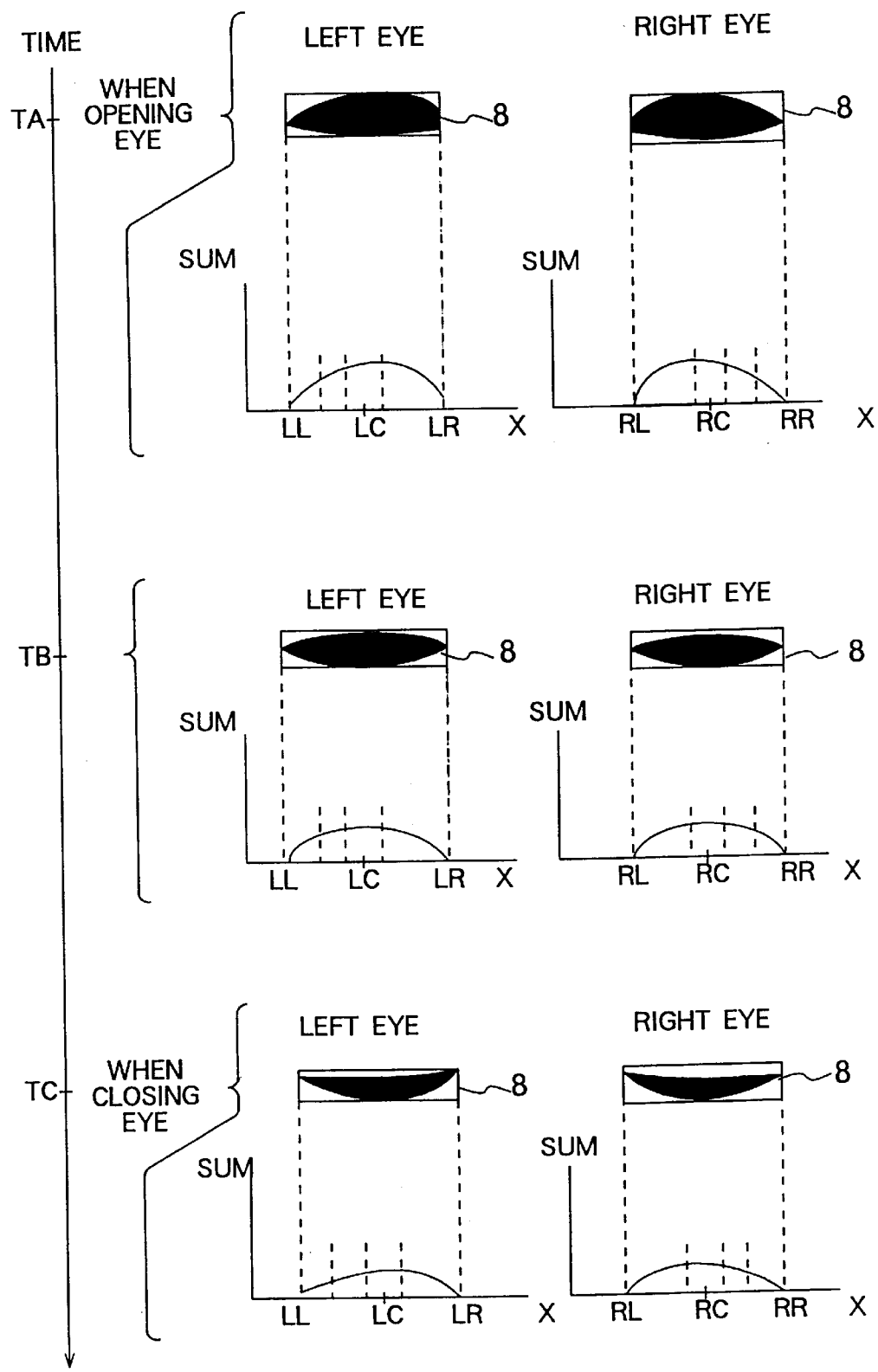
FIG. 32 is a diagram for illustrating a method for detecting the opened or closed condition of an eye, which is employed by Embodiment 16 of the present invention.

Next, Embodiment 16 of the present invention will be described hereinbelow by referring to FIGS. 32 and 33. FIG. 32 is a diagram for illustrating a method for detecting the opened or closed condition of an eye, which is employed by Embodiment 16 of the present invention. This diagram illustrates the relation among the lapse of time (from a moment TA, at which the eye is opened, to another moment TC, at which the eye is closed, through an intermediate moment TB therebetween), the binary images of the eye presence area 8 varying with the lapse of time, and Y-histograms respectively corresponding to the binary images.

Figure 33:
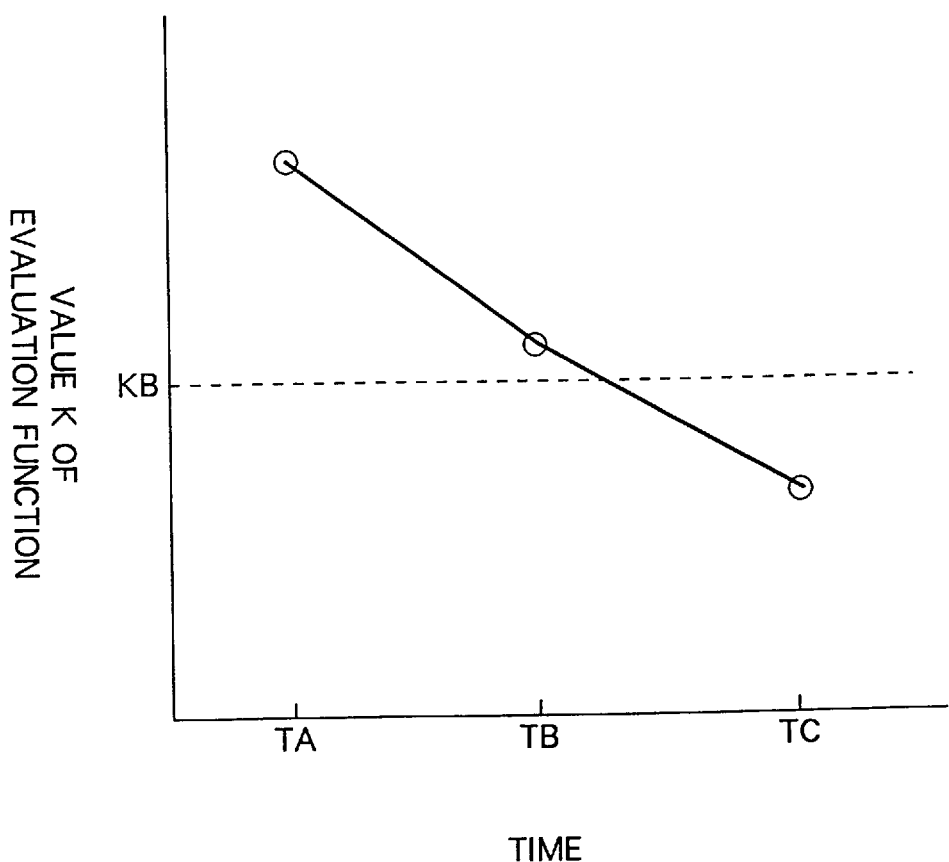
FIG. 33 is a graph for illustrating how an evaluation function employed by Embodiment 16 of the present invention varies with time.

FIG. 33 illustrates a change in the value K of the evaluation function, which is the difference between the two mean values or averages calculated on the basis of the Y-histograms of FIG. 32.

In the case of this Embodiment 16, the difference between the mean value or average of the counts (SUM) shown in two parts of the Y-histograms, which respectively correspond to the central portions of the left and right eyes (namely, corresponds to the ranges of the X-coordinates of ((LC−5) to (LC+5) and (RC−5) to (RC+5)), and that of the counts shown in other two parts of the Y-histograms, which correspond to the outer end portions (namely, the left and right end portions) of both of the eyes (namely, correspond to the ranges of X-coordinates of LL to (LL+10) and the range of X-coordinates of (RR−10) to RR) is the value K of the evaluation function given by the following equation (5). Incidentally, in the equation (5), the first or left-side summation of the first item of the left side thereof is performed with respect to X of (LC−5) to (LC+5) and the second or right-side summation of the first item of the left side thereof is performed with respect to X of (RC−5) to (RC+5) and the third summation (namely, the left-side summation of the second item) of the right side thereof is performed with respect to X of LL to (LL+10), and the fourth summation (namely, the right-side summation of the second item) of the right side thereof is performed with respect to X of (RR−10) to RR.

$$K = (\Sigma SUM + \Sigma SUM)/20 - (\Sigma SUM + \Sigma SUM)/20 \qquad (5)$$

As illustrated in FIG. 32, when the eye is opened or closed, the shape of the Y-histogram changes. As a result, when the eye is closed, the value K of the evaluation function is low, as shown in FIG. 33. Thus, a threshold value is set at KB, and it can be detected whether the eye is opened or closed.

Further, in the case of this embodiment, the average of the counts shown in the Y-histogram of the predetermined range corresponding to the outer end portions of both eyes is used for obtaining the value of the evaluation function. However, similar effects can be obtained in the case that the average of the counts shown in the Y-histogram of the predetermined range corresponding to the inner end portions of both eyes is used.

Embodiment 17

Figure 34:
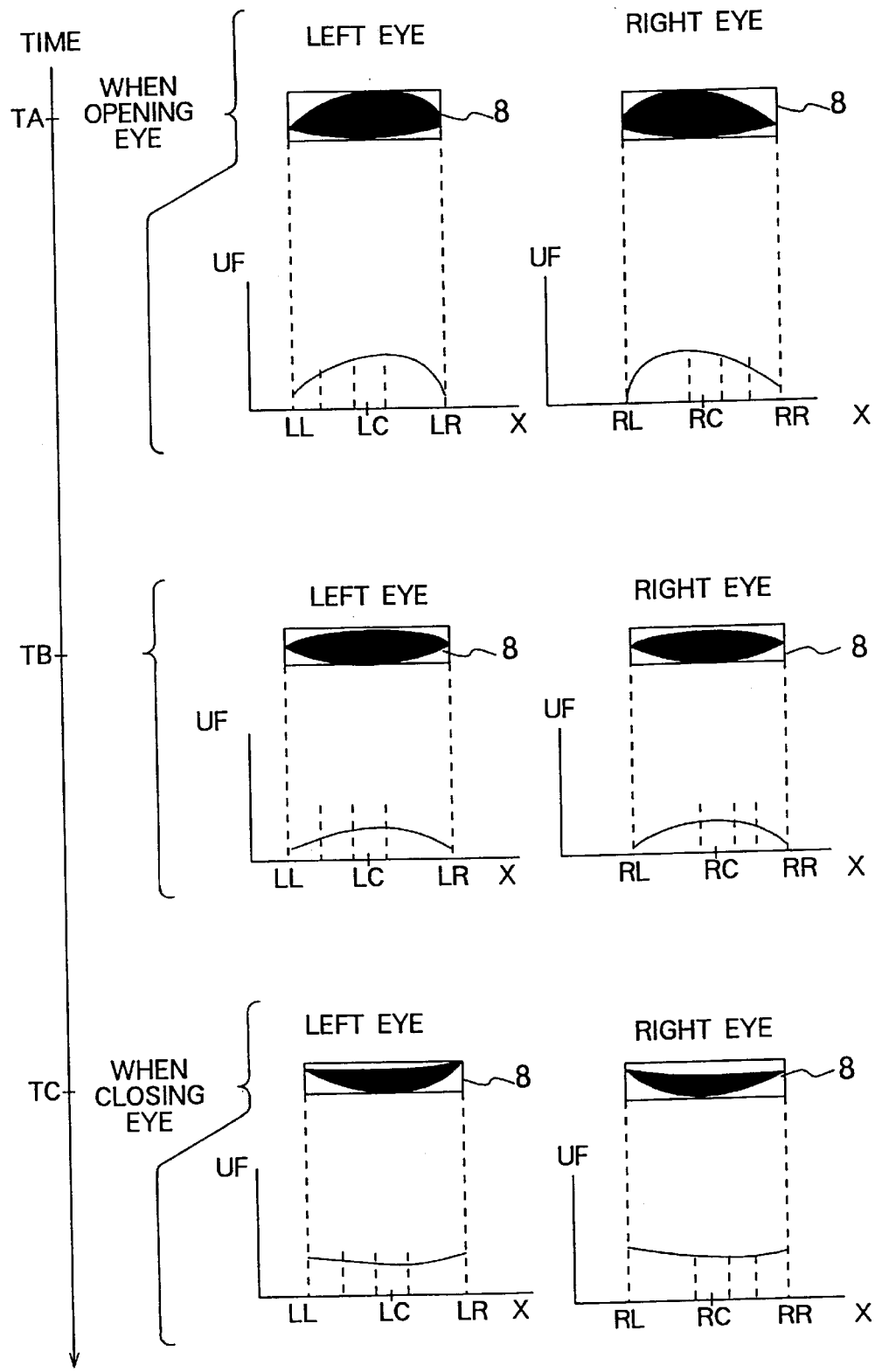
FIG. 34 is a diagram for illustrating a method for detecting the opened or closed condition of an eye, which is employed by Embodiment 17 of the present invention.

Next, Embodiment 17 of the present invention will be described hereinbelow by referring to FIGS. 34 and 35. FIG. 34 is a diagram for illustrating a method for detecting the opened or closed condition of an eye, which is employed by Embodiment 14 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, upper boundary shape functions) respectively using the coordinates of the upper boundaries of the binary images.

Figure 35:
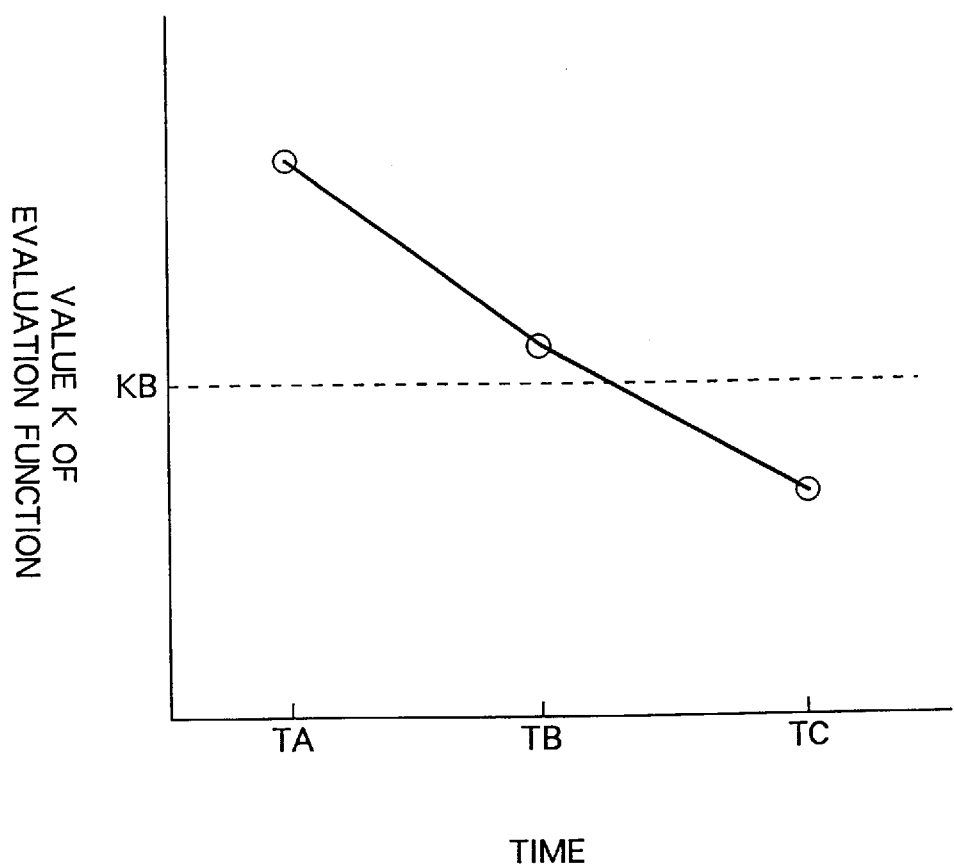
FIG. 35 is a graph for illustrating how an evaluation function employed by Embodiment 17 of the present invention varies with time.

FIG. 35 illustrates a change in the value K of the evaluation function that is the difference between the two mean values or averages which are obtained by the calculation based on the upper boundary shape function of FIG. 34.

In the case of performing the method employed in this Embodiment 17 of the present invention, when the eye is opened or closed, the upper boundary shape function changes, similarly as in the case of the method employed in Embodiment 16 thereof. Thus, it can be detected whether the eye is opened or closed.

Embodiment 18

Figure 36:
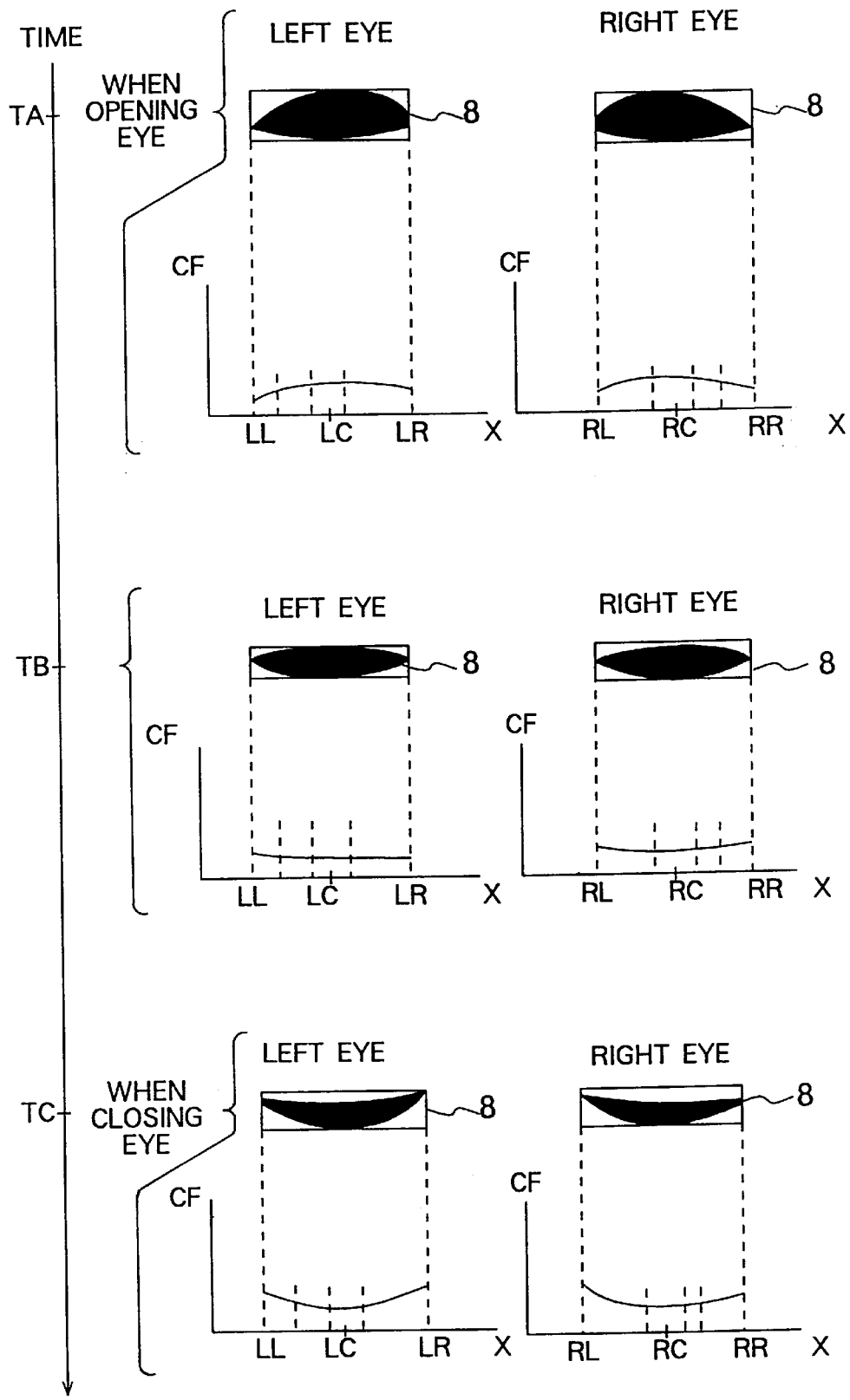
FIG. 36 is a diagram for illustrating a method for detecting the opened or closed condition of an eye, which is employed by Embodiment 18 of the present invention.

Next, Embodiment 18 of the present invention will be described hereinbelow by referring to FIGS. 36 and 37. FIG. 36 is a diagram for illustrating a method for detecting the opened or closed condition of an eye, which is employed by Embodiment 18 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and shape functions (namely, Y-center-locus shape functions) respectively using the shape of what is called the Y-center-locus.

Figure 37:
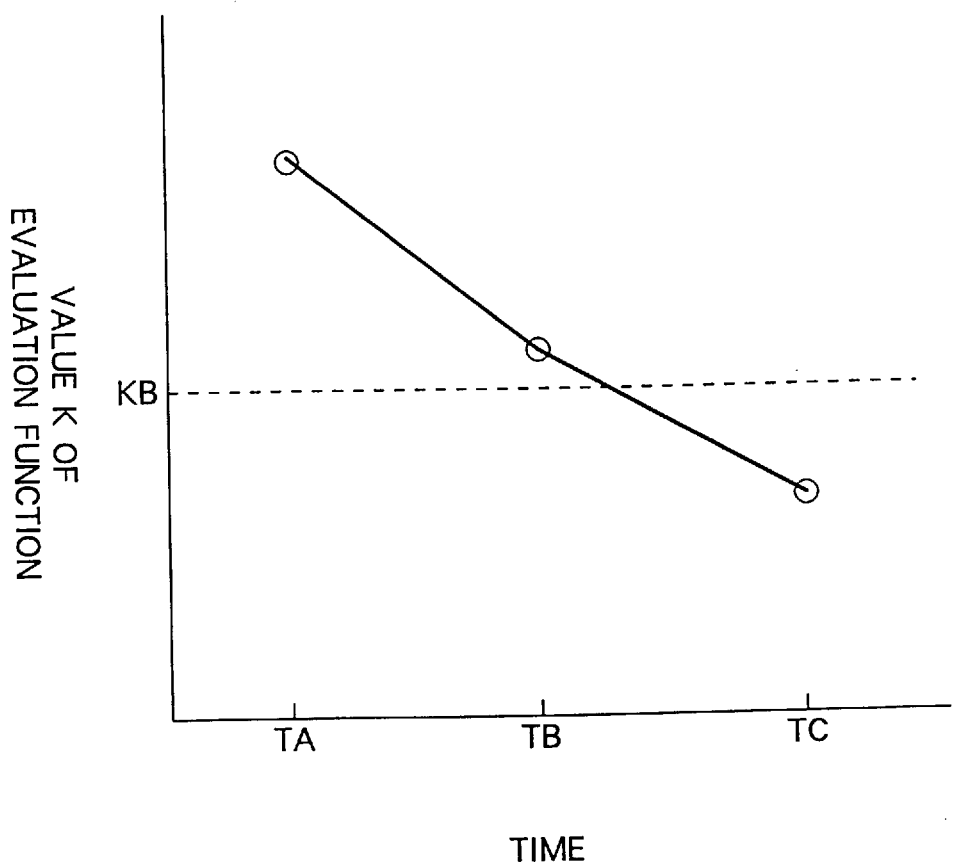
FIG. 37 is a graph for illustrating how an evaluation function employed by Embodiment 18 of the present invention varies with time.

FIG. 37 illustrates a change in the value K of the evaluation function that is the difference between the two mean values or averages obtained by the calculation based on the Y-center-locus shape functions of FIG. 36.

In the case of performing the method employed in Embodiment 18 of the present invention, when the eye is opened or closed, the Y-center-locus shape function changes, similarly as in the case of the method employed in Embodiment 16 thereof. Thus, it can be detected whether the eye is opened or closed.

Embodiment 19

Figure 38:
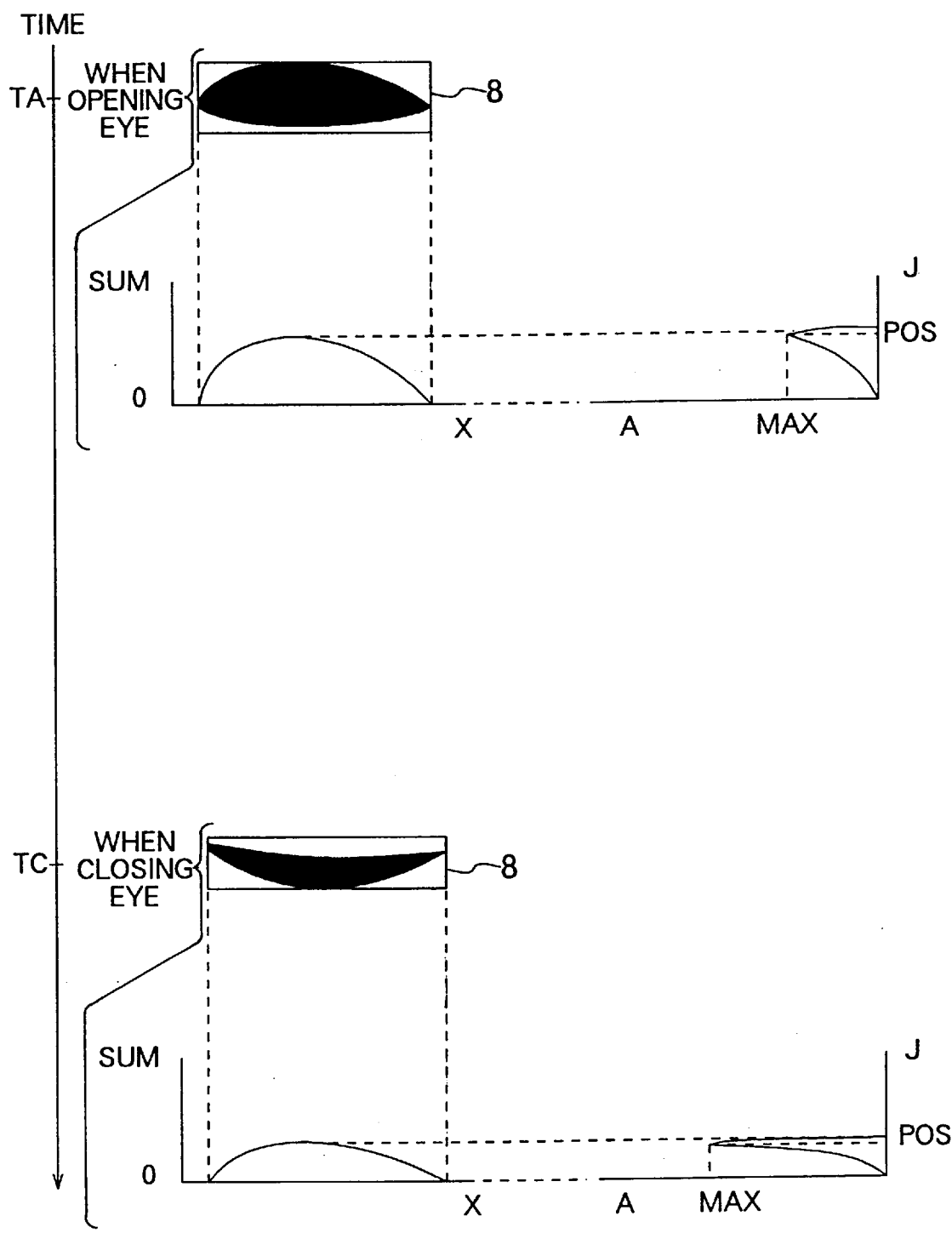
FIG. 38 is a diagram for illustrating a method for detecting the opened or closed condition of an eye, which is employed by Embodiment 19 of the present invention.

Next, Embodiment 19 of the present invention will be described hereinbelow by referring to FIGS. 38 and 39. FIG. 38 is a diagram for illustrating a method for detecting the opened or closed condition of an eye, which is employed by Embodiment 19 of the present invention. This diagram illustrates the relation among the lapse of time (from a moment TA, at which the eye is opened, to another moment TC, at which the eye is closed), the binary images of the eye presence area 8 varying with the lapse of time, and Y-histograms which are first-order shape functions corresponding to the binary images of the eye presence area 8, and frequency distribution curves which are second-order shape functions calculated on the basis of the first-order shape functions and represent the frequency distributions A of the counts (SUM), respectively.

Figure 39:
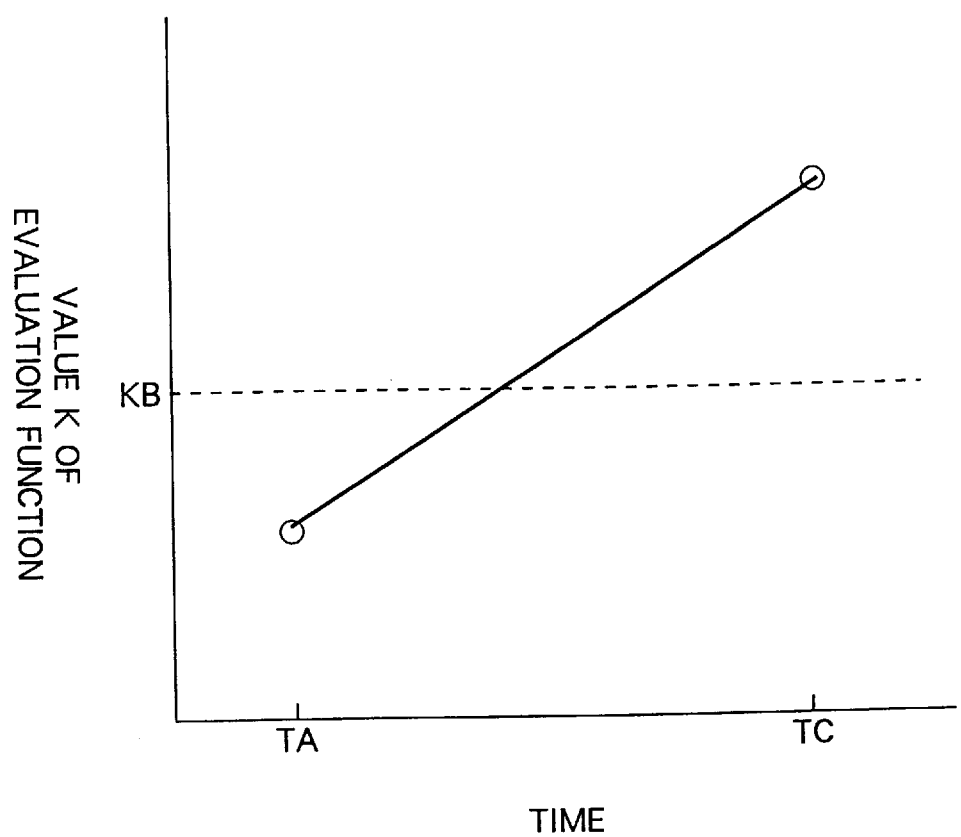
FIG. 39 is a graph for illustrating how an evaluation function employed by Embodiment 19 of the present invention varies with time.

FIG. 39 illustrates a change in the value K of the evaluation function, which is obtained by performing calculations on the basis of the frequency distribution curves of FIG. 38.

Further, in the case of this Embodiment 19, the value K of the evaluation function is obtained by the following equation (6) where "MAX" represents the maximum value of the cumulative frequency shown in the frequency distribution curves and "POS" denotes the value of the exponent J at the time when the cumulative frequency has the maximum value "MAX". This value K indicates the degree of centralization of the Y-histogram. Incidentally, in the equation (6), the summation in the right side thereof is performed with respect to the cumulative frequency (namely, the count) of 0 to maximum value.

$$K = MAX/\Sigma\{A^{(POS-J)}\} \qquad (6)$$

As illustrated in FIG. 38, when the eye is opened or closed, the shape of the frequency distribution curve changes. As a result, as illustrated in FIG. 39, when the eye is closed, the value K of the evaluation function is high. Thus, a threshold value is set at KB, and it can be detected whether the eye is opened or closed.

Embodiment 20

Figure 40:
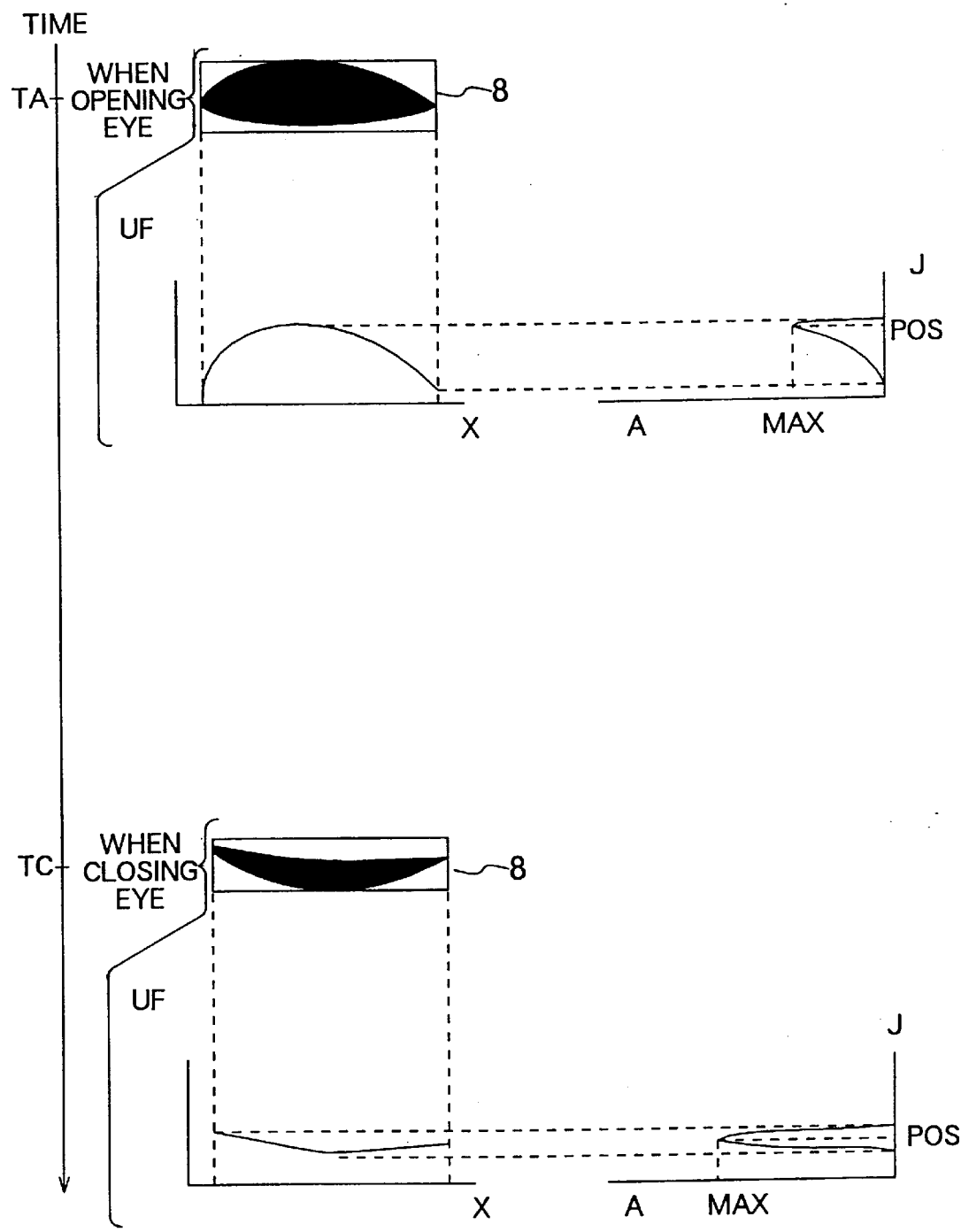
FIG. 40 is a diagram for illustrating a method for detecting the opened or closed condition of an eye, which is employed by Embodiment 20 of the present invention.

Next, Embodiment 20 of the present invention will be described hereinbelow by referring to FIGS. 40 and 41. FIG. 40 is a diagram for illustrating a method for detecting the opened or closed condition of an eye, which is employed by Embodiment 20 of the present invention. This diagram illustrates the relation among the lapse of time (from a moment TA, at which the eye is opened, to another moment TC, at which the eye is closed), the binary images of the eye presence area 8 varying with the lapse of time, and first-order shape functions (namely, the upper boundary shape functions) using the (Y-)coordinates of the upper boundaries of the binary images of the eye presence area 8, and frequency distribution curves which are second-order shape functions calculated on the basis of the first-order shape functions and represent the frequency distributions A of the values (UF) of the upper boundary functions, respectively.

Figure 41:
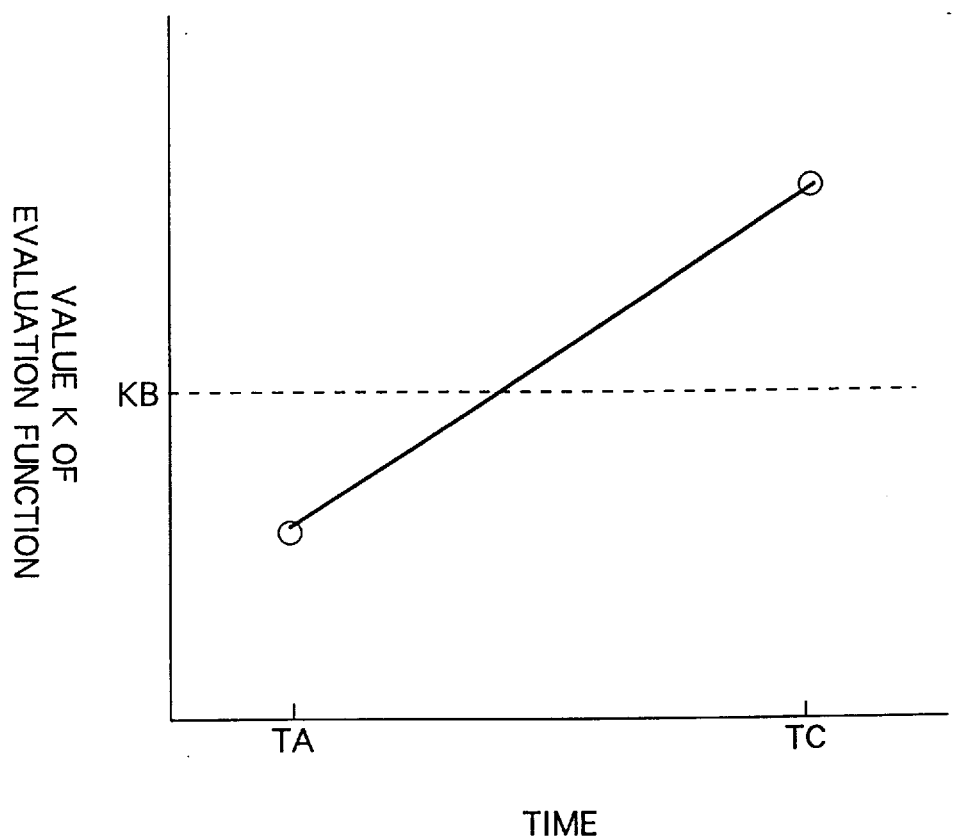
FIG. 41 is a graph for illustrating how an evaluation function employed by Embodiment 20 of the present invention varies with time.

FIG. 41 illustrates a change in the value K of the evaluation function, which is obtained by performing calculations on the basis of the frequency distribution curves of FIG. 40.

Further, in the case of the method employed in this Embodiment 20, when the eye is opened or closed, the shape of the frequency distribution curve changes, similarly as in the case of the aforementioned Embodiment 19. Thus, it can be detected whether the eye is opened or closed.

Embodiment 21

Figure 42:
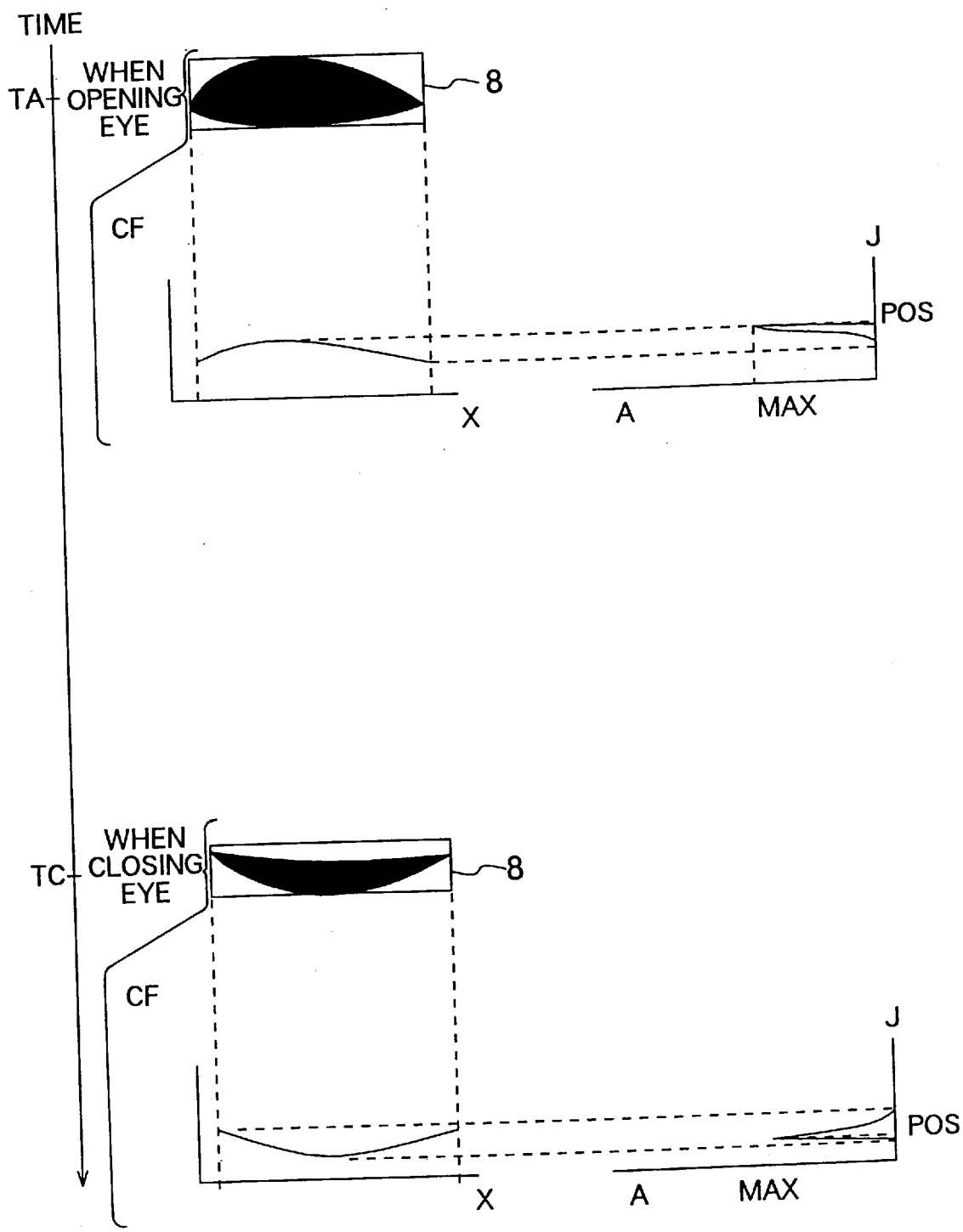
FIG. 42 is a diagram for illustrating a method for detecting the opened or closed condition of an eye, which is employed by Embodiment 21 of the present invention.

Next, Embodiment 21 of the present invention will be described hereinbelow by referring to FIGS. 42 and 43. FIG. 42 is a diagram for illustrating a method for detecting the opened or closed condition of an eye, which is employed by this Embodiment 21 of the present invention. This diagram illustrates the relation among the lapse of time (from a moment TA, at which the eye is opened, to another moment TC, at which the eye is closed), the binary images of the eye presence area 8 varying with the lapse of time, and first-order shape functions (namely, the Y-center-locus shape functions) using the shape of the Y-center lines (or curves) of the binary images, and frequency distribution curves which are second-order shape functions calculated on the basis of the first-order shape functions and represent the frequency distributions A of the values (CF) of the Y-center-locus shape functions, respectively.

Figure 43:
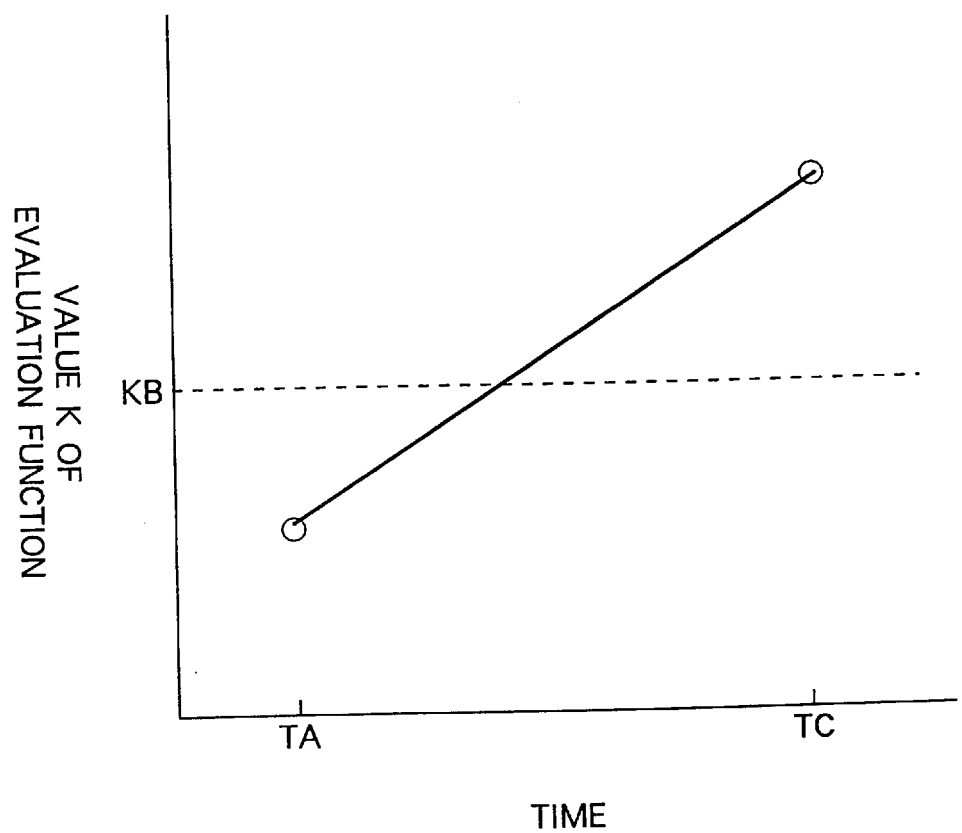
FIG. 43 is a graph for illustrating how an evaluation function employed by Embodiment 21 of the present invention varies with time.

FIG. 43 illustrates a change in the value K of the evaluation function, which is obtained by performing calculations on the basis of the frequency distribution curves of FIG. 42.

Further, in the case of the method employed in this Embodiment 21, when the eye is opened or closed, the shape of the frequency distribution curve changes, similarly as in the case of the aforementioned Embodiment 19. Thus, it can be detected whether the eye is opened or closed.

Embodiment 22

Figure 44:
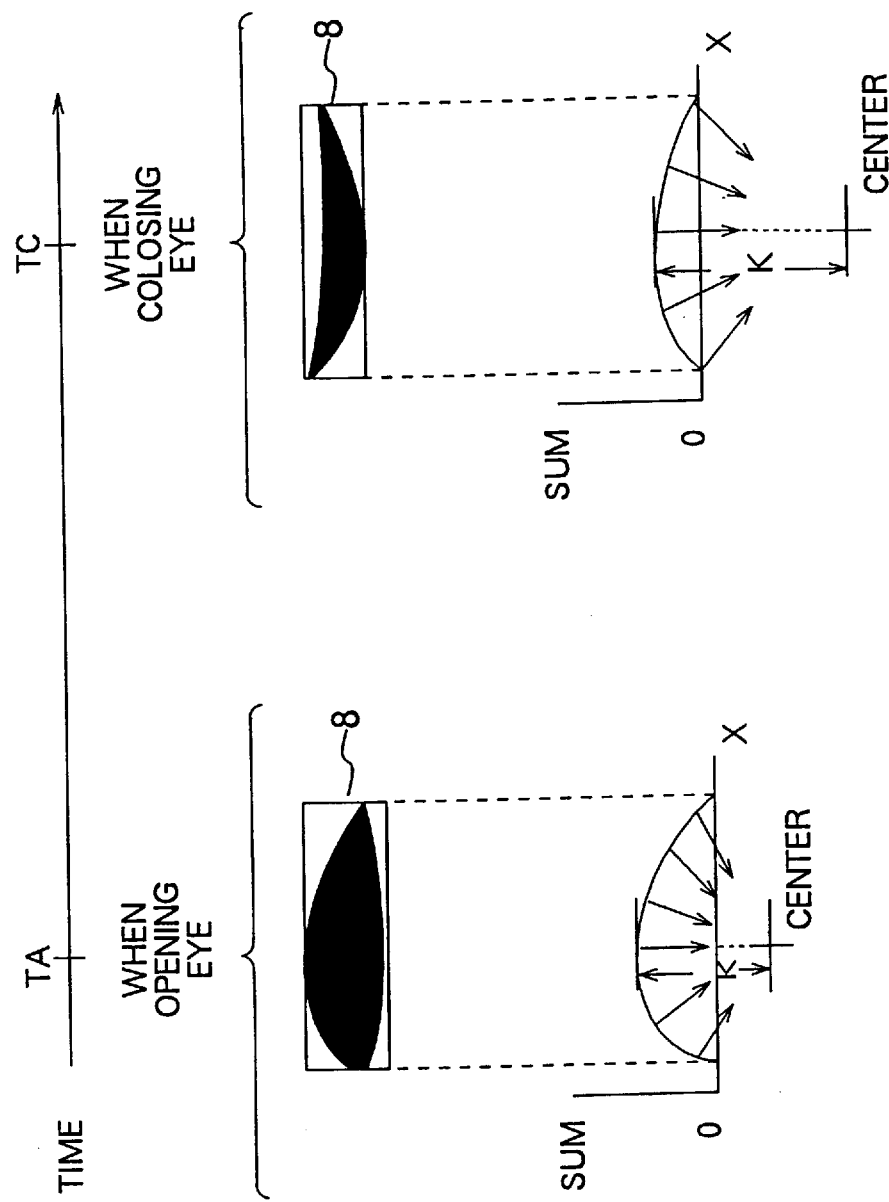
FIG. 44 is a diagram for illustrating a method for detecting the opened or closed condition of an eye, which is employed by Embodiment 22 of the present invention.

Next, Embodiment 22 of the present invention will be described hereinbelow by referring to FIGS. 44 and 45. FIG. 44 is a diagram for illustrating a method for detecting the opened or closed condition of an eye, which is employed by this Embodiment 22 of the present invention. This diagram illustrates the relation among the lapse of time (from a moment TA, at which the eye is opened, to another moment TC, at which the eye is closed), the binary images of the eye presence area 8 varying with the lapse of time, and Y-histograms (namely, first-order shape functions) of the binary images, and the centers of circles which are second-order shape functions obtained on the basis of the arcuate shapes of the first-order shape functions by using what is called a spoke filter.

Figure 45:
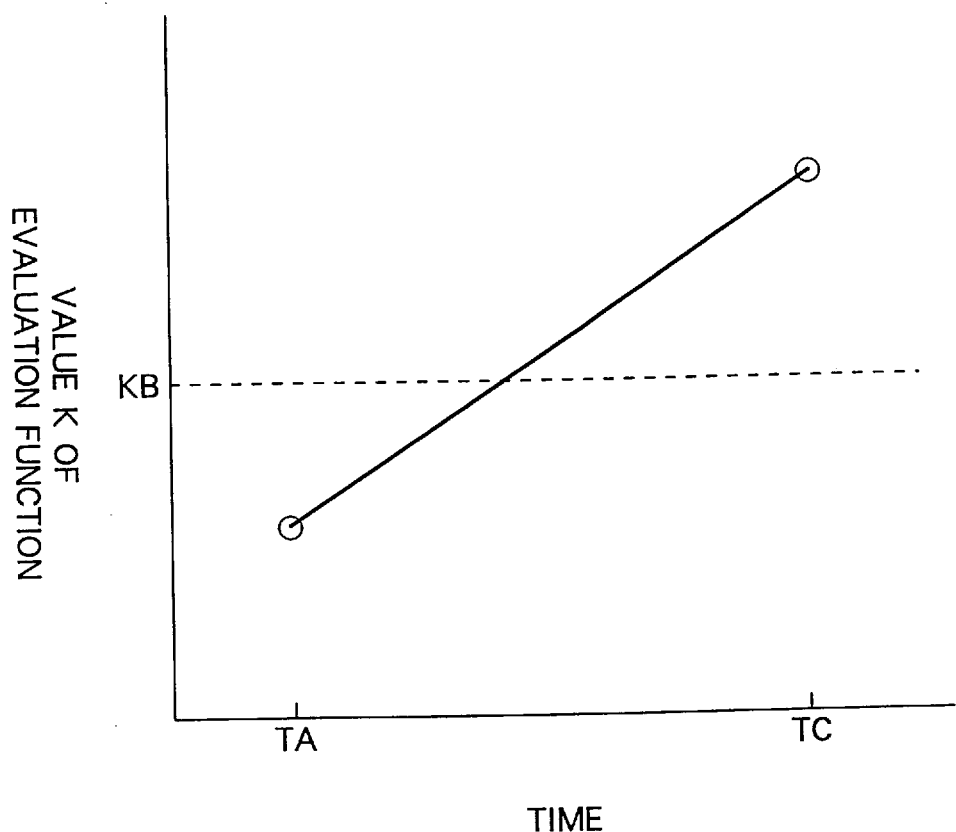
FIG. 45 is a graph for illustrating how an evaluation function employed by Embodiment 22 of the present invention varies with time.

FIG. 45 illustrates a change in the value K of the evaluation function, which is obtained by performing calculations on the basis of the Y-histograms of FIG. 44.

The central portion indicated by this Embodiment 22 is the center of a circle, which is found on the basis of the arcuate shape of the shape function by using the spoke filter. Further, the difference between the maximum value of the first-order shape function and the ordinate (namely, the Y-coordinate) of this center is the value K of the evaluation function.

As illustrated in FIG. 44, when the eye is opened or closed, the shape of the Y-histogram changes. As a result, as shown in FIG. 45, when closing the eye, the value K of the evaluation function is high. Thus, a threshold value KB is set, and it can be detected whether the eye is opened or closed.

Embodiment 23

Figure 46:
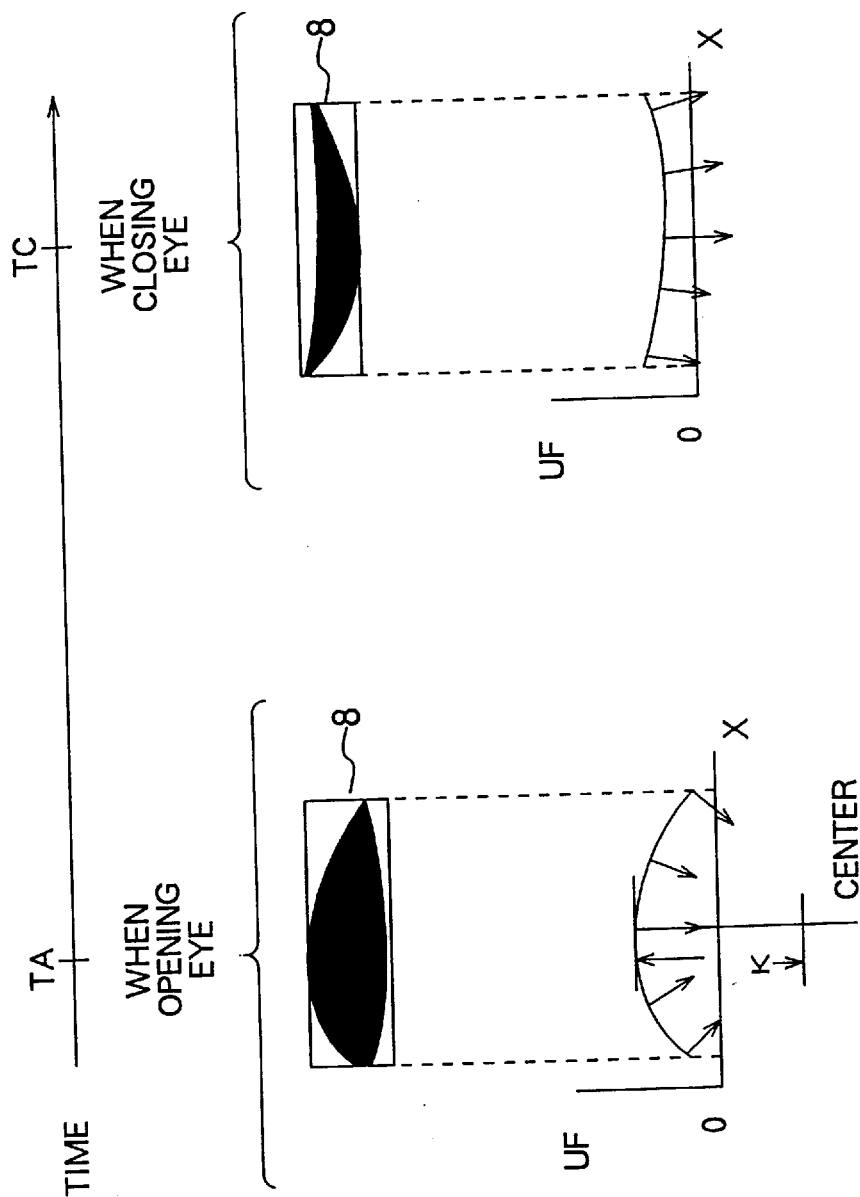
FIG. 46 is a diagram for illustrating a method for detecting the opened or closed condition of an eye, which is employed by Embodiment 23 of the present invention.

Next, Embodiment 23 of the present invention will be described hereinbelow by referring to FIG. 46. This figure is a diagram for illustrating a method for detecting the opened or closed condition of an eye, which is employed by this Embodiment 23 of the present invention. This diagram illustrates the relation among the lapse of time (from a moment TA, at which the eye is opened, to another moment TC, at which the eye is closed), the binary images of the eye presence area 8 varying with the lapse of time, and first-order shape functions (namely, upper boundary shape functions) of the binary images, and the centers of circles which are second-order shape functions obtained on the basis of the arcuate shapes of the first-order shape functions by using the spoke filter.

In the case of Embodiment 23, when the eye is opened or closed, the shape function changes. As a consequence, when closing the eye, the value K of the evaluation function is high. In an extreme case, as illustrated in this figure, when closing the eye, the positional relation between the convex portion and the concave portion is reversed, so that there occurs a divergent state in which no center is detected. Thus, it can be detected whether the eye is opened or closed.

Embodiment 24

Figure 47:
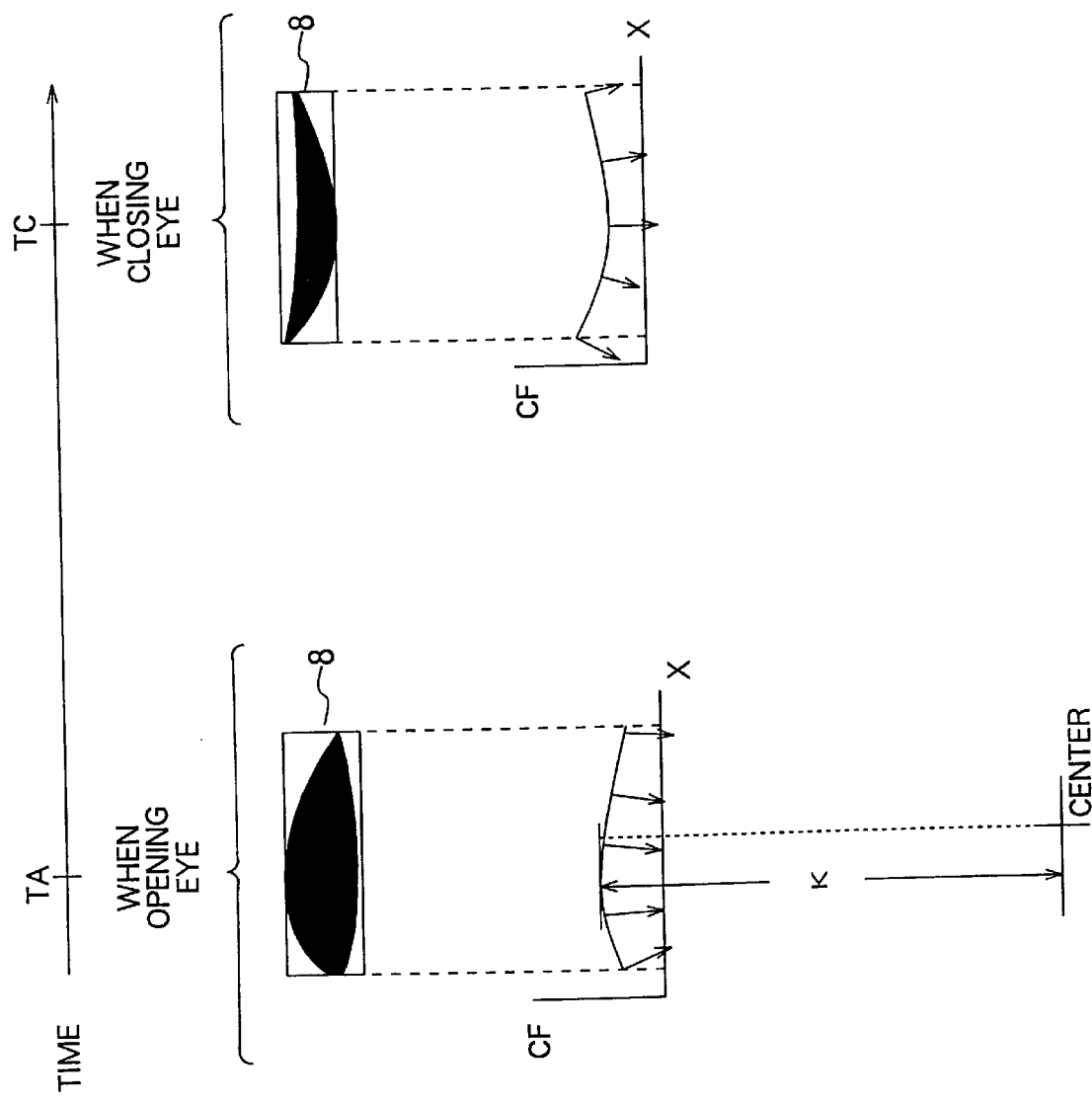
FIG. 47 is a diagram for illustrating a method for detecting the opened or closed condition of an eye, which is employed by Embodiment 24 of the present invention.

Next, Embodiment 24 of the present invention will be described hereinbelow by referring to FIG. 47. This figure is a diagram for illustrating a method for detecting the opened or closed condition of an eye, which is employed by this Embodiment 24 of the present invention. This diagram illustrates the relation among the lapse of time (from a moment TA, at which the eye is opened, to another moment TC, at which the eye is closed), the binary images of the eye presence area 8 varying with the lapse of time, and first-order shape functions (namely, Y-center-locus shape functions) using the shape of the Y-center lines (or curves) of the binary images, and the centers of circles which are second-order shape functions obtained on the basis of the arcuate shapes of the first-order shape functions by using the spoke filter.

In the case of the method employed in Embodiment 24, when the eye is opened or closed, the shape function changes, similarly as in the case of the method employed in Embodiment 22. Thus, it can be detected whether the eye is opened or closed.

Embodiment 25

Figure 48:
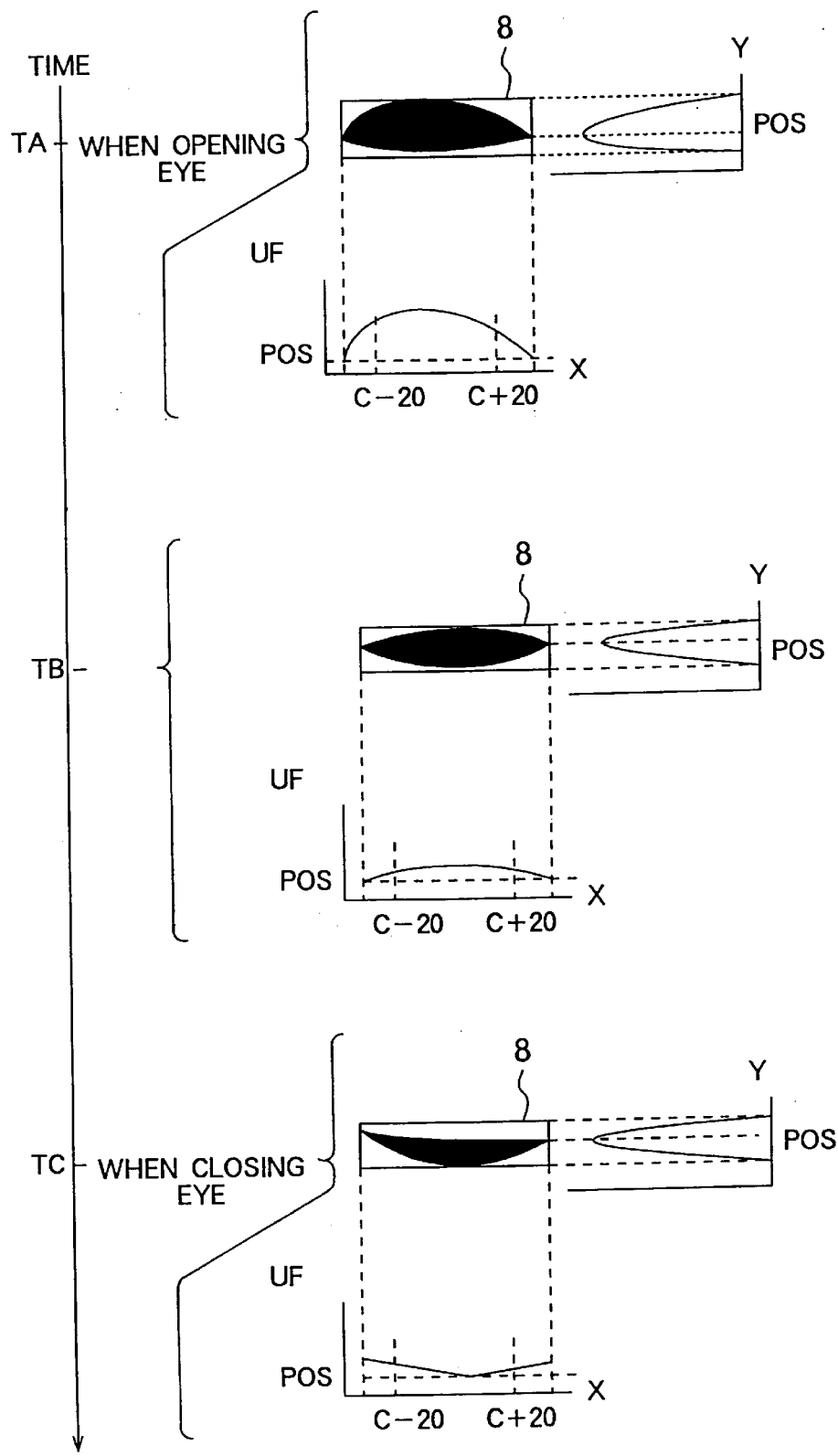
FIG. 48 is a diagram for illustrating a method for detecting the opened or closed condition of an eye, which is employed by Embodiment 25 of the present invention.

Next, Embodiment 25 of the present invention will be described hereinbelow by referring to FIGS. 48 and 49. FIG. 48 is a diagram for illustrating a method for detecting the opened or closed condition of an eye, which is employed by Embodiment 25 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, first shape functions (upper boundary shape functions) using the Y-coordinates of the upper boundaries of the binary images, and "X-histograms" (namely, second shape functions) defined herein as graphs for showing the distribution of the values obtained by accumulating the binary tone levels of pixels arranged in the X-direction correspondingly to each of the Y-coordinates in the eye presence area 8 in each of the binary images.

Figure 49:
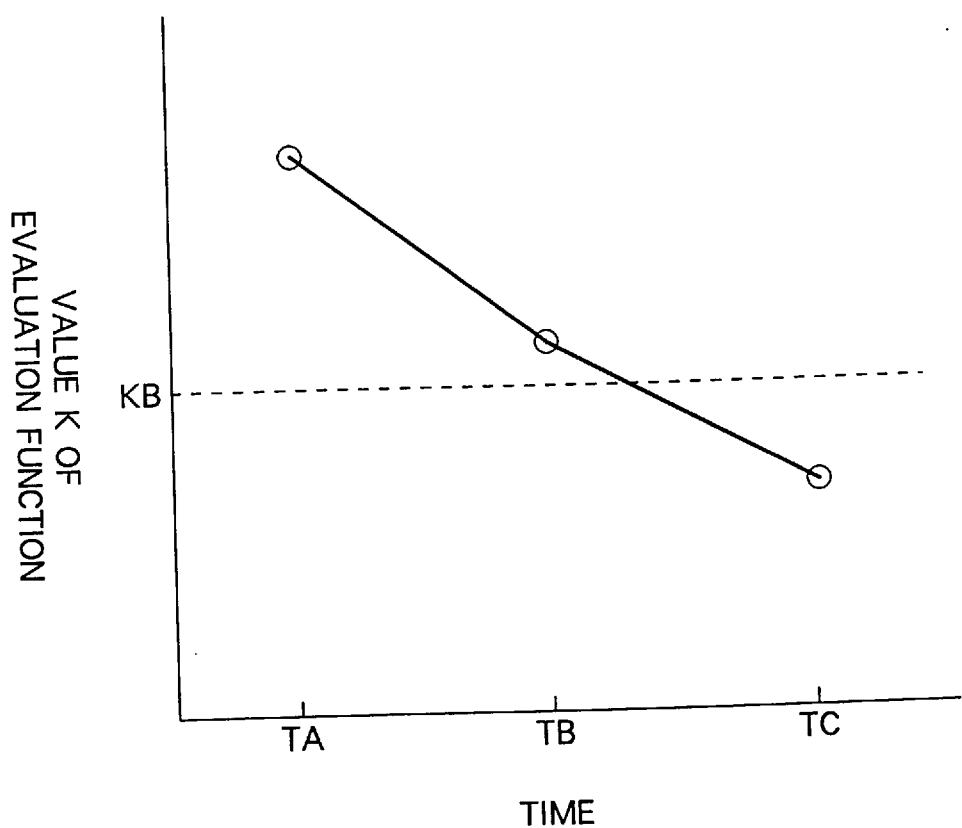
FIG. 49 is a graph for illustrating how an evaluation function employed by Embodiment 25 of the present invention varies with time.

FIG. 49 illustrates a change in the value K of the evaluation function calculated on the basis of the first shape function and the Y-coordinate of a peak in the X-histogram of FIG. 48.

In the case of this Embodiment 25, the sum of the differences between the Y-coordinates UF of the upper boundary in the predetermined range of the central portion of the eye (corresponding to the range of X of (C−20) to (C+20)) and the Y-coordinate POS of the peak of the X-histogram is the value K of the evaluation function given by the following equation (7). Incidentally, in the equation (7), the summation of the right side thereof is performed with respect to X of (C−20) to (C+20).

$$K=\Sigma(UF-POS) \qquad (7)$$

As illustrated in FIG. 48, when the eye is opened or closed, the shape of the first shape function and that of the X-histogram change. As a result, when the eye is closed, the value K of the evaluation function is low, as shown in FIG. 49. Thus, a threshold value KB is set, and it can be detected whether the eye is opened or closed.

Embodiment 26

Figure 50:
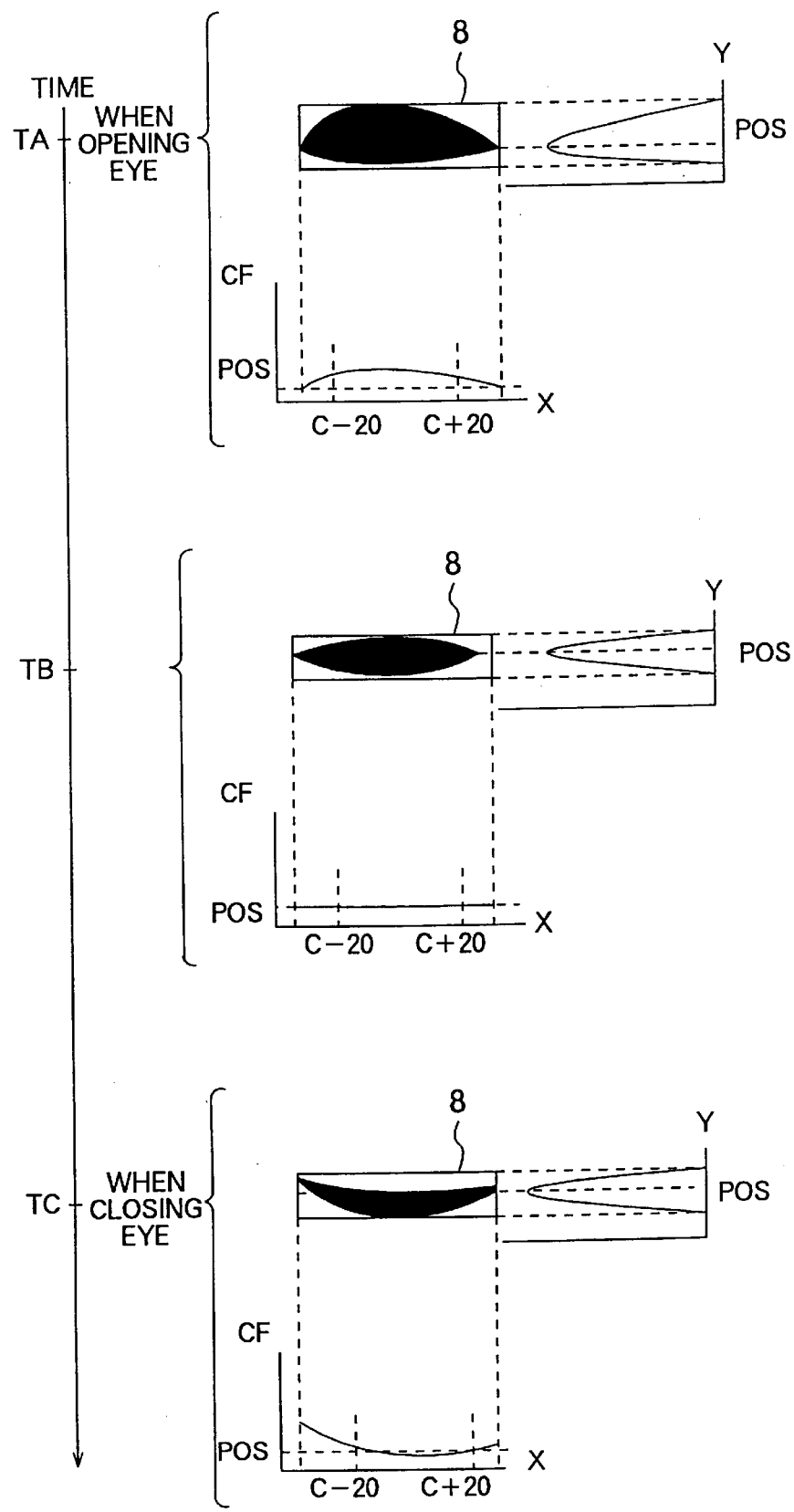
FIG. 50 is a diagram for illustrating a method for detecting the opened or closed condition of an eye, which is employed by Embodiment 26 of the present invention.

Next, Embodiment 26 of the present invention will be described hereinbelow by referring to FIGS. 50 and 51. FIG. 50 is a diagram for illustrating a method for detecting the opened or closed condition of an eye, which is employed by Embodiment 26 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, first shape functions (namely, Y-center-locus shape functions) using the shape of the Y-center-locus of the binary images, and X-histograms (namely, second shape functions) respectively corresponding to the binary images.

Figure 51:
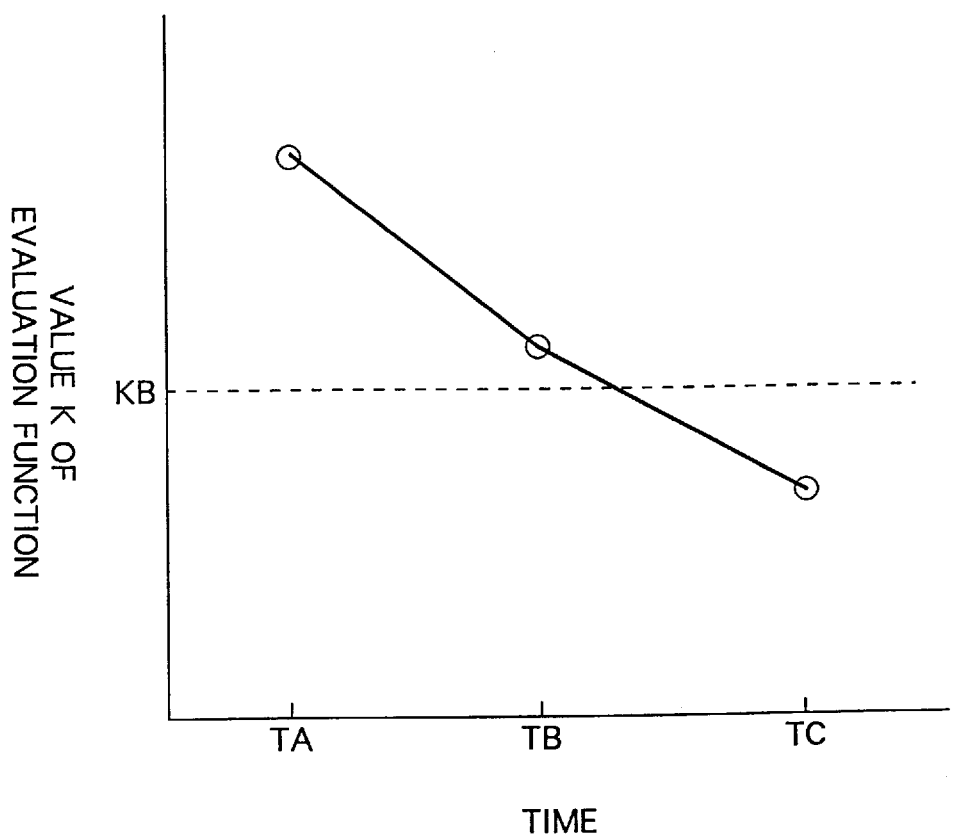
FIG. 51 is a graph for illustrating how an evaluation function employed by Embodiment 26 of the present invention varies with time.

FIG. 51 illustrates a change in the value K of the evaluation function calculated on the basis of the first shape function and the Y-coordinate of the peak in the X-histogram of FIG. 50.

In the case of this Embodiment 26, when the eye is opened or closed, the shape of the first shape function and that of the X-histogram change, similarly as in the case of the aforesaid Embodiment 25. Thus, a threshold value KB is set, and it can be detected whether the eye is opened or closed.

Embodiment 27

Figure 52:
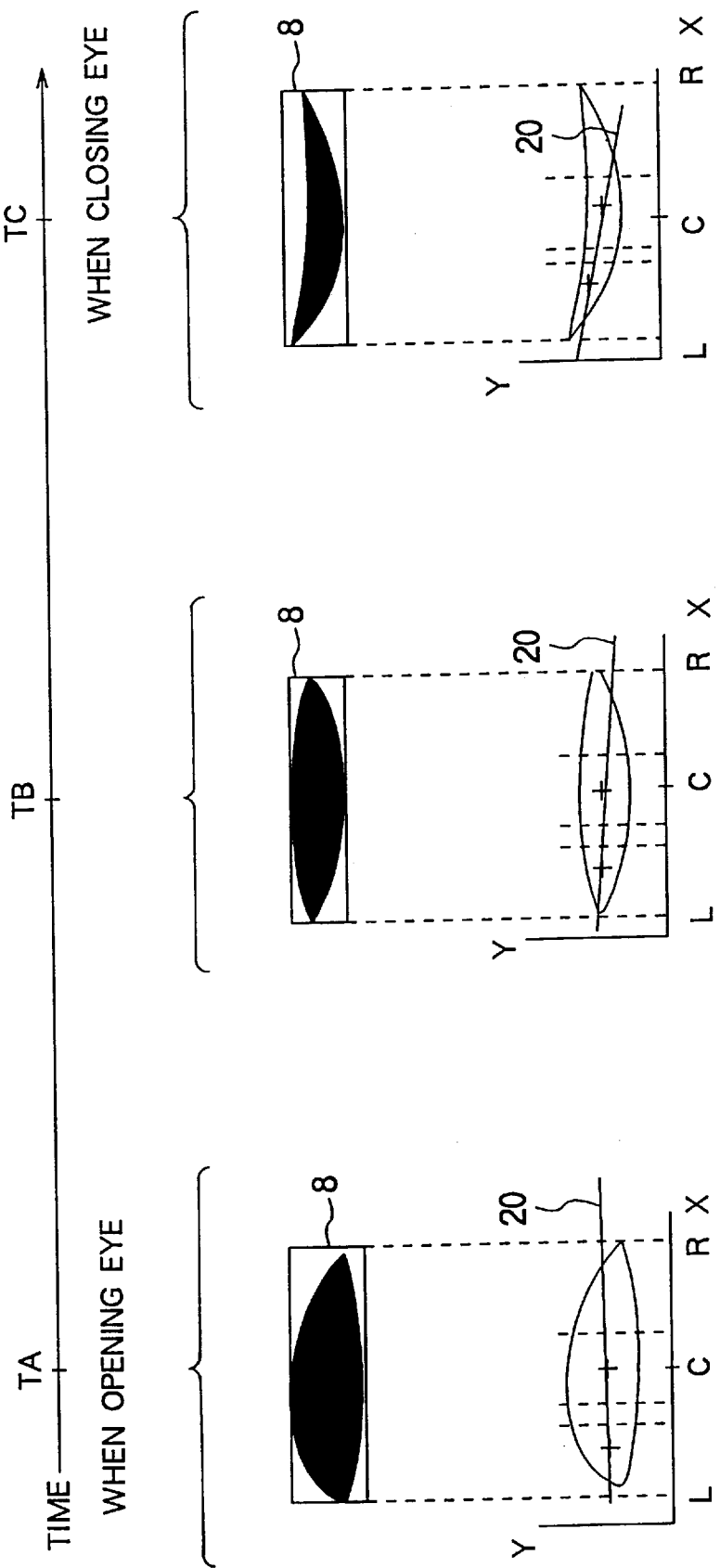
FIG. 52 is a diagram for illustrating a method for detecting the opened or closed condition of an eye, which is employed by Embodiment 27 of the present invention.

Next, Embodiment 27 of the present invention will be described hereinbelow by referring to FIGS. 52 and 53. FIG. 52 is a diagram for illustrating a method for detecting the opened or closed condition of an eye, which is employed by Embodiment 27 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, the barycenters or centroids (namely, first shape functions) of predetermined portions or ranges of the binary images of an eye, and lines connecting two of the barycenters or centroids (namely, second shape functions) of the predetermined portions or ranges of the binary images of the eye.

Figure 53:
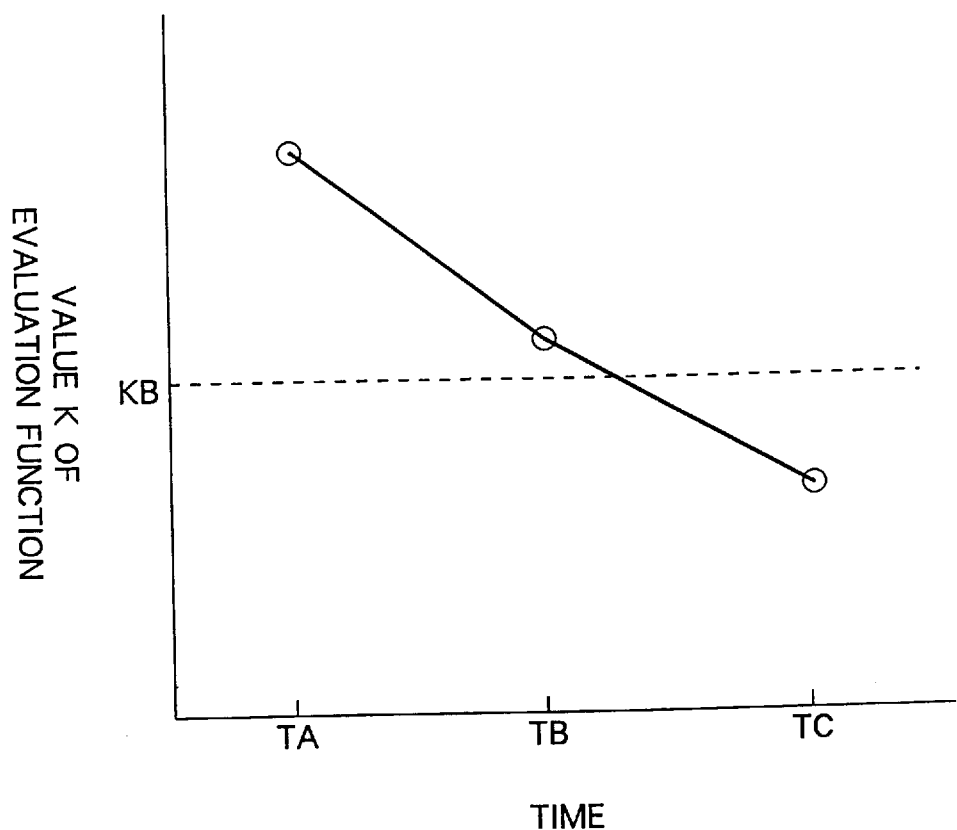
FIG. 53 is a graph for illustrating how an evaluation function employed by Embodiment 27 of the present invention varies with time.

FIG. 53 illustrates a change in the value K of the evaluation function calculated on the basis of the shape functions of FIG. 52.

In each graph of FIG. 52, marks "+" represent the barycenter or centroid (XC, YC) of a predetermined part of the central portion of the image of the eye, which corresponds to the range of X of (C−5) to (C+5) and the barycenter or centroid (XL, YL) of a predetermined part of the left end portion of the image of the eye, which corresponds to the range of X of L to (L+10). Each of the barycenters or centroids is the mean or average of the coordinates of black pixels contained in the corresponding part of the image. For example, the barycenters (XC, YC) or centroids is given by the following equation (8) using the total number N of black pixels contained in the predetermined part of the central portion of the image.

$$(XC, YC)=(\Sigma X/N, \Sigma Y/N) \qquad (8)$$

In the case of this Embodiment 27, the gradient of a line 20 connecting the barycenter or centroid (XC, YC) of the predetermined part of the central portion of the image of the eye with the barycenter or centroid (XL, YL) of the predetermined part of the left end portion of the image thereof is given by the following equation (9) and represents the value K of the evaluation function.

$$K=(YC-YL)/(XC-XL) \qquad (9)$$

As illustrated in FIG. 52, when the eye is opened or closed, the shape of the first shape function and that of the second shape function change. As a result, when the eye is closed, the value K of the evaluation function is low, as shown in FIG. 53. Thus, a threshold value is set at KB, and it can be detected whether the eye is opened or closed.

Moreover, in the case of this embodiment, the average of the values of the first shape function corresponding to the predetermined part of the left end portion of the image of the eye is used for obtaining the evaluation function. However, similar effects can be obtained in the case of using the average of the values of the first shape function corresponding to the predetermined part of the right end portion of the image thereof.

Embodiment 28

Figure 54:
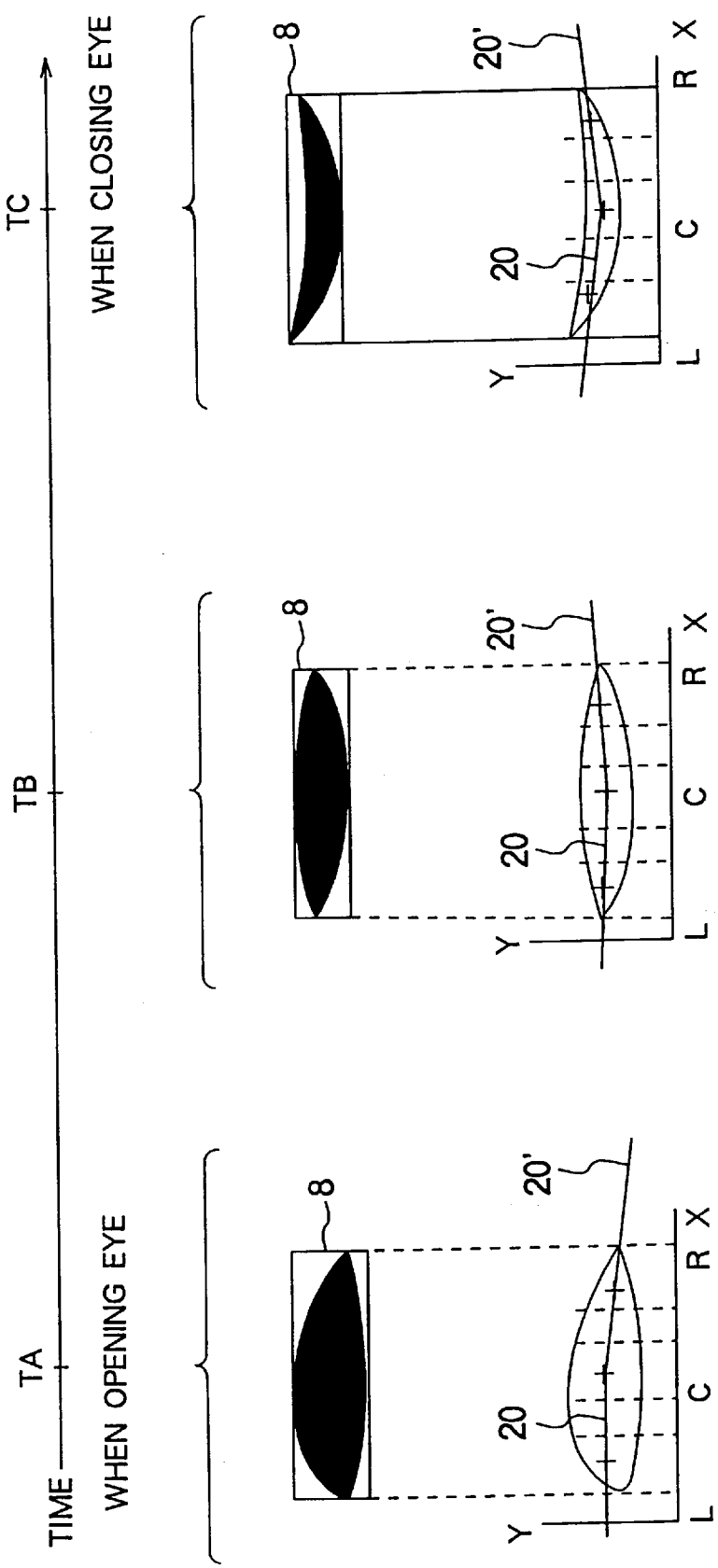
FIG. 54 is a diagram for illustrating a method for detecting the opened or closed condition of an eye, which is employed by Embodiment 28 of the present invention.

Next, Embodiment 28 of the present invention will be described hereinbelow by referring to FIGS. 54 and 55. FIG. 54 is a diagram for illustrating a method for detecting the opened or closed condition of an eye, which is employed by Embodiment 28 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, the barycenters or centroids (namely, first shape functions) of predetermined portions or ranges of the binary images of an eye, and lines connecting two of the barycenters or centroids (namely, second shape functions) of the predetermined portions or ranges of the binary images of the eye.

Figure 55:
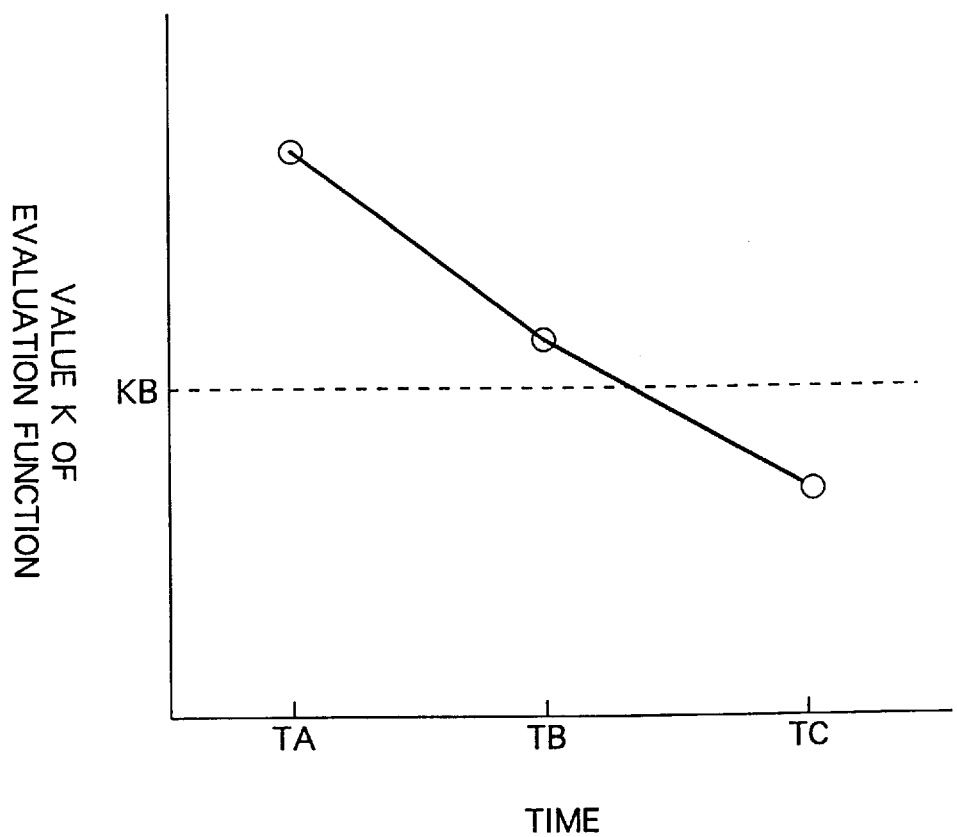
FIG. 55 is a graph for illustrating how an evaluation function employed by Embodiment 28 of the present invention varies with time.

FIG. 55 illustrates a change in the value K of the evaluation function calculated on the basis of the shape functions of FIG. 54.

In the case of this Embodiment 28, the difference between the gradient of a line 20 connecting the barycenter or centroid (XC, YC) of the predetermined part, whose X-coordinates range from (C−5) to (C+5), of the central portion of the image of the eye with the barycenter or centroid (XL, YL) of the predetermined part, whose X-coordinates range from L to (L+10), of the left end portion of the image thereof and the gradient of another line 20' connecting the barycenter or centroid (XC, YC) of the same (predetermined) part of the central portion of the image of the eye with the barycenter or centroid (XR, YR) of the predetermined part, whose X-coordinates range from R to (10−R), of the left end portion of the image thereof is given by the following equation (10) and represents the value K of the evaluation function.

$$K=(YC-YL)/(XC-XL)-(YC-YR)/(XC-XR) \qquad (10)$$

As illustrated in FIG. 54, when the eye is opened or closed, the shape of the first shape function and that of the second shape function change. As a result, when the eye is closed, the value K of the evaluation function is low, as shown in FIG. 55. Thus, a threshold value is set at KB, and it can be detected whether the eye is opened or closed.

Embodiment 29

Figure 56:
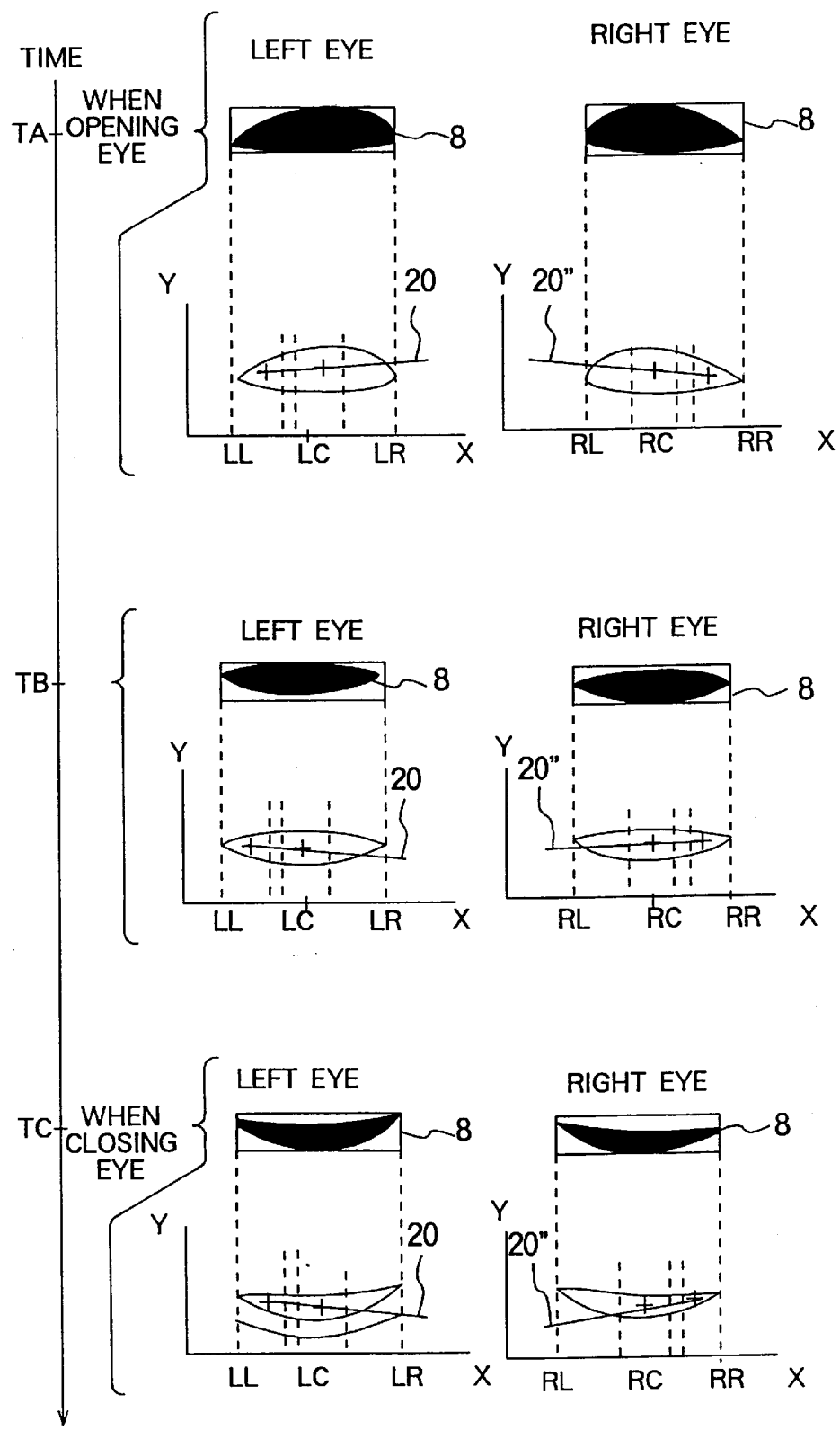
FIG. 56 is a diagram for illustrating a method for detecting the opened or closed condition of an eye, which is employed by Embodiment 29 of the present invention.

Next, Embodiment 29 of the present invention will be described hereinbelow by referring to FIGS. 56 and 57. FIG. 56 is a diagram for illustrating a method for detecting the opened or closed condition of an eye, which is employed by Embodiment 29 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, the barycenters or centroids (namely, first shape functions) of predetermined portions or ranges of the binary images of an eye, and two lines, each of which connects two of the barycenters or centroids (namely, second shape functions) of the predetermined portions or ranges of the binary images of the eye correspondingly to each of the moments TA, TB and TC.

Figure 57:
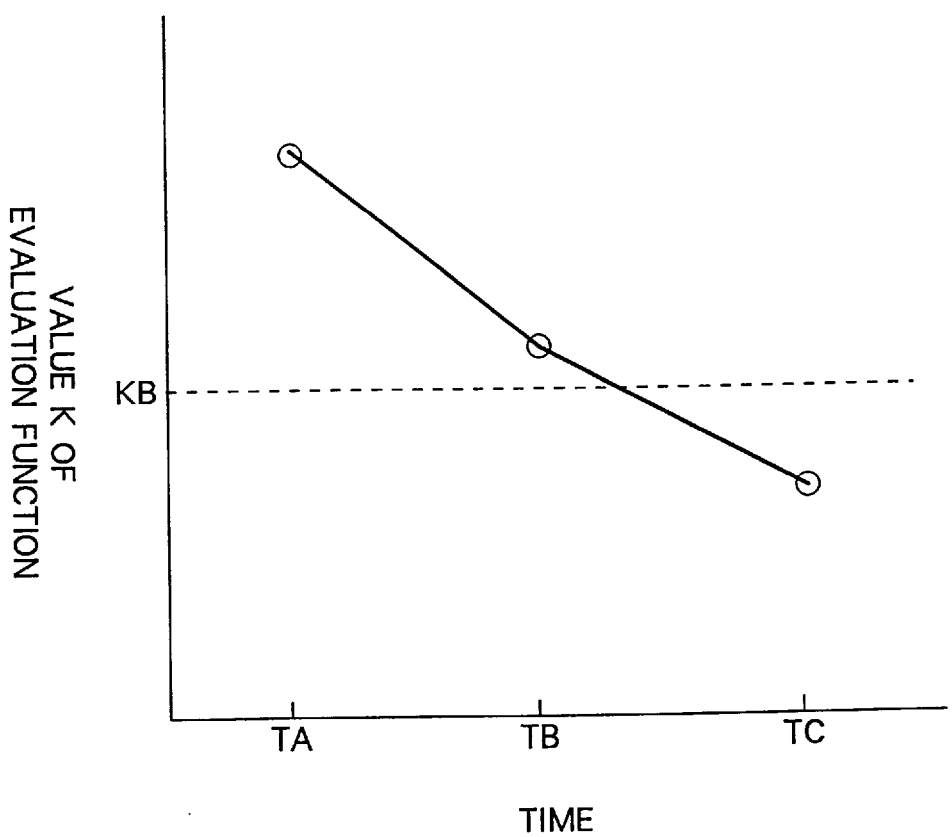
FIG. 57 is a graph for illustrating how an evaluation function employed by Embodiment 29 of the present invention varies with time.

FIG. 57 illustrates a change in the value K of the evaluation function calculated on the basis of the shape functions of FIG. 56.

In the case of this embodiment 29, the difference between the gradient of a line 20 connecting the barycenter or centroid (XCL, YCL) of the predetermined part, whose X-coordinates range from (LC−5) to (LC+5), of the central portion of the image of the left eye with the barycenter or centroid (XLL, YLL) of the predetermined part, whose X-coordinates range from LL to (LL+10), of the left end portion of the image thereof and the gradient of another line 20" connecting the barycenter or centroid (XCR, YCR) of the corresponding (predetermined) part, whose X-coordinates range from (RC−5) to (RC+5), of the central portion of the image of the right eye with the barycenter or centroid (XRR, YRR) of the predetermined part, whose X-coordinates range from RR to (10−RR), of the left end portion of the image thereof is given by the following equation (11) and represents the value K of the evaluation function.

$$K=(YCL-YLL)/(XCL-XLL)-(YCR-YRR)/(XCR-XRR) \qquad (11)$$

As illustrated in FIG. 56, when the eye is opened or closed, the shape of the first shape function and that of the second shape function change. As a result, when the eye is closed, the value K of the evaluation function is low, as shown in FIG. 57. Thus, a threshold value KB is set, and it can be detected whether the eye is opened or closed.

Further, in this case, the shapes of the predetermined ranges of the outer end portions respectively corresponding to the left and right eyes are used for obtaining the evaluation function. However, a similar effect can be obtained in the case that the shapes of the predetermined ranges of the inner end portions of the left and right eyes are used.

Embodiment 30

Figure 58:
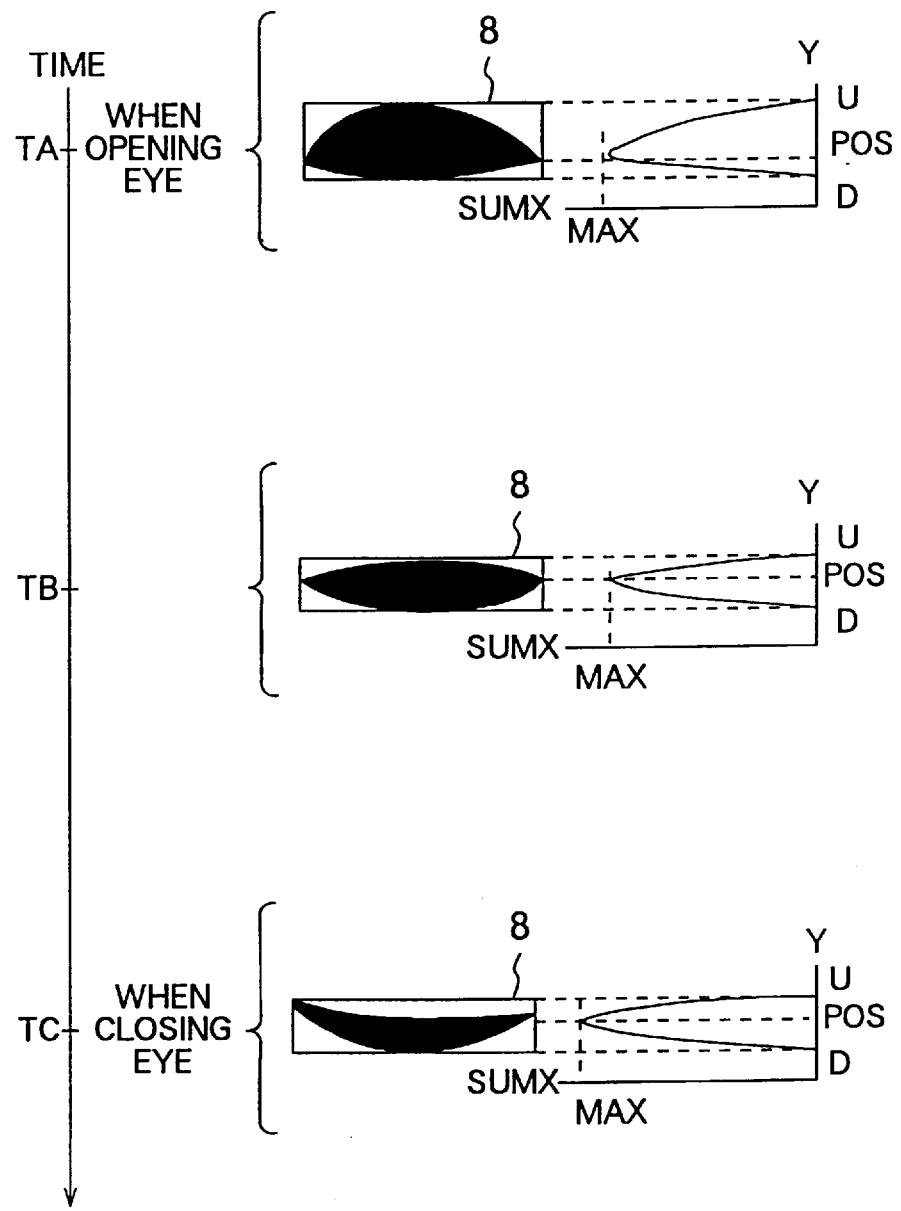
FIG. 58 is a diagram for illustrating a method for detecting the opened or closed condition of an eye, which is employed by Embodiment 30 of the present invention.

Next, Embodiment 30 of the present invention will be described hereinbelow by referring to FIGS. 58 and 59. FIG. 58 is a diagram for illustrating a method for detecting the opened or closed condition of an eye, which is employed by Embodiment 30 of the present invention. This figure shows the relation among the lapse of time (from a moment TA, at which the eye is opened, to another moment TC, at which the eye is closed, through an intermediate moment TB therebetween), the binary images of the eye presence area 8 varying with the lapse of time, and X-histograms (namely, shape functions) showing the distribution of the values obtained by the accumulation of the binary tone levels of pixels arranged in the X-direction correspondingly to each of the Y-coordinates in each of the binary images. Further, each of the X-histograms is practically obtained by scanning the eye presence area 8 in the X-direction and counting the black pixels corresponding to each of the Y-coordinates (incidentally, "SUMX" represents the count (namely, the total number) of the black pixels corresponding to each of the Y-coordinates).

Figure 59:
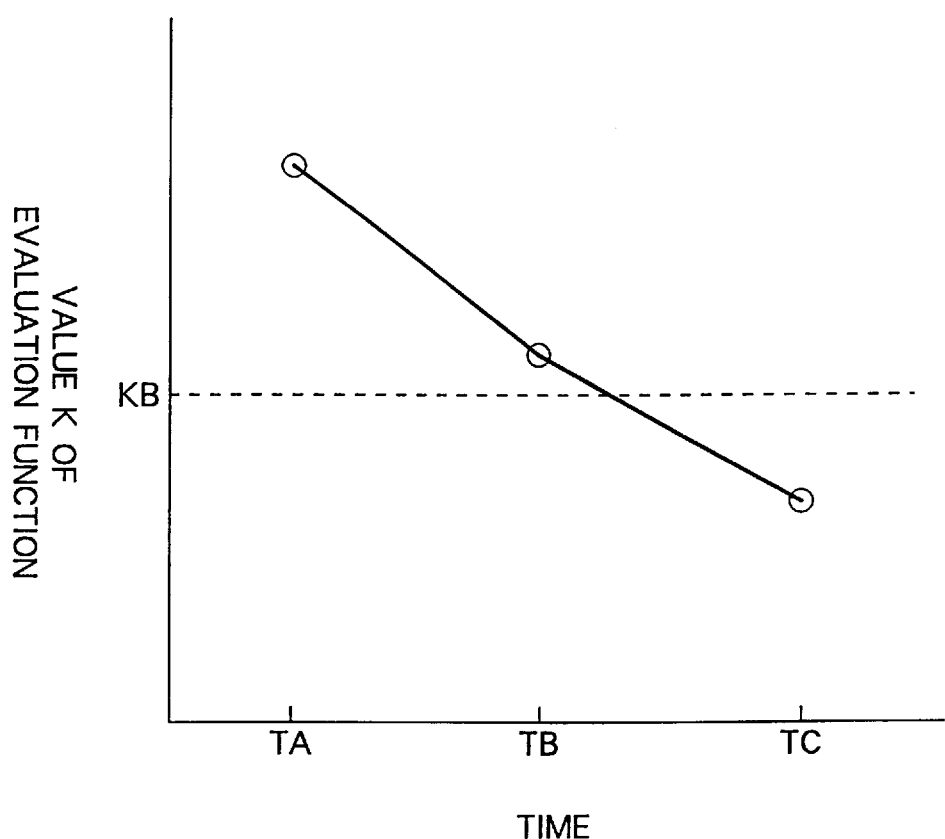
FIG. 59 is a graph for illustrating how an evaluation function employed by Embodiment 30 of the present invention varies with time.

FIG. 59 illustrates a change in the value K of the evaluation function calculated on the basis of the X-histogram of FIG. 58.

In the case of this Embodiment 30, the Y-coordinates POS, U and D of the peak of the X-histogram and the upper end and the lower end thereof are detected. Further, the value K of the evaluation function is obtained from the relative positional relation as expressed by the following equation (12). Incidentally, in this case, the value K of the evaluation function indicates the relative position of the peak of the X-histogram.

$$K=(U-POS)/(POS-D) \qquad (12)$$

As illustrated in FIG. 58, when the eye is opened or closed, the shape of the X-histogram changes. As a result, when the eye is closed, the value K of the evaluation function is low, as shown in FIG. 59. Thus, a threshold value KB can be set and it can be detected whether the eye is opened or closed.

Embodiment 31

Figure 60:
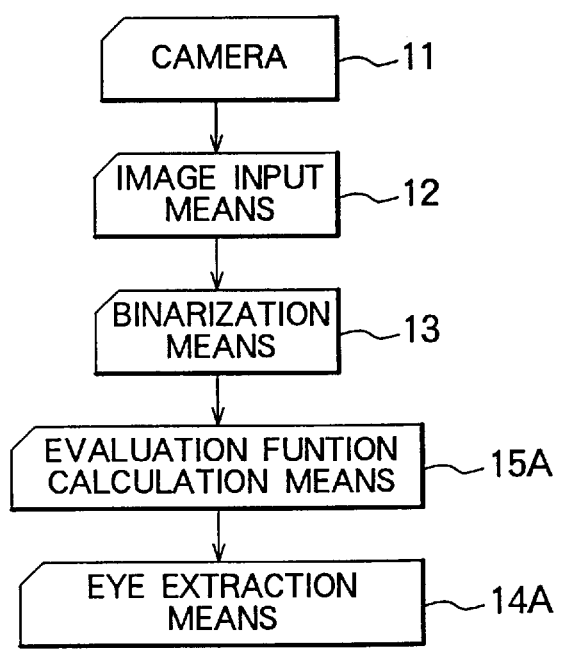
FIG. 60 is a diagram for illustrating the configuration of Embodiment 31 of the present invention.
Figure 61:
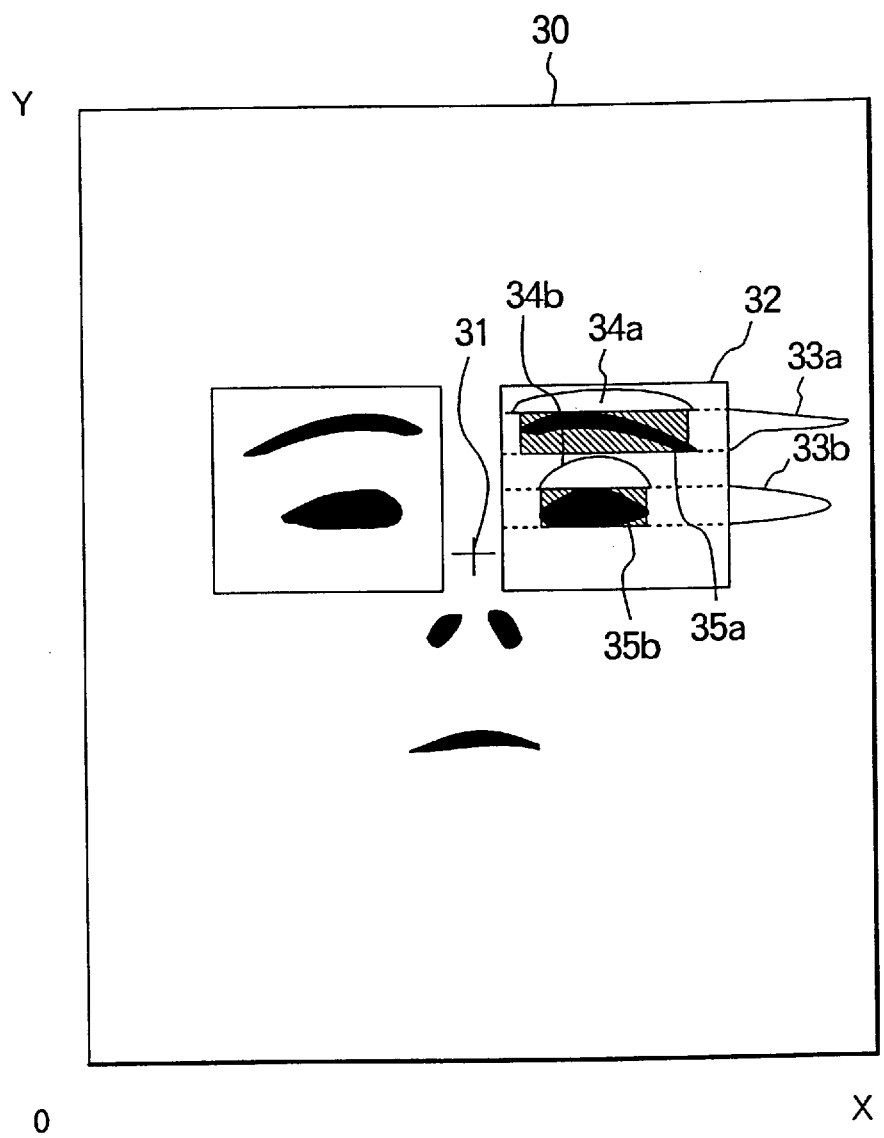
FIG. 61 is a diagram for illustrating a method for extracting an candidate-for-eye presence area of Embodiment 31 of the present invention.

Next, Embodiment 31 of the present invention will be described hereinbelow by referring to FIGS. 60 and 61. FIG. 60 is a diagram for illustrating the configuration of this Embodiment 31 of the present invention. FIG. 61 is a diagram for illustrating a method of this Embodiment 31 for extracting an candidate-for-eye-presence-area from the binary image of a face.

As shown in FIG. 60, this Embodiment 31 is provided with a camera 11, an image input means 12, a binarization means 13, an evaluation function calculation means 15A and an eye extraction means 14A.

A part of the operation of this Embodiment 31 is similar to the part of the operation of the aforementioned Embodiment 1 from the beginning to the binarization. However, the evaluation function calculation means 15A first finds the barycenter or centroid 31 from the average of the coordinates of black pixels of a binary image 30. Subsequently, a rectangular areas existing in the predetermined ranges in the X-direction on the left and right sides of this barycenter or centroid 31 are set as eye presence areas 32. Further, in the eye presence area 32, X-histograms 33 (namely, 33a and 33b) are generated. Then, zonal regions are set on the basis of the X-histograms. Furthermore, Y-histograms 34 (namely, 34a and 34b) showing the distribution of the values obtained by the accumulation of the binary tone levels of pixels arranged in the Y-direction of columns of the zonal regions are produced. Next, hatched candidate areas 35 (namely, 35a and 35b) for an eye presence area are extracted.

Hereupon, the evaluation functions of one of the aforementioned embodiments of the present invention, which respectively correspond to all of the candidate areas 35, are calculated by the evaluation function calculation means 15A. Then, the calculated values of the evaluation functions are recorded in a memory. Here, note that when blinking, the shape of an eye changes and the value K of the corresponding evaluation function changes and that in contrast, the shape of an eyebrow and that of the frame of a pair of spectacles hardly change with time and thus a change in the value K of the corresponding evaluation function is very small. Thus, the eye extraction means 14A checks how the values K of the evaluation functions vary with time. Further, the eye extraction means 14A discriminates among the eye, the brow and the frame of a pair of spectacles according to the values K of the evaluation functions and to changes therein. Thus, the eye extraction means 14A extracts the eye presence area and judges whether the eye is opened or closed.

Embodiment 32

Figure 62:
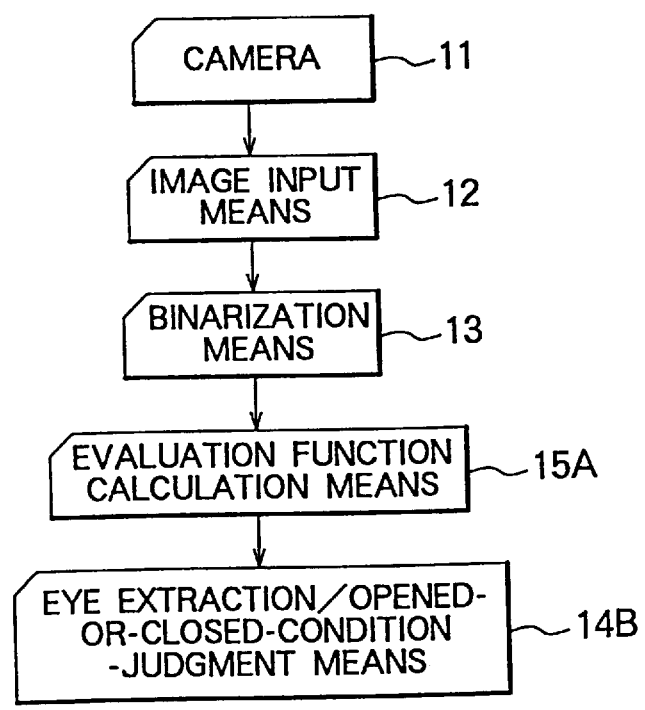
FIG. 62 is a diagram for illustrating the configuration of Embodiment 32 of the present invention.
Figure 63:
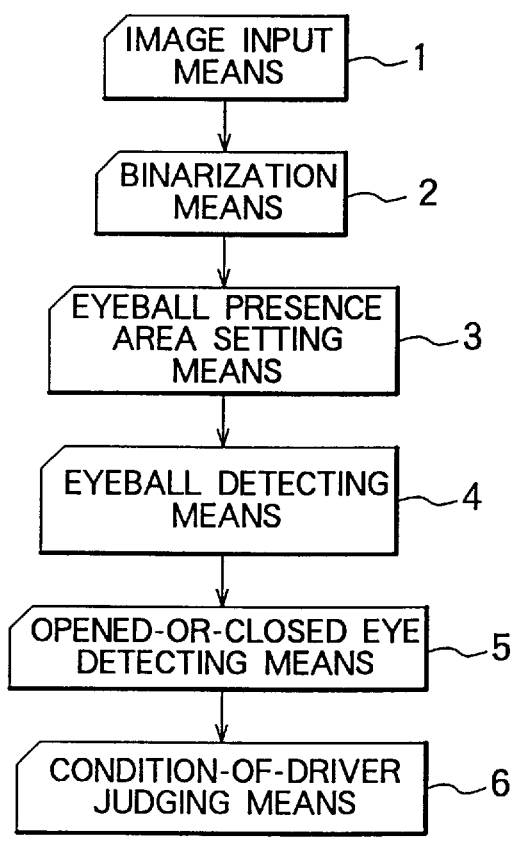
FIG. 63 is a diagram for illustrating the configuration of the conventional system for detecting the condition of a driver.
Figure 64:
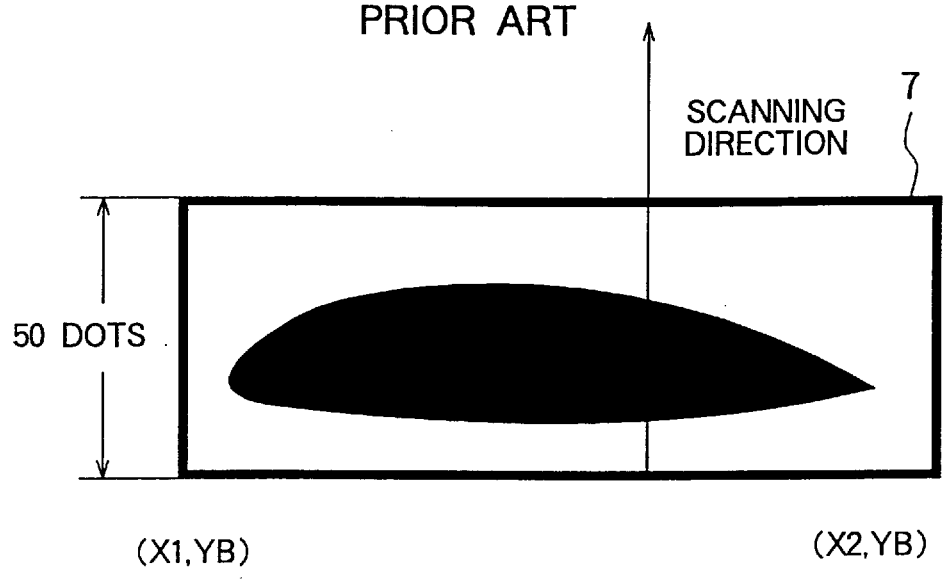
FIG. 64 is a diagram for illustrating the conventional method for detecting the opened or closed condition of an eye.
Figure 65A:
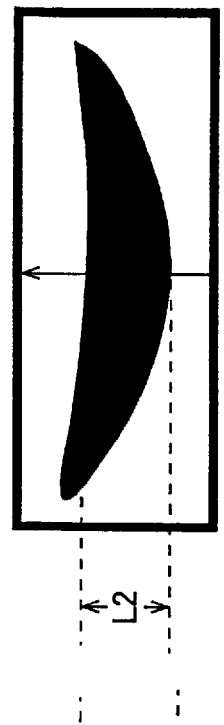
FIGS. 65A and 65B are diagrams for illustrating the problem concerning the conventional method of detecting the opened or closed condition of an eye.
Figure 65B:
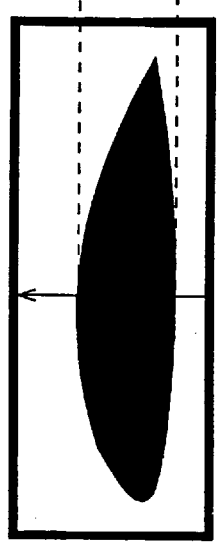

Next, Embodiment 32 of the present invention will be described hereinbelow by referring to FIG. 62. FIG. 62 is a diagram for illustrating the configuration of this Embodiment 32 of the present invention. This embodiment is a combination of the aforementioned Embodiment 1 and the aforesaid Embodiment 31. The evaluation functions of one of the aforementioned embodiments, which respectively correspond to all of the candidate areas 35, are calculated by the evaluation function calculation means 15A. Then, the calculated values of the evaluation functions are recorded in a memory. Here, note that when blinking, the shape of an eye changes and the value K of the corresponding evaluation function changes and that in contrast, the shape of a brow and that of the frame of a pair of spectacles hardly change with time and thus a change in the value K of the corresponding evaluation function is very small. Thus, the eye extraction means 14B checks how the values K of the evaluation functions vary with time. Further, the eye extraction means/opened-or-closed-condition-judgement means 14B discriminates among the eye, the brow and the frame of a pair of spectacles according to the values K of the evaluation functions and to changes therein. Thus, the eye extraction/opened-or-closed-condition-judgement means 14B extracts the eye presence area. Simultaneously, the eye extraction/opened-or-closed-condition-judgement means 14B determined a threshold value from the value K of the evaluation function and then judges whether the eye is opened or closed.

Each of the aforementioned embodiments of the present invention can accurately judge whether an eye is opened or closed, even in the cases that change in the number of continuous black pixels arranged in the Y-direction, which occurs at the time of closing the eye, is small and that change in the maximum number of continuous black pixels arranged in the Y-direction results from change in upward or downward direction of a face or from change in leftward or rightward inclination of the face, by directing attention to a change in shape of the eye, which is caused by closing the eye. Moreover, in the foregoing descriptions of the embodiments of the present invention, there have been described the cases in which the present invention is applied to automobiles. The present invention, however, can be applied to all of the types of vehicles such as a train, a monorail, an aircraft and a ship.

Although the preferred embodiments of the present invention have been described above, it should be understood that the present invention is not limited thereto and that other modifications will be apparent to those skilled in the art without departing from the spirit of the invention.

The scope of the present invention, therefore, should be determined solely by the appended claims.

What is claimed is:

1. A facial image processing system comprising:

camera for taking a facial image;

image input means for inputting a video signal sent from the camera;

binarization means for binarizing the facial image inputted from the image input means;

eye extraction means for extracting an eye presence area, which includes an eye, from the binarized facial image;

evaluation function calculation means for calculating a shape function representing a shape feature of the eye from the eye presence area and for calculating an evaluation function according to the shape function; and open-or-closed condition judgment means for judging according to the evaluation function whether the eye is open or closed;

wherein the evaluation function calculation means obtains a first-order shape function on the basis of the binary image of the eye presence area and calculates a second-order shape function according to the first-order shape function and further calculates an evaluation function according to the second-order shape function.

2. The facial image processing system according to claim 1, wherein the second-order shape function is an approximate line corresponding to the first-order shape function.

3. The facial image processing system according to claim 2, wherein the evaluation function is a gradient of the approximate line.

4. The facial image processing system according to claim 3, wherein the first-order shape function is an upper boundary of the binary image of the eye presence area.

5. The facial image processing system according to claim 4, wherein the approximate line is obtained by using a method of least squares as a line having a shape close to a shape of a predetermined range of an end portion of the upper boundary.

6. The facial image processing system according to claim 1, wherein the second-order shape function is two approximate lines corresponding to the first-order shape function.

7. The facial image processing system according to claim 6, wherein the evaluation function is a difference between gradients of the two approximate lines.

8. The facial image processing system according to claim 7, wherein the first-order shape function is an upper boundary of the binary image of the eye presence area.

9. The facial image processing system according to claim 8, wherein the two approximate lines are obtained by using a method of least squares as figures having shapes close to those of a predetermined range of an end portion of the upper boundary and an entire range of the boundary, respectively.

10. The facial image processing system according to claim 8, wherein the two approximate lines are obtained by using a method of least squares as figures having shapes close to those of a predetermined range of a left end portion of the upper boundary and a predetermined range of a right end portion thereof, respectively.

11. The facial image processing system according to claim 7, wherein the first shape functions are upper boundaries of left and right eyes contained in the binary image of the eye presence area.

12. The facial image processing system according to claim 11, wherein the two approximate lines are obtained by using a method of least squares as figures having shapes close to those of a predetermined range of an end portion of the upper boundary of the left eye and a predetermined range of an end portion of the upper boundary of the right eye, respectively.

13. The facial image processing system according to claim 1, wherein the second-order shape function is an average of values of the first-order shape function at two places.

14. The facial image processing system according to claim 13, wherein the evaluation function is a difference between the averages of the values of the first-order shape function at the two places.

15. The facial image processing system according to claim 14, wherein the first-order shape function is an upper boundary of the binary image of the eye presence area.

16. The facial image processing system according to claim 15, wherein the average of the values of the first-order shape function at the two places is obtained from predetermined ranges of a central portion and an end portion of the upper boundary.

17. The facial image processing system according to claim 15, wherein the average of values of the two places is obtained from predetermined ranges of a central portion and both end portions of the upper boundary.

18. The facial image processing system according to claim 14, wherein the first-order shape functions are upper boundaries of left and right eyes contained in the binary image of the eye presence area.

19. The facial image processing system according to claim 18, wherein the average of the values of the first-order shape function at the two places is obtained from predetermined ranges of central portions of both of the eyes and end portions of the upper boundaries of both of the eyes.

20. The facial image processing system according to claim 1, wherein the first-order shape function is a barycenter of a predetermined range of an image of an eye contained in the binary image of the eye presence area.

21. The facial image processing system according to claim 20, wherein the second-order shape function is a line passing through two barycenters.

22. The facial image processing system according to claim 21, wherein the evaluation function is a difference between a gradient of a first line and a gradient of a second line.

23. The facial image processing system according to claim 22, wherein the first line is a line passing through a barycenter of a central portion of the image of the eye and a barycenter of a left end portion thereof, wherein the second line is a line passing through the barycenter of the central portion of the image of the eye and a barycenter of a right end portion thereof.

24. The facial image processing system according to claim 20, wherein the first-order functions are a barycenter of a predetermined range of an image of a left eye contained in the binary image of the eye presence areas and a barycenter of a predetermined range of an image of a right eye contained therein.

25. The facial image processing system according to claim 24, wherein the second-order functions are a first line passing through two barycenters of portions of an image of a left eye and a second line passing through two barycenters of portions of an image of a right eye.

26. The facial image processing system according to claim 25, wherein the evaluation function is a difference between a gradient of the first line and a gradient of the second line.

27. The facial image processing system according to claim 26, wherein the first line is a line passing through a barycenter of a central portion of the image of the left eye and a barycenter of a left end portion thereof, wherein the second line is a line passing through the barycenter of the central portion of the image of the right eye and a barycenter of a right end portion thereof.

28. A facial image processing system comprising:

camera for taking a facial image;

image input means for inputting a video signal sent from the camera;

binarization means for binarizing the facial image inputted from the image input means;

eye extraction means for extracting an eye presence area, which includes an eye, from the binarized facial image;

evaluation function calculation means for calculating a shape function representing a shape feature of the eye from the eye presence area and for calculating an evaluation function according to the shape function; and open-or-closed condition judgment means for judging according to the evaluation function whether the eye is open or closed;

wherein the evaluation function calculation means obtains first-order and second-order shape functions from the binary image of the eye presence area and calculates an evaluation function according to the first-order and second-order shape functions.

29. The facial image processing system according to claim 28, wherein the first-order shape function is an upper boundary of the binary image of the eye presence area.

30. The facial image processing system according to claim 29, wherein the second-order shape function is an X-histogram of the binary image of the eye presence area.

31. The facial image processing system according to claim 30, wherein the evaluation function is a difference between the upper boundary and a peak of the X-histogram.

32. The facial image processing system according to claim 31, wherein the evaluation function is a sum of differences between coordinates of the upper boundary and peaks of the X-histograms in a central portion of the binary image.

* * * * *